(12) United States Patent
Austen et al.

(10) Patent No.: US 8,486,953 B2
(45) Date of Patent: Jul. 16, 2013

(54) THIENOPYRIMIDINES FOR PHARMACEUTICAL COMPOSITIONS

(75) Inventors: Matthias Austen, Goettingen (DE); Phillip Black, Saffron Walden (GB); Wesley Blackaby, Saffron Walden (GB); John Danilewicz, Canterbury (GB); Ian Linney, Saffron Walden (GB); Kay Schreiter, Goettingen (DE); Martin Schneider, Goettingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 55 days.

(21) Appl. No.: 13/060,731

(22) PCT Filed: Aug. 24, 2009

(86) PCT No.: PCT/EP2009/060876
§ 371 (c)(1),
(2), (4) Date: May 4, 2011

(87) PCT Pub. No.: WO2010/023181
PCT Pub. Date: Mar. 4, 2010

(65) Prior Publication Data
US 2012/0128686 A1 May 24, 2012

(30) Foreign Application Priority Data
Aug. 26, 2008 (EP) .................... 08015049

(51) Int. Cl.
C07D 495/04 (2006.01)
A61K 31/381 (2006.01)
A61P 9/00 (2006.01)

(52) U.S. Cl.
USPC ........................ 514/260.1; 544/278

(58) Field of Classification Search
USPC ........................ 544/278; 514/260.1
See application file for complete search history.

(56) References Cited

U.S. PATENT DOCUMENTS

| | | | |
|---|---|---|---|
| 5,686,457 A | 11/1997 | Traxler et al. |
| 6,096,749 A | 8/2000 | Traxler et al. |
| 6,395,733 B1 | 5/2002 | Arnold et al. |
| 6,784,174 B1 | 8/2004 | Cumming |
| 2001/0027197 A1 | 10/2001 | Bridges et al. |
| 2003/0162795 A1 | 8/2003 | Munchhof et al. |
| 2006/0020042 A1 | 1/2006 | McDonald et al. |
| 2007/0099877 A1 | 5/2007 | Cai et al. |
| 2010/0015708 A1 | 1/2010 | Quay et al. |
| 2010/0056548 A1 | 3/2010 | Aicher et al. |
| 2010/0143341 A1 | 6/2010 | Taylor et al. |
| 2010/0247517 A1 | 9/2010 | Austen et al. |
| 2011/0021203 A1 | 1/2011 | Yamada et al. |
| 2011/0212102 A1 | 9/2011 | Lehmann-Lintz et al. |
| 2011/0217311 A1 | 9/2011 | Lehmann-Lintz et al. |
| 2012/0128686 A1 | 5/2012 | Austen et al. |
| 2013/0056914 A1 | 3/2013 | Frankowski et al. |

FOREIGN PATENT DOCUMENTS

| | | | |
|---|---|---|---|
| CA | 2038521 A1 | 9/1991 |
| CH | 408945 A | 3/1966 |
| DE | 248593 A1 | 8/1987 |
| EP | 0447891 A1 | 9/1991 |
| EP | 0452002 A2 | 10/1991 |
| EP | 0682027 A1 | 11/1995 |
| EP | 0729758 A2 | 9/1996 |
| EP | 1724268 A1 | 11/2006 |
| JP | 2005503345 A | 2/2005 |
| WO | 9413677 A1 | 6/1994 |
| WO | 9713771 A1 | 4/1997 |
| WO | 9924440 A1 | 5/1999 |
| WO | 0056738 A1 | 9/2000 |
| WO | 0075145 A1 | 12/2000 |
| WO | 02088138 A1 | 11/2002 |
| WO | 03037362 A2 | 5/2003 |
| WO | 2004037159 A2 | 5/2004 |
| WO | 2004106340 A2 | 12/2004 |
| WO | 2004113347 A1 | 12/2004 |
| WO | 2005010008 A1 | 2/2005 |
| WO | 2005042537 A1 | 5/2005 |
| WO | 2005080377 A1 | 9/2005 |
| WO | 2005117890 A2 | 12/2005 |
| WO | 2006014325 A2 | 2/2006 |

(Continued)

OTHER PUBLICATIONS

Banker, Gilbert S., et al; Modern Pharmaceutics (1996) 3rd Ed. Marcel Dekker, Inc. New York, p. 596.
Baumgartner, A., et al; Uber Thieno-Verbindungen: 14. Mitteilung: Darstellung 4-Aminosubstituierter Thieno[2.3-d]pyrimidyn-6-carbosa bsauurederivate; Institut fur Pharnazeutischer, (1993).
Cheng, C.C., et al; Potential Purine Antagonists. VI. Synthesis of 1-Alkyl- and 1-Aryl-4-substituted Pyrazolo[3,4-d]pyrimidines1,2; Journal of Organic Chemistry, American Chemical Society (1956) vol. 21 pp. 1240-1256.

(Continued)

Primary Examiner — Bruck Kifle
(74) Attorney, Agent, or Firm — Michael P. Morris; Usha R. Patel; Edward S. Lazer

(57) ABSTRACT

The present invention relates to novel pharmaceutical compositions comprising thienopyrimidine compounds. Moreover, the present invention relates to the use of the thienopyrimidine compounds of the invention for the production of pharmaceutical compositions for the prophylaxis and/or treatment of diseases which can be influenced by the inhibition of the kinase activity of Mnk1 and/or Mnk2 (Mnk2a or Mnk2b) and/or variants thereof.

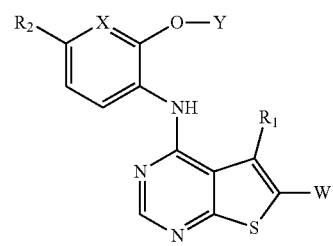

17 Claims, No Drawings

FOREIGN PATENT DOCUMENTS

| | | | |
|---|---|---|---|
| WO | 2006066937 | A2 | 6/2006 |
| WO | 2006094791 | A1 | 9/2006 |
| WO | 2006124874 | A2 | 11/2006 |
| WO | 2006136402 | A1 | 12/2006 |
| WO | 2007056214 | A2 | 5/2007 |
| WO | 2007056215 | A2 | 5/2007 |
| WO | 2007059905 | A2 | 5/2007 |
| WO | 2007081517 | A2 | 7/2007 |
| WO | 2007084815 | A2 | 7/2007 |
| WO | 2007115822 | A1 | 10/2007 |
| WO | 2007147874 | A1 | 12/2007 |
| WO | 2008006547 | A2 | 1/2008 |
| WO | 2008041053 | A2 | 4/2008 |
| WO | 2009065596 | A2 | 5/2009 |
| WO | 2010023181 | A1 | 3/2010 |
| WO | 2011104334 | A1 | 9/2011 |
| WO | 2011104337 | A1 | 9/2011 |
| WO | 2011104338 | A1 | 9/2011 |
| WO | 2011104340 | A1 | 9/2011 |

OTHER PUBLICATIONS

Dörwald, Florencio Zaragoza, et al; Side Reactions in Organic Synthesis: A Guide to Successful Synthesys Design; (2005) Wiley; VCH, Weinheim p. IX of preface, (2004).

http://www.medterms.com/script/main/art.asp?articlekey=12063, last accessed on Aug. 24, 2010.

International Search Report for PCT/EP2006/005980 mailed Nov. 16, 2006.

International Search Report for PCT/EP2007/003186 mailed Jun. 8, 2007.

International Search Report for PCT/EP2007/006109 mailed Dec. 20, 2007.

International Search Report for PCT/EP2009/060876 mailed Nov. 10, 2009.

International Search Report for PCT/EP2011/052810 mailed May 16, 2011.

International Search Report for PCT/EP2011/052811/mailed May 18, 2011.

International Search Report for PCT/EP2011/052813 mailed May 30, 2011.

International Search Report for PCT/EP2008/009880 mailed Jun. 25, 2009.

Jorgensen, Anker, et al; Phosphorus Pentoxide in Organic Synthesis. XX [1]. Synthesis of N-Aryl-7H-pyrrolo[2,3-d]pyrimidin-4-amines; Journal of Heterocyclic Chemistry (1985) pp. 859-863.

Mogensen, Jorgen, et al; Phosphorus Pentoxide in Organic Synthesis: XXXIV*. Synthesis of 3-Arylthieno[2,3-d]pyrimidin-4(3H)-imines and their Rearrangement to N-arylthieno[2,3-d]pyrimidin-4-amines; Chemica Scripta (1988) vol. 28 pp. 195-200.

Munchhof, Michael J., et al; Design and SAR of Thienopyrimidine and Thienopyridine Inhibitors of VEGFR-2 Kinase Activity; Bioorganic & Medicinal Chemistry Letters (2004) vol. 14 pp. 21-24.

Peat, Andrew, J., et al; Novel Pyrazolopyrimidine Derivates as GSK-3 Inhibitors; Bioorganic & Medicinal Chemistry Letters (2004) vol. 14 pp. 2121-2125.

Showalter, H. D. Hollis, et al; Tyrosine Kinase Inhibitors. 16. 6,5,6-Tricyclic Benzothieno[3-,2-d]pyrimidines and Pyrimido[5,4-b]- and -[4,5-b]indoles as Potent Inhibitors of the Epidermal Growth Factor Receptor Tyrosine Kinase; Journal of Medicinal Chemistry (1999) vol. 42 pp. 5464-5474.

Sobolov, Susan B., et al; Selective N-Alkylation of Pyrrolopyrimidines and Indoles by "Transfer of Activation"; Tetrahedron Letters (1998) vol. 39 pp. 5685-5688.

Traxler, Peter, et al; Use of a Pharmacophore Model for the Design of EGF-R Tyrosine Kinase Inhibitors: 4-(Phenylamino)pyrazolo[3,4-d]pyrimidines; Journal of Medicinal Chemistry (1997) vol. 40, No. 22 pp. 3601-3616.

Traxler, Peter, M., et at; 4-(Phenylamino)pyrrolopyrimidines: Potent and Selective, ATP Site Directed Inhibitors of the EGF-Receptor Protein Tyrosine Kinase; Journal of Medicinal Chemistry (1996) vol. 39 pp. 2285-2292.

West, R. A., et al; 2-Alkyl(aryl)-and2,7-Dimethyl-4-substituted Aminopyrrolo [2,3-d]pyrimidines; Journal of Organic Chemistry (1961) vol. 26 pp. 3809-3812.

Wolff, Manfred, E.; Principles and Practice; Burger's Medicinal Chemistry and Drug Discovery (1995) 5ed, vol. 1 pp. 975-977.

Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

SEQUENCE LISTING

```
<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttaggatcc gtatcttctc aaaagttgg                                         29

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgggtcgac tcagagtgct gtgggcgg                                          28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acagggatcc gtgcagaaga aaccagcc                                          28

<210> SEQ ID NO 4
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatggtcgac tcaggcgtgg tctcccacc                                      29

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Thr Lys Ser Gly Ser Thr Thr Lys Asn Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser is phosphorylated

<400> SEQUENCE: 6

Thr Ala Thr Lys Ser Gly Ser Thr Thr Lys Asn Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ser is phosphorylated

<400> SEQUENCE: 7

Cys Thr Ala Thr Lys Ser Gly Ser Thr Thr Lys Asn Arg
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5
```

THIENOPYRIMIDINES FOR PHARMACEUTICAL COMPOSITIONS

SEQUENCE LISTING

The instant application contains a Sequence Listing which has been submitted in ASCII format via EFS-Web and is hereby incorporated by reference in its entirety. Said ASCII copy, created on Jan. 30, 2012, is named 01-2537.txt and is 2,456 bytes in size.

The present invention relates to thienopyrimidine compounds and to novel pharmaceutical compositions comprising thienopyrimidine compounds.

Moreover, the present invention relates to the use of the thienopyrimidine compounds of the invention for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof. Particularly, the present invention relates to the use of the thienopyrimidine compounds of the invention for the production of pharmaceutical compositions for the prophylaxis and/or therapy of metabolic diseases, such as diabetes, hyperlipidemia and obesity, hematopoietic disorders, neurodegenerative diseases, kidney damage, inflammatory disorders, and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease. Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, skin cancer, osteosarcoma, rhabdomyosarcoma, bladder cancer, metastatic cancer, cachexia, or pain.

Certain anti-cancer drugs such as cisplatin are linked to serious side effects such as nephrotoxicity or ototoxicity, which can be dose limiting. Activation of Mnks has been linked to these side effects. In a further embodiment of the present invention, the compounds and compositions of the present invention are useful for the treatment and/or prophylaxis of ear or kidney damage, in particular for the prevention or treatment of ear and kidney drug induced damage.

Furthermore, the present invention relates to the use of thienopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders, such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitrel valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention.

Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, to psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), Poxvirus, Vacciniavirus, Monkeypoxvirus, pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, frontotemporal lobar dementia, spinocerebellar ataxia, dementia with Lewy bodies, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic to inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, is such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of to proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25: 1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

Mnk1 and Mnk2 (including all splice forms) phosphorylate the translation factor eIF4E on Serine 209. Mnk1/2 double knockout mice completely lack phosphorylation on Serine 209, indicating that Mnk kinase are the only kinases able to phosphorylate this site in vivo (Ueda et al., Mol Cell Biol. 2004; 24(15):6539-49). eIF4E is overexpressed in a wide range of human malignancies, and high eIF4E expression is frequently associated with more aggressive disease and poor prognosis. Furthermore, eIF4E to can act as an oncogene when assayed in standard assays for oncogenic activity (e.g. Ruggero et al., Nat. Med. 2004 May; 10(5):484-6). eIF4E excerts its oncogenic activity by stimulating the translation of oncogenes such as c-myc and cyclinD1 (Culjkovic et al., J. Cell Biol. 2006; 175(3):415-26), by increasing the expression of pro-survival factors such as MCP-1 (Wendel et al., Genes Dev. 2007; 21(24):3232-7) and by positively regulating pathways of drug resistance (Wendel et al., Nature 2004; 428(6980):332-7; Graff et el., Cancer Res. 2008; 68(3): 631-4; De Benedetti and Graff, Oncogene 2004; 23(18):3189-99; Barnhart and Simon, J Clin Invest. 2007; 117(9):2385-8). Suppression of eIF4E expression by antisense oligonucleotides has shown promise in preclinical experiments with human tumor cells (Graff et al., J Clin Invest. 2007; 117(9):2638-48). It has been shown that phosphorylation on Ser209 is strictly required for the oncogenic activity of eIF4E in vitro and in vivo (Topisirovic et al., Cancer Res. 2004; 64(23):8639-42; Wendel et al., Genes Dev. 2007; 21(24):3232-7). Thus, inhibition of Mnk1 and Mnk2 is expected to have beneficial effects in human malignancies.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

Further inhibitors of Mnk have been described. See for example Applicants patent applications WO 06/066937, describing pyrazolopyrimidine compounds, WO 06/136402 describing certain thienopyrimidine compounds, WO 07/115,822 describing further thienopyrimidine compounds with modified core ring, and WO 08/006,547 describing pyrrolopyrimidines as inhibitors of Mnk kinases.

The problem underlying the present invention is to provide potent and selective Mnk1 and/or Mnk2 inhibitors which may effectively and safely be used for the treatment of metabolic diseases, inflammatory diseases, cancer, neurodegenerative diseases and their consecutive complication and disorders.

It has now been surprisingly found that certain thienopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

In contrast to the thienopyrimidine compounds known in the art, for example, the compounds disclosed in the Applicants patent applications WO 06/136402 and WO 2007/115822, the thienopyrimidine compounds of the present invention provide several advantages, namely, enhanced solubility, the possibility to form stable salts, improved metabolic stability, enhanced or retained activity in biochemical or cellular Mnk activity assays and enhanced or retained selectivity against other kinases.

The thienopyrimidine compounds disclosed in WO 06/136402 and WO 07/115,822 exhibit high activity in Mnk enzyme assays and extremely high selectivity, however they show a very low solubility and are in most cases metabolic unstable resulting in undesired pharmacokinetic properties.

It has been surprisingly found that by the introduction of a polar group at the W-position in the compounds of general formula (I) below leads to surprising substantial metabolic stabilization, rendering the thienopyrimidines of the present invention useful for in vivo pharmacological applications.

Moreover, compounds described in this application also show improved solubility, have strong inhibitory potency in biochemical and cellular assays and are highly selective, resulting in overall greatly improved pharmacological properties.

If not specified otherwise, any alkyl moiety mentioned in this application may be straight-chained or branched.

Thienopyrimidine compounds of the present invention are compounds of the general formula (I):

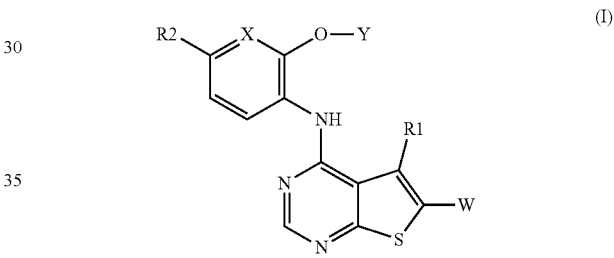

(I)

wherein

X is selected from CH or N;

$R_2$ is selected from H, CN, $CF_3$, $CON(R_4)_2$, O—$C_{1-8}$ alkyl optionally substituted by $R_3$; $C_{3-10}$ heterocyclyl comprising at least one heteroatom selected from N, S and O; $C_{5-10}$ heteroaryl comprising at least one heteroatom selected from N, S and O; $C_{1-8}$ alkyl optionally substituted by $R_6$ and when X is CH, may also be F, Cl, $SO_2NH_2$;

Y is selected from straight chain or branched $C_{1-8}$ alkyl, optionally substituted by one or more of $R_3$, $C_{3-8}$ cycloalkyl, optionally substituted by one or more of $R_9$; or heterocyclyl systems selected from any one of the formulae:

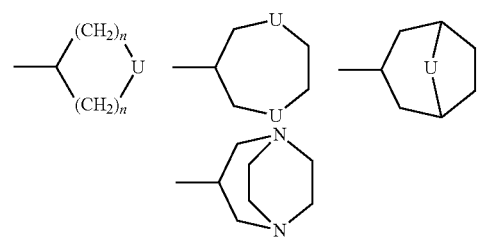

optionally substituted by one or more of $R_9$;

wherein n is 1 to 3 and U is O or $NR_5$;

$R_1$ is selected from Cl; or $C_{1-8}$ alkyl, optionally substituted by $N(R_4)_2$ or F;

$R_3$ is selected from OH, $OR_4$ and $N(R_4)_2$ from the second carbon atom onwards; F; $CO_2H$; $CON(R_4)_2$; $SO_2N(R_4)_2$; $C_{3-10}$ heterocyclyl comprising at least one heteroatom selected from N, S and O; or $C_{6-10}$ heteroaryl comprising at least one heteroatom selected from N, S and O;

$R_4$ is selected from H or $C_{1-8}$ alkyl;

$R_5$ is selected from H; $C_{1-8}$ alkyl; $C_{2-8}$ alkenyl; $C_{3-10}$ cycloalkyl; $C_{3-10}$ heterocyclyl comprising at least one heteroatom selected from N, S and O; $C_{6-10}$ heteroaryl comprising at least one heteroatom selected from N, S and O; $CONH(CH_2)_m R_6$, $(CH_2)_m R_6$; $CO(CH_2)_m R_6$; or $SO_2(CH_2)_m R_6$; wherein m is 1-4;

$R_6$ is selected from H; OH; $OR_4$; $N(R_4)_2$; F; $CO_2H$; $CON(R_4)_2$; $SO_2N(R_4)_2$; $C_{3-10}$ heterocyclyl comprising at least one heteroatom selected from N, S and O; or $C_{5-10}$ heteroaryl comprising at least one heteroatom selected from N, S and O;

W is selected from F; Cl; Br; I; $C_{1-8}$ alkyl substituted by $R_6$; —$(CH_2)_{1-2}NR_7R_8$; —$CONR_7R_8$; —$C(=NR_7)NR_7R_8$, —$CO_2R_7$; —$SO_2NR_7R_8$; or W together with $R_1$ can form a five to seven membered heterocyclic ring comprising at least one heteroatom selected from N, S and O;

$R_7$ is selected from H or $C_{1-8}$ alkyl;

$R_8$ is selected from H; $C_{1-8}$ alkyl optionally substituted by $R_3$; $C_{3-10}$ heterocyclyl comprising at least one heteroatom selected from N, S and O; or $C_{5-10}$ heteroaryl comprising at least one heteroatom selected from N, S and O;

$R_9$ is selected from OH, $OR_4$ and $N(R_4)_2$ on any carbon atom other than one attached to O or N; F; $CO_2H$; $CON(R_4)_2$; $SO_2N(R_4)_2$; $(CH_2)_m OR_4$; $(CH_2)_m N(R_4)_2$; $C_{3-10}$ heterocyclyl comprising at least one heteroatom selected from N, S and O; or $C_{5-10}$ heteroaryl comprising at least one heteroatom selected from N, S and O;

or a metabolite, prodrug or a pharmaceutically acceptable salt thereof.

Compounds wherein $R_1$ is $C_{1-8}$ alkyl, optionally substituted by $N(R_4)_2$ are preferred.

Moreover, compounds as defined above, wherein Y is a heterocyclyl system selected from any one of the formulae:

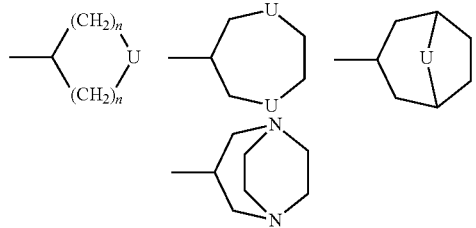

optionally substituted by one or more of $R_9$, wherein n is 1 to 3 and U is $NR_5$ are preferred.

Also preferred are compounds as defined above, wherein W together with $R_1$ form a ring selected from the formulae (II)-(VI)

(II)

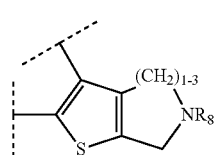

(III)

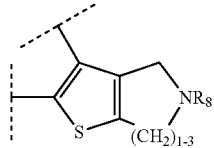

(IV)

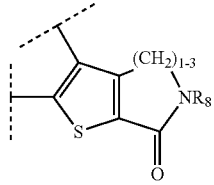

(V)

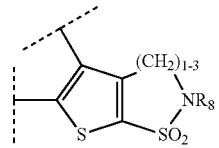

(VI)

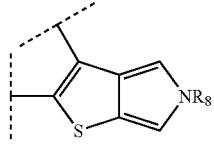

and X is selected from CH or N, more preferably X is N.

In one aspect, the present invention relates to compounds as defined above wherein W is selected from —$CO_2R_7$; $C_{1-8}$ alkyl substituted by H, OH, $OR_4$, F, $CO_2H$, or $C_{3-10}$ heterocyclyl comprising at least one heteroatom selected from S and O; and wherein W is preferably —$CO_2R_7$.

In another aspect, to present invention relates to compounds wherein W is selected from —$(CH_2)_{1-2}NR_7R_8$; —$CONR_7R_8$; —$C(=NR_7)NR_7R_8$, —$SO_2NR_7R_8$; $C_{1-8}$ alkyl substituted by $N(R_4)_2$, $CON(R_4)_2$, $SO_2N(R_4)_2$, or $C_{3-10}$ heterocyclyl comprising at least one N atom and optionally one or more additional heteroatoms selected from N, S and O; or W together with $R_1$ form a ring selected from the formulae (II)-(VI):

(II)

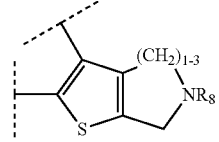

(III)

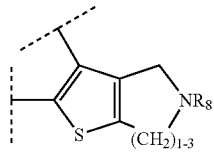

(IV)

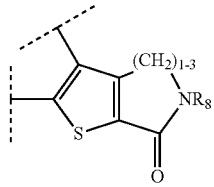

-continued

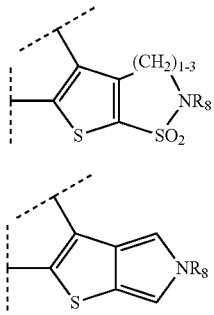
(V)

(VI)

In this second aspect W is preferably —CONR₇R₈.

In more preferred compounds of the present invention Y is selected from

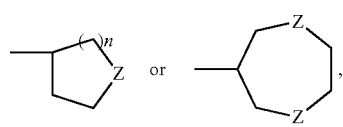

optionally substituted by one or more of R₉; wherein Z is NR₄ or O and n is 1 or 2, even more preferred is Z is O.

Compounds as defined above wherein Y is a heterocyclyl of the formula:

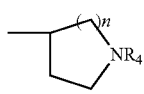

optionally substituted by one or more of R₉; wherein n 1 or 2; and W is —CONR₇R₈ are particularly preferred.

Also compounds as defined above wherein Y is a heterocyclyl of the formula:

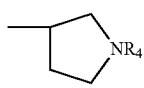

optionally substituted by one or more of R₉;
W is —CONR₇R₈,
and X is N are particularly preferred.

In another preferred embodiment Y is a heterocyclyl of the formula:

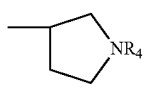

optionally substituted by one or more of R₉;
W is —CONR₇R₈,
and X is CH.

Also preferred are compounds as defined above wherein Y is a heterocyclyl of the formula:

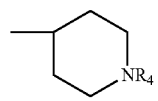

optionally substituted by one or more of R₉;
W is —CONR₇R₈,
and X is N.

In another preferred embodiment Y is a heterocyclyl of the formula:

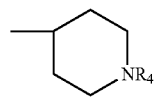

optionally substituted by one or more of R₉;
W is —CONR₇R₈,
and X is CH.

Furthermore, the invention concerns compounds of the general formula (I)

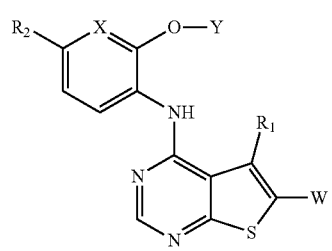
(I)

wherein
X is selected from CH or N;
R₂ is selected from H, CN, CF₃, CON(R₄)₂, O—C₁₋₈ alkyl optionally substituted by R₃; C₃₋₁₀ heterocyclyl comprising at least one heteroatom selected from N, S and O; C₅₋₁₀ heteroaryl comprising at least one heteroatom selected from N, S and O; and C₁₋₈ alkyl optionally substituted by R₆; and when X is CH, R₂ may also be F, Cl, SO₂NH₂;
Y is selected from straight chain or branched C₁₋₈ alkyl, optionally substituted by one or more of R₃; C₃₋₈ cycloalkyl, optionally substituted by one or more of R₉; and heterocyclyl systems selected from any one of the formulae:

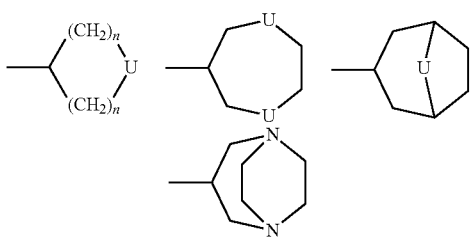

optionally substituted by one or more of R₉,
wherein n is independently 1 to 3 and U is independently O or NR₅;
R₁ is selected from H; Cl; and C₁₋₈ alkyl, optionally substituted by N(R₄)₂ or F;

$R_3$ is selected from OH, $OR_4$ and $N(R_4)_2$ from the second carbon atom of the alkyl chain to which $R_3$ is attached onwards; F; $CO_2H$; $CON(R_4)_2$; $SO_2N(R_4)_2$; $C_{3-10}$ heterocyclyl comprising at least one heteroatom selected from N, S and O, wherein the nitrogen atom may be substituted by H or $C_{1-3}$ alkyl; and $C_{5-10}$ heteroaryl comprising at least one heteroatom selected from N, S and O;

$R_4$ is selected from H and $C_{1-8}$ alkyl;

$R_5$ is selected from H; $C_{1-8}$ alkyl; $C_{2-8}$ alkenyl; $C_{3-10}$ cycloalkyl; $C_{3-10}$ heterocyclyl comprising at least one heteroatom selected from N, S and O; $C_{5-10}$ heteroaryl comprising at least one heteroatom selected from N, S and O; $COR_6$; $CO_2R_4$; $CONH(CH_2)_mR_6$, $(CH_2)_mR_6$; $CO(CH_2)_mR_6$; $(CH_2)_mC(O)R_6$; $SO_2R_4$; and $SO_2(CH_2)_mR_6$; wherein m is 1-4;

$R_6$ is selected from H; OH; $OR_4$; $OC(O)R_4$; $N(R_4)_2$; F; $CO_2H$; $CON(R_4)_2$; $SO_2N(R_4)_2$; $C_{3-10}$ heterocyclyl comprising at least one heteroatom selected from N, S and O; and $C_{5-10}$ heteroaryl comprising at least one heteroatom selected from N, S and O, which is optionally substituted by $C_{1-3}$ alkyl or $N(R_4)_2$;

W is selected from F; Cl; Br; I; CN; —$(CH_2)_{1-2}NR_7R_8$; —$C(S)NH_2$; —$CONR_7R_8$; —$C(=NR_7)NR_7R_8$, —$CO_2R_7$; and —$SO_2NR_7R_8$;

or W together with $R_1$ can form a five to seven membered heterocyclic ring comprising at least one heteroatom selected from N, S and O, wherein the nitrogen atom may be substituted by H, —C(O)—O—$C_{1-4}$ alkyl, —CO—$(CH_2)_{1-2}$—$NH_2$, —CO—$(CH_2)_{1-2}$—$NH(C_{1-3}$ alkyl) or —CO—$(CH_2)_{1-2}$—$N(C_{1-3}$ alkyl)$_2$;

$R_7$ is selected from H and $C_{1-8}$ alkyl;

$R_8$ is selected from H; $C_{1-8}$ alkyl optionally substituted by $R_3$; $C_{3-10}$ heterocyclyl comprising at least one heteroatom selected from N, S and O, optionally substituted by $C_{1-3}$ alkyl; and $C_{5-10}$ heteroaryl comprising at least one heteroatom selected from N, S and O;

$R_9$ is selected from OH, $OR_4$, $N(R_4)_2$, $N(R_4)COR_4$, $NR_4SO_2R_4$ and $N(R_4)$—$(CH_2)_m$—$R_4$ on any carbon atom other than one attached to O or N; F; $CO_2H$; $CON(R_4)_2$; $SO_2N(R_4)_2$; $SO_2R_4$; $(CH_2)_mOR_4$; $(CH_2)_mN(R_4)_2$; $C_{3-10}$ heterocyclyl comprising at least one heteroatom selected from N, S and O; and $C_{5-10}$ heteroaryl comprising at least one heteroatom selected from N, S and O;

with the proviso that the compound ethyl 4-(2-methoxyphenylamino)-5-methylthieno[2,3-d]pyrimidine-6-carboxylate is excluded;

or a tautomer, metabolite, prodrug or a pharmaceutically acceptable salt thereof.

Preferred are those compounds of general formula (I), wherein

X is CH or N;

$R_2$ is H, CN, $CF_3$, $CON(R_4)_2$, O—$C_{1-4}$ alkyl optionally substituted by $C_{1-3}$ alkoxy; or furanyl; and when X is CH, $R_2$ may also be F, Cl;

Y is straight chain or branched $C_{1-4}$ alkyl, optionally substituted by $R_3$; $C_{3-8}$ cycloalkyl, optionally substituted by one or two $R_9$; or a heterocyclyl system selected from any one of the formulae:

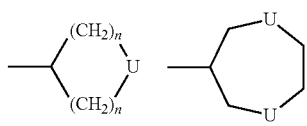

optionally substituted by one or more of $R_9$, wherein n is independently 1 to 3 and U is independently O or $NR_5$;

$R_1$ is H; or $C_{1-3}$ alkyl;

$R_3$ is OH, $OR_4$ and $N(R_4)_2$ from the second carbon atom of the alkyl chain to which $R_3$ is attached onwards; or $C_{5-7}$ heterocyclyl comprising one or two heteroatoms selected from N, S and O, wherein the nitrogen atom may be substituted by H or $C_{1-3}$ alkyl;

$R_4$ is H or $C_{1-4}$ alkyl;

$R_5$ is H; $C_{1-4}$ alkyl; $COR_6$; $CO_2R_4$; $SO_2R_4$; C(O)—$(CH_2)_m$—$R_6$; $(CH_2)_mC(O)R_6$; or $(CH_2)_mR_6$; wherein m is 1-4;

$R_6$ is H; OH; $OR_4$; $OC(O)R_4$; $N(R_4)_2$; F; $CO_2H$; $CON(R_4)_2$; $SO_2N(R_4)_2$; $C_{3-10}$ heterocyclyl comprising at least one heteroatom selected from N, S and O; or $C_{5-10}$ heteroaryl comprising at least one heteroatom selected from N, S and O, which is optionally substituted by $C_{1-3}$ alkyl or $N(R_4)_2$;

W is F; Cl; Br; CN; —$C(S)NH_2$; —$CONR_7R_8$; —$C(=NR_7)NR_7R_8$; —$CO_2R_7$; or —$SO_2NR_7R_8$;

or W together with $R_1$ can form a five to seven membered heterocyclic ring comprising at least one heteroatom selected from N, S and O, wherein the nitrogen atom may be substituted by H, —C(O)—O—$C_{1-4}$ alkyl, —CO—$(CH_2)_{1-2}$—$NH_2$, —CO—$(CH_2)_{1-2}$—$NH(C_{1-3}$ alkyl) or —CO—$(CH_2)_{1-2}$—$N(C_{1-3}$ alkyl)$_2$;

$R_7$ is H or $C_{1-3}$ alkyl;

$R_8$ is H; $C_{1-4}$ alkyl optionally substituted by $R_3$, $C_{3-10}$ heterocyclyl comprising at least one heteroatom selected from N, S and O, optionally substituted by $C_{1-3}$ alkyl; or $C_{5-10}$ heteroaryl comprising at least one heteroatom selected from N, S and O;

$R_9$ is OH, $OR_4$, $N(R_4)_2$, $N(R_4)COR_4$, $NR_4SO_2R_4$ or $N(R^4)$—$(CH_2)_m$—$R^4$ on any carbon atom other than one attached to O or N; $SO_2R_4$; —$(CH_2)_m$—$OR_4$; or $C_{3-10}$ heterocyclyl comprising at least one heteroatom selected from N, S and O;

with the proviso that the compound ethyl 4-(2-methoxyphenylamino)-5-methylthieno[2,3-d]pyrimidine-6-carboxylate is excluded;

or a tautomer, ester, amide or a pharmaceutically acceptable salt thereof.

More preferred are those compound of the general formula (I), wherein

X is CH or N;

$R_2$ is H, CN, $CF_3$, or $CONH_2$; and when X is CH, $R_2$ may also be F, Cl;

Y is $C_{3-8}$ cycloalkyl, optionally substituted by $N(R_4)COR_4$, $SO_2R_4$, —$(CH_2)_m$—$OR_4$ or morpholino; or a heterocyclyl system selected from any one of the formulae:

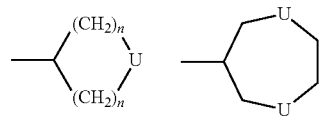

wherein n is independently 1 to 3 and U is independently O or $NR_5$;

$R_1$ is H; or $C_{1-3}$ alkyl;

$R_3$ is OH, $OR_4$, $N(R_4)_2$; or a heterocycle selected from morpholinyl or pyrrolidinyl, wherein the nitrogen atom or the heterocycle may be substituted by $C_{1-3}$ alkyl;

$R_4$ H or $C_{1-4}$ alkyl;

$R_5$ is H; $COR_6$; $CO_2R_4$; $SO_2R_4$; —C(O)—$(CH_2)_m$—$R_6$; $(CH_2)_mC(O)R_6$; or $(CH_2)_mR_6$; wherein m is 1 to 4;

$R_6$ is H; OH; $OR_4$; $OC(O)R_4$; $N(R_4)_2$; F; $CO_2H$; $CON(R_4)_2$; $SO_2N(R_4)_2$; morpholinyl; or a heteroaryl group selected from pyrrolyl, pyrazolyl, imidazolyl, thiazolyl and pyridinyl, each optionally substituted by methyl or $NH_2$;

W is F; Cl; Br; CN; —C(S)NH_2; —CONR_7R_8; —C(=NR_7)NR_7R_8; —CO_2R_7; or —SO_2NR_7R_8;

$R_7$ is H or $C_{1-3}$ alkyl;

$R_8$ is H; $C_{1-4}$ alkyl; $C_{2-4}$ alkyl substituted terminally by $R_3$, or piperidinyl optionally substituted by $C_{1-3}$ alkyl;

or a tautomer, ester, amide or a pharmaceutically acceptable salt thereof.

An aspect of the invention concerns those compounds of general formula (I), wherein $R_1$ is methyl,
with the proviso that the compound ethyl 4-(2-methoxyphenylamino)-5-methylthieno[2,3-d]pyrimidine-6-carboxylate is excluded;

or a tautomer, ester, amide or a pharmaceutically acceptable salt thereof.

A second aspect of the invention concerns those compounds of general formula (I),
wherein Y is a heterocyclyl system selected from any one of the formulae:

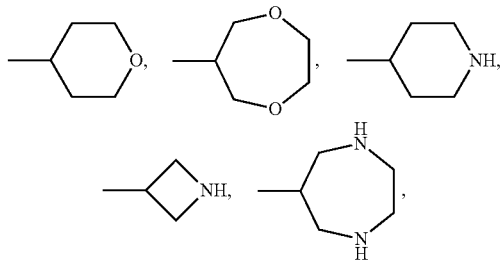

wherein the nitrogen atoms are optionally independently substituted by $C_{1-3}$ alkyl, —C(O)OC_{1-4} alkyl, —C(O)C_{1-4} alkyl, —C(O)—(CH_2)_q—OC_{1-4} alkyl, —C(O)—(CH_2)_q—N(CH_3)_2, —SO_2C_{1-3} alkyl, —(CH_2)_p—NH_2, —(CH_2)_p—OH, —(CH_2)_p—OC(O)C_{1-3} alkyl, —(CH_2)_qC(O)NH_2, —(CH_2)_qC(O)N(CH_3)_2; —CH_2-heteroaryl, which is optionally substituted in the heteroaryl moiety by $NH_2$ and wherein the heteroaryl moiety is selected from pyrrolyl, pyrazolyl, imidazolyl, thiazolyl and pyridinyl; —C(O)-pyrrolyl, which is optionally substituted by $C_{1-3}$ alkyl; or —CH_2—C(O)-morpholino, wherein q is 1 to 3 and p is 2 or 3, or a tautomer, ester, amide or a pharmaceutically acceptable salt thereof.

A third aspect of the invention concerns those compounds of general formula (I),
wherein W together with $R_1$ and the thieno moiety of the core structure depicted in formula (I) form a ring selected from the formulae (II)-(VI)

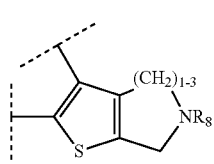

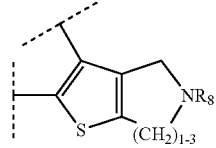

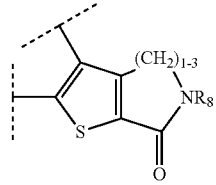

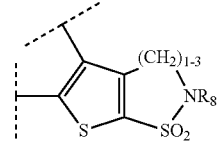

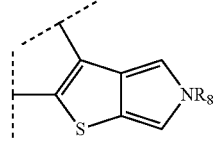

wherein $R_8$ is H, —C(O)OC_{1-4} alkyl or —C(O)—CH_2—N(CH_3)_2, or a tautomer, ester, amide or a pharmaceutically acceptable salt thereof.

A fourth aspect of the invention concerns those compounds of general formula (I),
wherein W together with $R_1$ and the thieno moiety of the core structure depicted in formula (I) form a ring of formula (II),
wherein $R_8$ is H, —C(O)OC_{1-4} alkyl or —C(O)—CH_2—N(CH_3)_2, or a tautomer, ester, amide or a pharmaceutically acceptable salt thereof.

A fifth aspect of the invention concerns those compounds of general formula (I),
wherein W is selected from —CONR_7R_8 or —CO_2R_7,
wherein $R_7$ is H or methyl and
$R_8$ is $C_{1-4}$ alkyl optionally substituted by OH, —O—C_{1-3} alkyl, —NH_2, —NH(C_{1-3} alkyl), —N(C_{1-3} alkyl)_2, morpholino, pyrrolidinyl or N-methyl-pyrrolidinyl, or a tautomer, ester, amide or a pharmaceutically acceptable salt thereof.

A sixth aspect of the invention concerns those compounds of general formula (I),
wherein W is —C(O)NH_2 or —C(O)NHR_8,
wherein $R_8$ is as previously defined, or a tautomer, ester, amide or a pharmaceutically acceptable salt thereof.

Another aspect of the invention concerns those compounds of general formula (I),
wherein
X is CH and
$R_2$ is F, Cl, CN or $C(O)NH_2$,
or a tautomer, ester, amide or a pharmaceutically acceptable salt thereof.

Still another aspect of the invention concerns those compounds of general formula (I), wherein
X is N and
$R_2$ is H or CN,
or a tautomer, ester, amide or a pharmaceutically acceptable salt thereof.
Particularly preferred compounds are selected from:
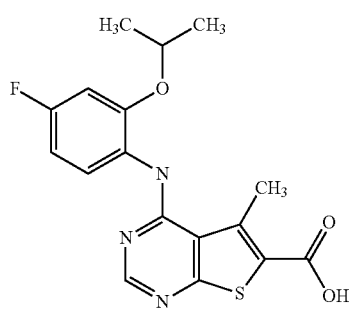
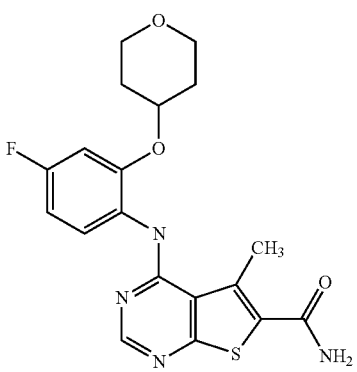
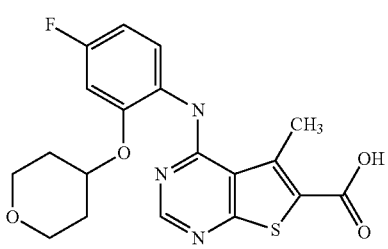
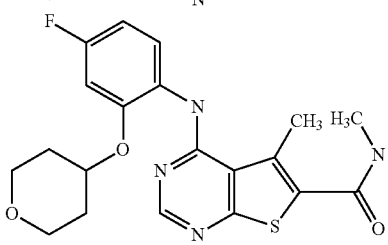
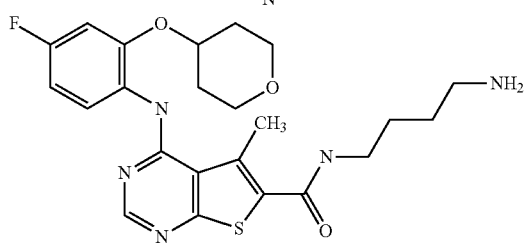
-continued
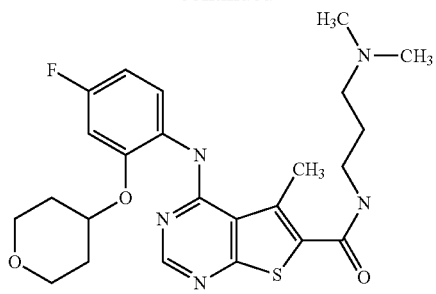
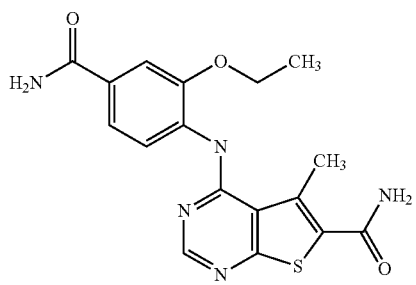
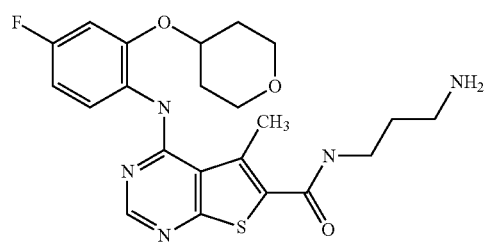
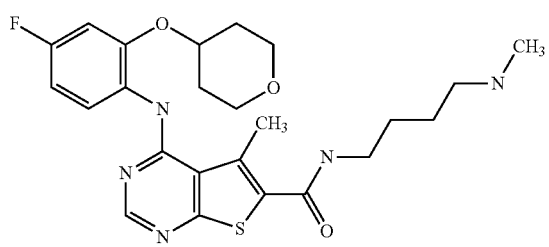
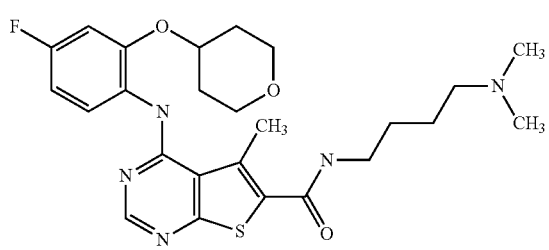
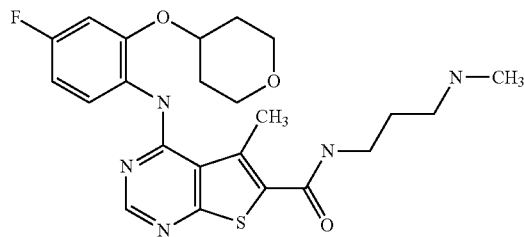

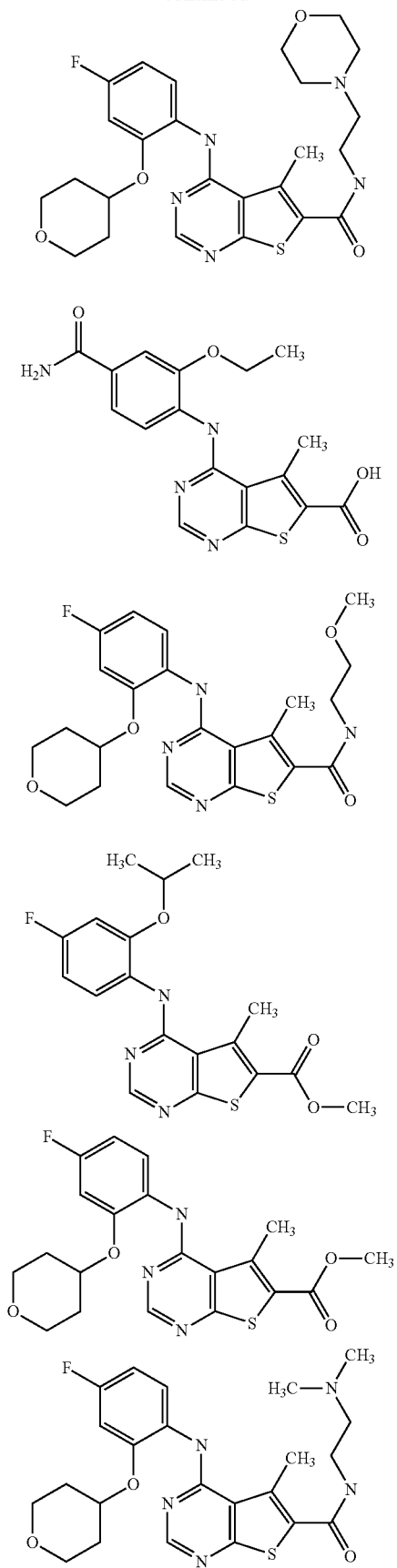
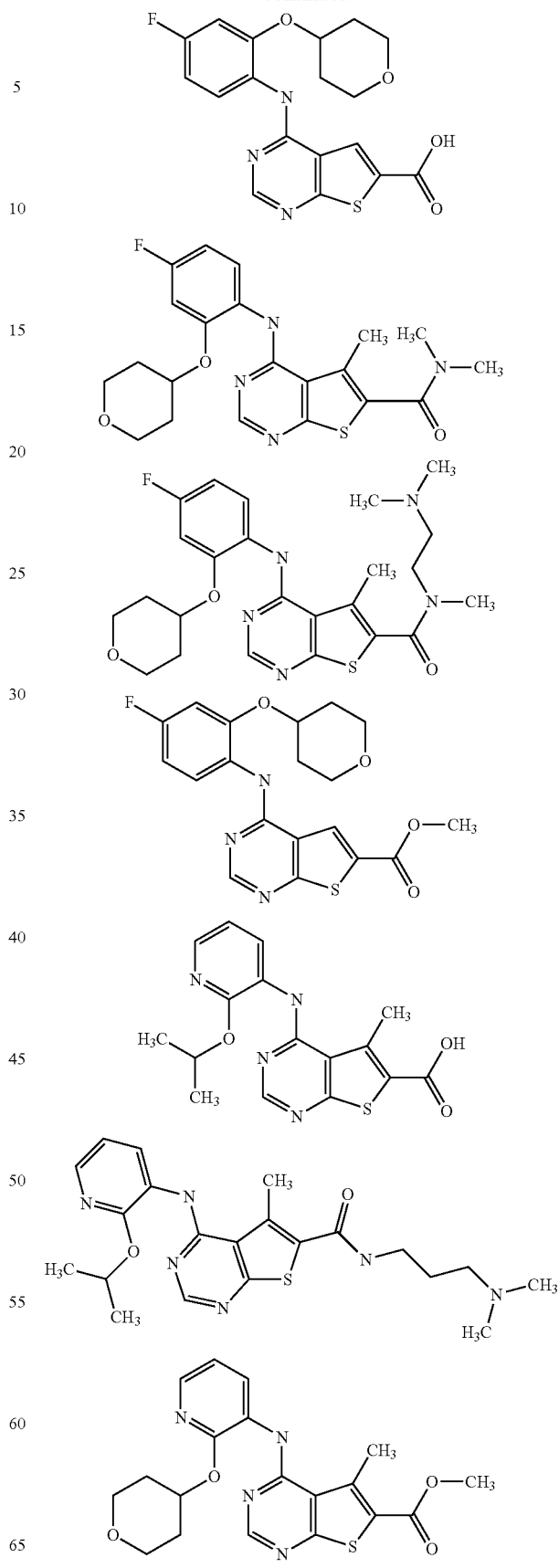

| 21 | 22 |
|---|---|
| -continued | -continued |
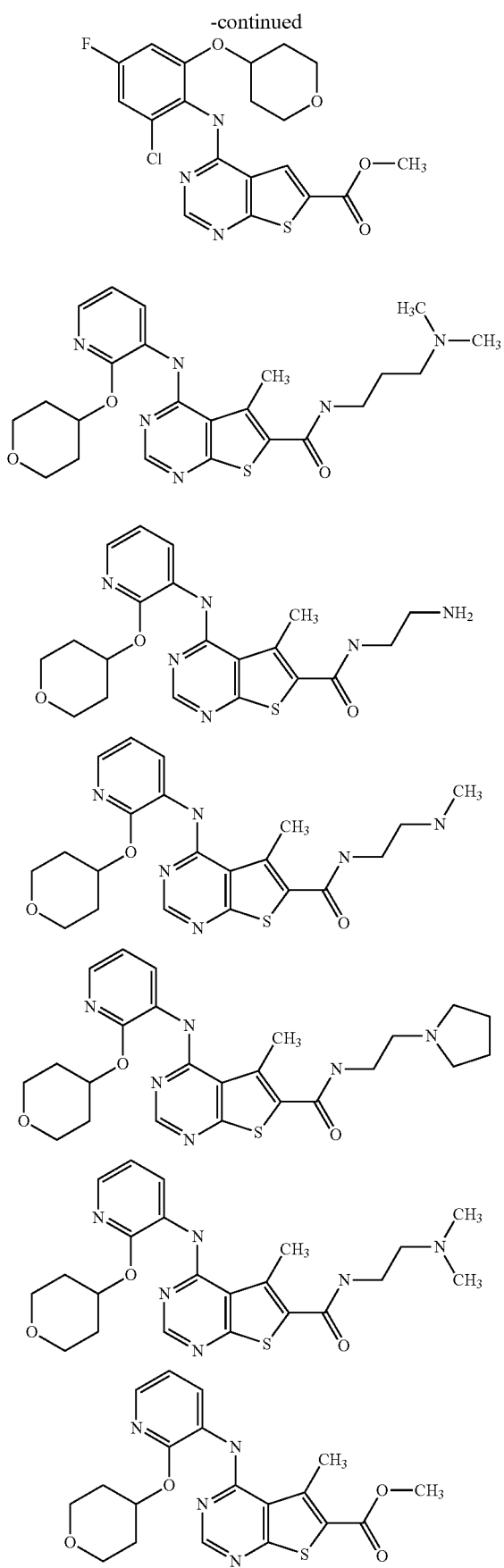
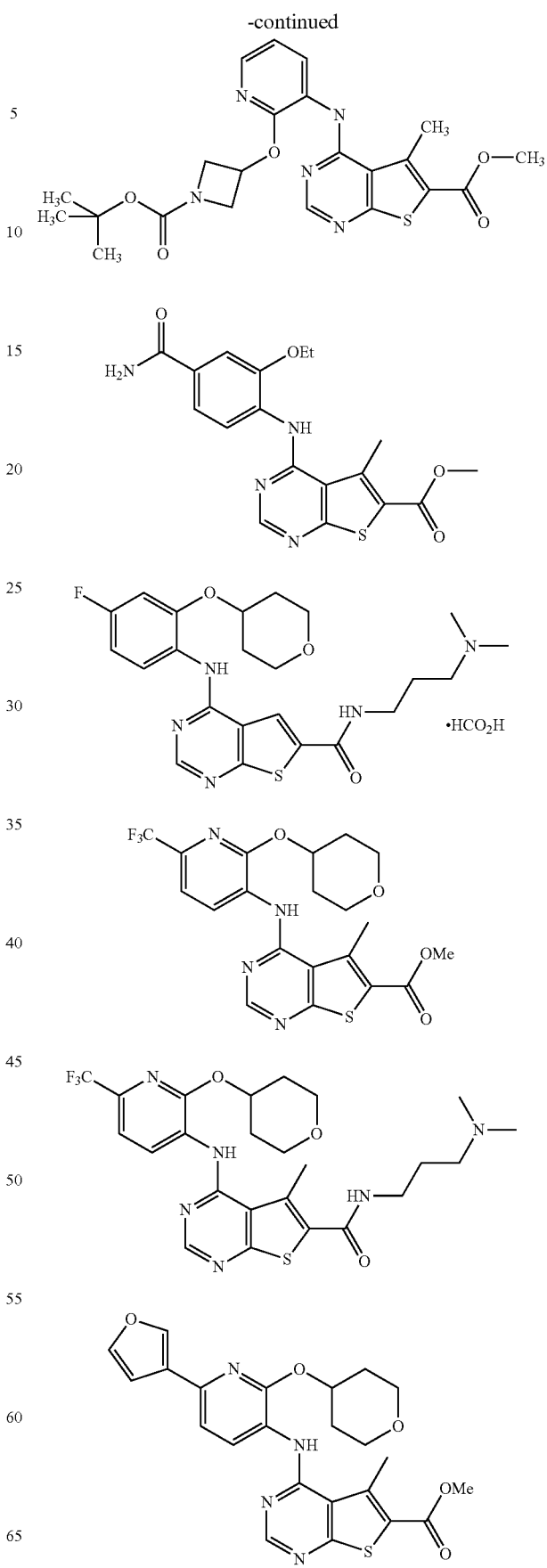

-continued
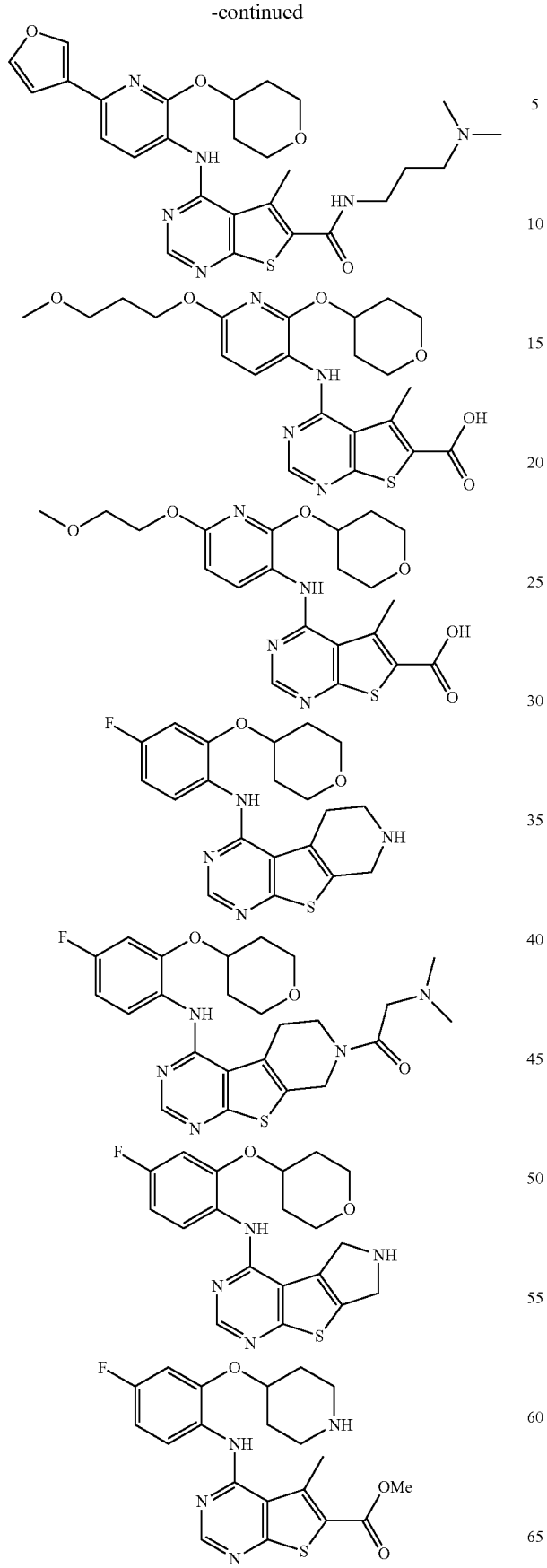
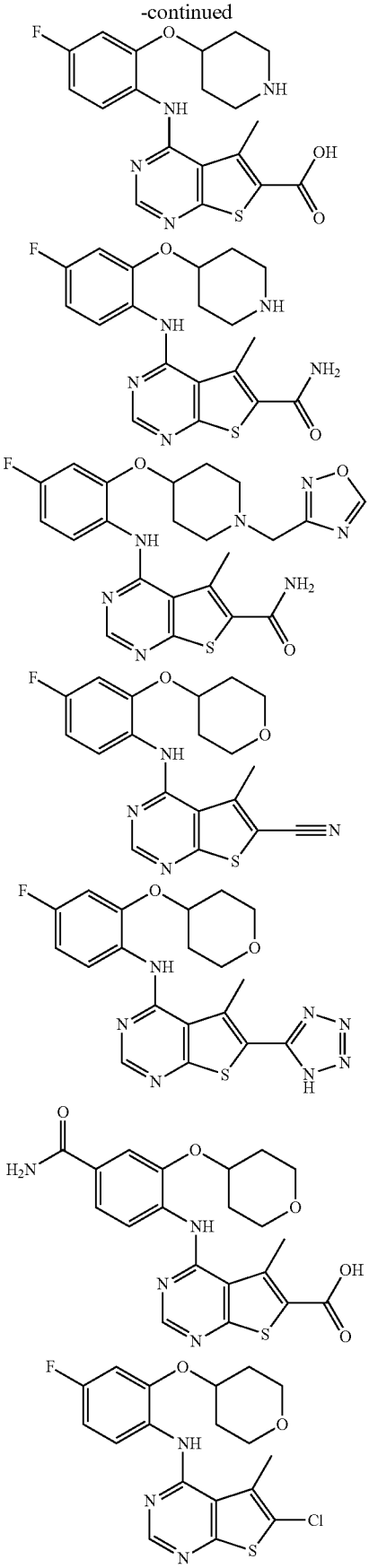

-continued
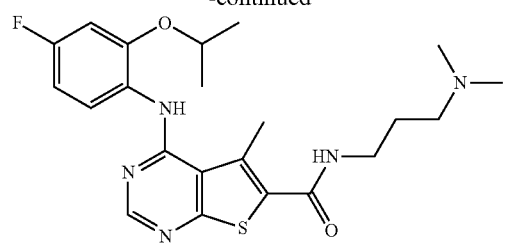
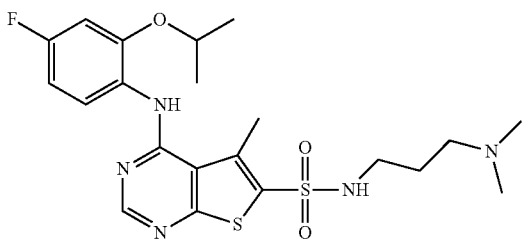
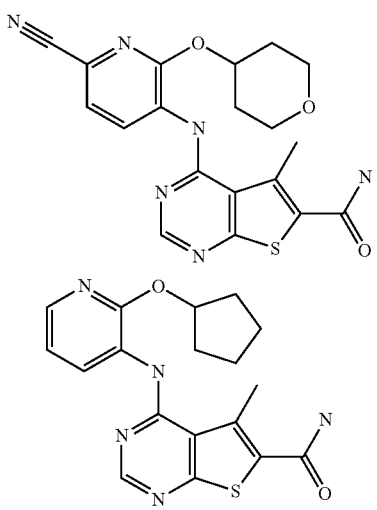
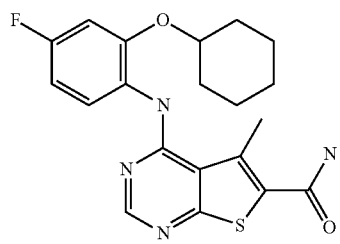
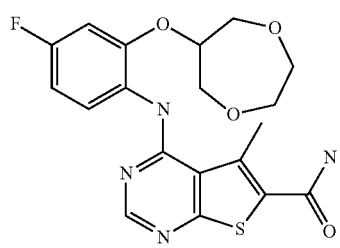
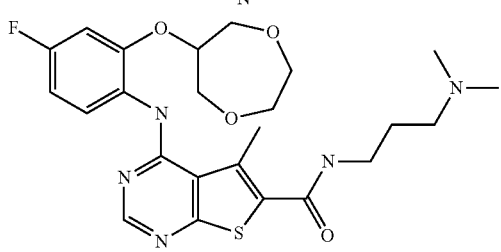
-continued
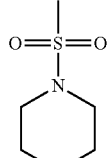
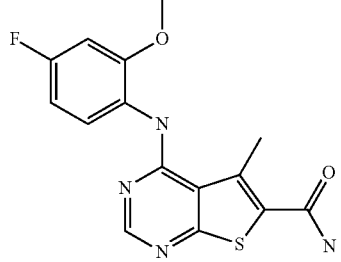
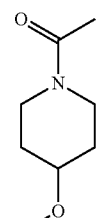
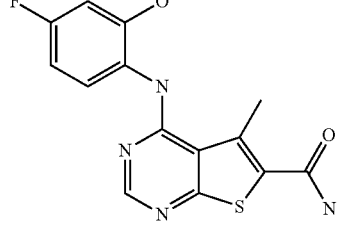
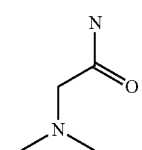
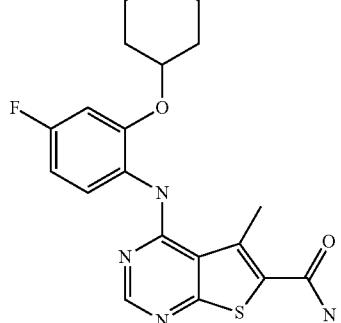

27
-continued
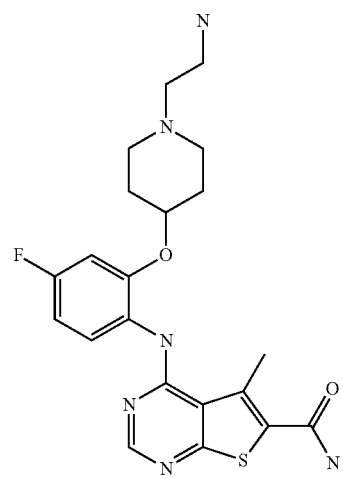
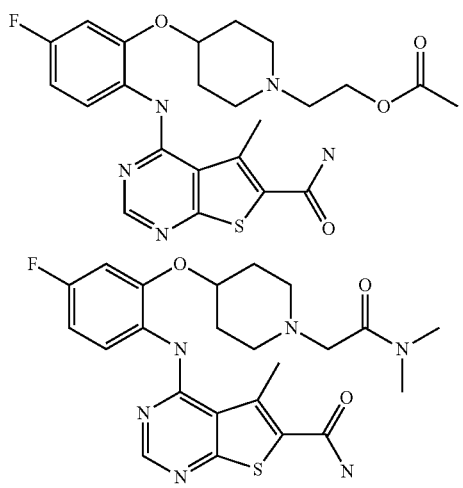
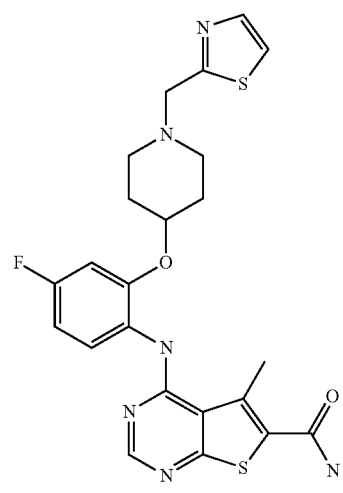
28
-continued
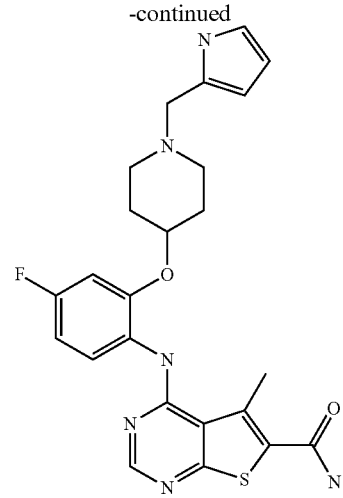
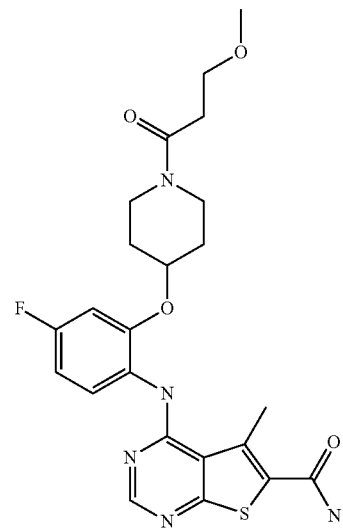
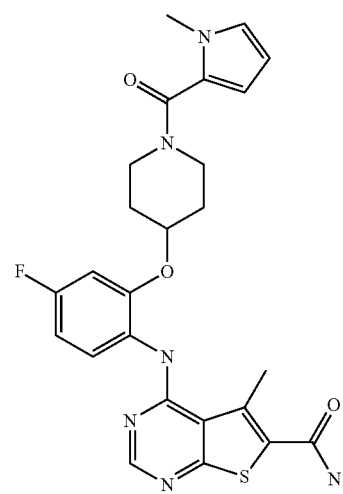

29
-continued

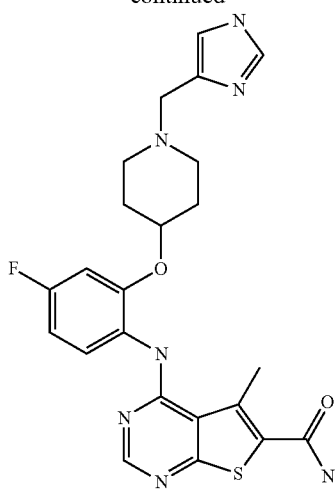

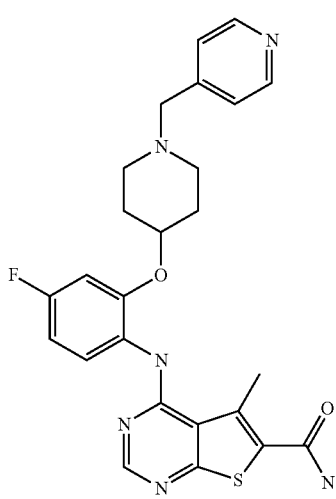

30
-continued

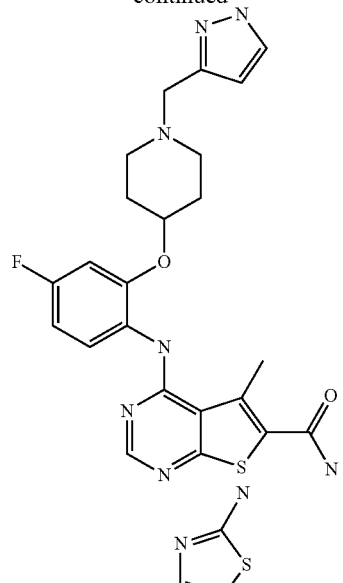

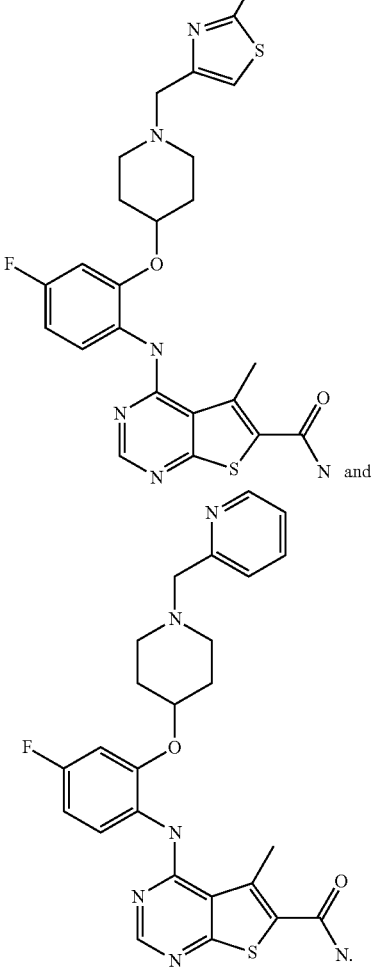

Typical methods of preparing the compounds of the invention are described below in the experimental section.

The potent inhibitory effect of the compounds of the invention may be determined by in vitro enzyme assays as described in the Examples in more detail.

Pharmaceutically acceptable salts of the compounds of the invention of formula (I) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate, cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Compounds of the formula (1) can be present as tautomers. The present invention comprises all tautomeric forms. Furthermore, the present invention also comprises all stereoisomers of the compounds according to the invention, including its enantiomers and diastereomers. Individual stereoisomers of the compounds according to the invention can be substantially present pure of other isomers, in admixture thereof or as racemates or as selected stereoisomers.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

As used herein the term "$C_{3-10}$ cycloalkyl" or "$C_{3-8}$ cycloalkyl" refers to mono- or polycyclic carbocyclic alkyl substituent or group having 3 to 10 or 3 to 8 ring atoms respectively, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-8}$ alkyl" as used herein alone or in combination with other terms such as in alkoxy refers to a $C_{1-8}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-8}$ alkyl" also includes an alkyl group which may contain oxygen in the chain and may be substituted with halogen to form an ether or halogenated ether group.

The term "$C_{2-8}$ alkenyl" by itself or as part of another group refers to a straight or branched alkenyl group of 2 to 8 carbons, preferably 2 to 6 carbons, in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a thienopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas, biguanides, DPP-IV inhibitors, SGLT2 inhibitors, 11β-HSD inhibitors, glucokinase activators, AMPK activators, GIp-1 receptor agonists, GIP receptor agonists, DGAT inhibitors, PPARgamma agonists, PPARdelta agonists, and other antidiabetics derived from thiazolidinediones, lipid lowering agents such as statines, fibrates, ion exchange resins nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, an antineoplastic agent, a mTor inhibitor, a Tyrosine kinase inhibitor, antibodies or fragments thereof against cytokines and soluble parts (fragments) of cytokine receptors.

More particularly preferred are compounds such as human NPH insulin, human lente or ultralente insulin, insulin Lispro, insulin Aspart, insulin Glulisine, insulin detemir or insulin Glargine, metformin, phenformin, acarbose, miglitol, voglibose, pioglitazone, rosiglizatone, rivoglitazone, aleglitazar, alogliptin, saxagliptin, sitagliptin, vildagliptin, exenatide, liraglutide, albiglutide, pramlintide, carbutamide, chlorpropamide, glibenclamide (glyburide), gliclazide, glimepiride, glipizide, gliquidone, tolazamide, tolbutamide, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, docetaxel, paclitaxel, carboplatin, cisplatin, oxaliplatin, BBR3464, satraplatin, busulfan, treosulfan, procarbazine, dacarbazine, temozolomide, chlorambucil, chlormethine, cyclophosphamide, ifosfamide, melphalan, bendamustine, uramustine, ThioTEPA, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, axitinib, bosutinib, cediranib, dasatinib, erlotinib, gefitinib, imatinib, lapatinib, lestaurtinib, nilotinib, semaxanib, sorafenib, sunitinib, vandetanib, retinoids (alitretinoin, tretinoin), altretamine, amsacrine, anagrelide, arsenic trioxide, asparaginase (pegaspargase), bexarotene, bortezomib, denileukin diftitox, estramustine, ixabepilone, masoprocol, mitotane, testolactone, tipifarnib, abetimus, deforolimus, everolimus, gusperimus, pimecrolimus, sirolimus, tacrolimus, temsirolimus, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a thienopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a thienopyrimidine compound for the production of a pharmaceutical composition for the prophylaxis or therapy of metabolic diseases is provided.

In yet a further aspect of the invention the use of a thienopyrimidine compound of the invention for the production of a pharmaceutical composition for treating or preventing a cytokine mediated disorder such as an inflammatory disease is provided.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a thienopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

In yet a further aspect of the invention the use of a thienopyrimidine compound of the invention for the production of a pharmaceutical composition for treating or preventing cancer, viral diseases or neurodegenerative diseases is provided.

For the purpose of the present invention, a therapeutically effective dosage will generally be from about 1 to 2000 mg/day, preferably from about 10 to about 1000 mg/day, and most preferably from about 10 to about 500 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

EXAMPLES

Example 1

Examples of Preparation of the Compounds of the Invention

The HPLC data provided in the examples described below were obtained as follows:
Conditions 10 cm_apci_formic and 10 cm_ESI_formic:
  HPLC column: Phenomenex Luna 5µ C18 (2), 100 mm×4.6 mm i.d. (Plus guard cartridge) at a flow rate of 2 mL/min.
  5.5 minute gradient from 95% 0.1% (v/v) formic acid in $H_2O$ to 95% 0.1% (v/v) formic acid in MeCN.
Conditions 10 cm_esci_BICARB:
  HPLC column: Waters Xterra MS 5 µm C18, 100 mm×4.6 mm i.d. (Plus guard cartridge) at a flow rate of 2 mL/min.
  5.5 minute gradient from 95% 10 mM ammonium bicarbonate in $H_2O$ to 95% MeCN.
  UV detection via HP or Waters DAD for all conditions:
  Start Range: 210 nm; End Range: 400 nm; Range interval: 4.0 nm;

The reverse phase preparative HPLC data provided in the examples described below were obtained as follows:
Trilution Standard Conditions
  HPLC Column: Waters Sunfire C18, 100 mm×19 mm i.d. (Plus guard cartridge) at a flow rate of 10 mL/min.
  33 minute gradient from 95% 0.1% (v/v) formic acid in $H_2O$ to 80% 0.1% (v/v) formic acid in $H_2O$ over 10 minutes rising to 100% 0.1% (v/v) formic acid in MeCN over 12 minutes. The gradient is held at 100% 0.1% (v/v) formic acid in MeCN for 3 minutes before column re-equilibration.
Polar Retention Conditions (15 cm_apci_Synergy_Formic or 15 cm_esci_Synergy_Formic)

| HPLC Setup | |
|---|---|
| Solvents: - | Acetonitrile (Far UV grade) with 0.1% (V/V) formic acid Water (High purity via PureLab Option unit) with 0.1% formic acid |
| Column: - | Phenomenex Synergy Hydro 4µ-RP 80A, 150 × 4.6 mm. |
| Flow Rate: - | 2 ml/min |
| Gradient: - | A: Water/formic    B: MeCN/formic |

| Time | A % | B % |
|---|---|---|
| 0.00 | 98 | 2 |
| 5.00 | 98 | 2 |
| 10.0 | 70 | 30 |
| 12.0 | 50 | 50 |
| 13.0 | 10 | 90 |
| 13.1 | 98 | 2 |
| 15 | 92 | 2 |

Typical Injections 2-7 ul

| UV detection via HP or Waters DAD |
|---|
| Start Range (nm) 210    End Range (nm) 400    Range interval (nm) 4.0 Other wavelength traces are extracted from the DAD data. Optional ELS detection using Polymer Labs ELS-1000. MS detection: Micromass ZQ single quadrapole LC-MS instrument. Flow splitter gives approximately 300 ul/min to mass spec Scan range for MS Data (m/z) Start (m/z) 100 End (m/z) 650 or 1000 when required With +ve/−ve switching Ionisation is either electrospray or APCI dependent on compound types (one ZQ has an ESCI option which can give both ESI and APCI data from a single run). Typical ESI voltages and temperatures are: Source 120-150 C.    3.5 KV capillary    25 V cone |

HPLC Conditions—25 cm_Bicarb_Xterra25_HPLC

| HPLC Setup | |
|---|---|
| Solvents: - | Acetonitrile (Far UV grade) Water (High purity via PureLab Option unit) with 10 mM ammonium bicarbonate (ammonium hydrogen carbonate) |
| Column: - | Waters Xterra 5µ C18 (2), 250 × 4.6 mm. |
| Flow Rate: - | 1 ml/min |
| Gradient: - | A: Water/formic    B: MeCN/formic |

| Time | A % | B % |
|---|---|---|
| 0.00 | 95 | 5 |
| 1.00 | 95 | 5 |
| 30.0 | 0 | 100 |
| 40.0 | 0 | 100 |
| 40.5 | 95 | 5 |
| 45 | 95 | 5 |

Typical Injections 2-7 ul
Instrument: Agilent 1100, Binary Pump, Agilent Sampler and Agilent DAD detector HPLC Conditions—15 cm_Formic_Slow_Sunfire_HPLC

| HPLC Setup | |
|---|---|
| Solvents: - | Acetonitrile (Far UV grade) with 0.1% (V/V) formic acid Water (High purity via PureLab Ultra unit) with 0.1% formic acid |
| Column: - | Waters Sunfire 5µ C18, 150 × 4.6 mm. |
| Flow Rate: - | 1 ml/min |
| Gradient: - | A: Water/formic    B: MeCN/formic |

| Time | A % | B % |
|---|---|---|
| 0.00 | 98 | 2 |
| 4.00 | 98 | 2 |
| 20.0 | 0 | 100 |

-continued

| | | |
|---|---|---|
| 22.0 | 0 | 100 |
| 22.5 | 98 | 2 |
| 24 | 98 | 2 |

Typical Injections 2-7 ul
Instrument: Agilent 1100, Binary Pump, Agilent Sampler and Agilent DAD detector
UV detection via Gilson Dual Wavelength Detector
The MS data provided in the examples described below were obtained as follows:
Mass spectrum: Micromass ZQ single quadrapole LC-MS instrument (ESI or AFCI).
The NMR data provided in the examples described below were obtained as follows:
$^1$H-NMR: Bruker DPX 400 MHz.
The microwave chemistry was performed on a single mode microwave reactor Smith Creator ™ from Personal Chemistry.

Abbreviations:
HATU (2-(7-aza-1H-benzotriazole-1-yl)-1,1,3,3-tetramethyluronium hexafluorophosphate)
DCM dichloromethane
DMF N,N-dimethylformamide
EtOAc ethyl acetate
THF tetrahydrofuran
MeOH methanol
MeCN acetonitrile General Synthetic Methods for the Compounds of the Invention, their Derivatives and Precursors In the following several general synthetic methods are described.

To a stirred solution of 3-fluoro-4-nitrobenzonitrile (15 g, 90.3 mmol) and $K_2CO_3$ (25.03 g, 181.1 mmol) in 100 mL of acetone/water (4:1) was added urea hydrogen peroxide adduct (16.99 g, 180.6 mmol) and the reaction stirred overnight at ambient temperature. DCM (100 mL) and water (500 mL) were added to the reaction mixture, the solution partitioned and the organic layer separated. The aqueous layer was extracted with DCM (3×100 mL) and the combined organic portions, washed with brine (100 mL), filtered through Celite and passed through a PTFE separation frit. The solvent was concentrated in vacuo and the title compound obtained as an orange solid (10 g, 60% yield) after recrystallisation from EtOAc/petroleum ether (40-60° C.).

$^1$H NMR (400 MHz; $d_6$-DMSO; 25° C.): δ 8.35 (br s, 1H), 8.01 (dd, 1H), 7.92 (dd, 1H), 7.89 (br s, 1H).

Preparation of 3-ethoxy-4-nitro-benzamide

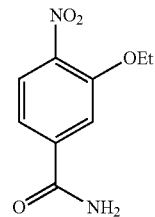 [SMILES: CCOc1cc(C(N)=O)ccc1[N+](=O)[O-]]

Ethanol (0.8 mL, 13.8 mmol) was added drop wise to a stirred suspension of sodium hydride (60% dispersion in oil, General Scheme 1

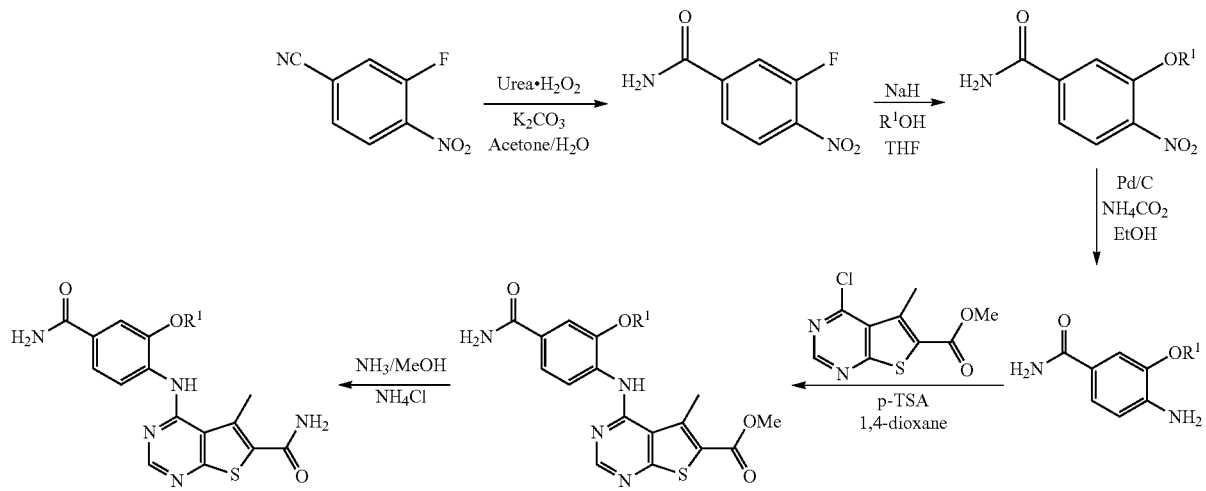

Preparation of 3-fluoro-4-nitro-benzamide

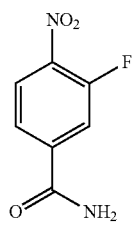

0.550 g, 13.8 mmol) in anhydrous THF (15 mL) at 0° C. and the resulting solution stirred for 0.5 hours. To this solution was added 3-fluoro-4-nitrobenzamide (2.11 g, 11.5 mmol) drop wise in anhydrous THF (15 mL). After complete addition the solution was stirred at 0° C. for 0.5 hours, before being allowed to warm to ambient temperature. The reaction was stirred at ambient temperature for 18 hours, quenched with water (30 mL) and the aqueous layer extracted with DCM (3×50 mL). The organic layers were combined, washed with brine (50 mL), dried ($Na_2SO_4$), filtered and concentrated in vacuo. The title compound was obtained as a yellow solid (1.694 g, 70% yield) after recrystallisation from MeOH.

$^1$H NMR (400 MHz; $d_6$-DMSO; 25° C.): δ 8.25 (br s, 1H), 7.96 (d, 1H), 7.70 (s, 1H), 7.65 (br s, 1H), 7.58 (d, 1H), 4.31 (q, 2H), 1.39 (t, 3H).

Preparation of 4-amino-3-ethoxy-benzamide

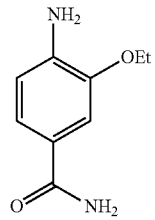

Palladium on carbon (5%, 0.510 g) was added into a solution of 3-ethoxy-4-nitro-benzamide (1.694 g, 8.06 mmol) and ammonium formate (2.17 g, 34.4 mmol) in MeOH (25 mL) at ambient temperature. The solution was stirred for 1 hour, filtered through Celite and washed with MeOH. The filtrate was concentrated in vacuo and triturated from diethyl ether to yield white solid (1.45 g, 100%).

$^1$H NMR (400 MHz; d$_6$-DMSO; 25° C.): 8.45 (s, 1H), 7.62 (br s, 1H), 7.30-7.34 (m, 2H), 6.92 (br s, 1H), 6.62 (d, 1H), 5.24 (br s, 2H), 4.06 (q, 2H), 1.39 (t, 3H).

Example 1

Methyl 4-(4-carbamoyl-2-ethoxyphenylamino)-5-methylthieno[2,3-d]pyrimidine-6-carboxylate

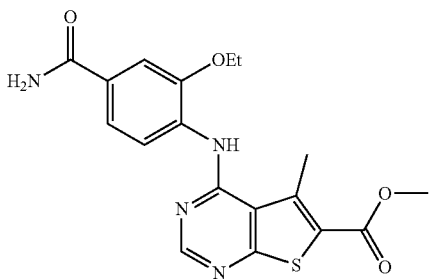 [SMILES: CCOc1cc(C(N)=O)ccc1Nc1ncnc2sc(C(=O)OC)c(C)c12]

4-amino-3-ethoxy-benzamide (0.045 g, 0.25 mmol), methyl 4-chloro-5-methyl-thieno[2,3-d]pyrimidine-6-carboxylate (0.061 g, 0.25 mmol, Fluorochem Ltd.) and para-toluene sulfonic acid (0.005 g, 0.025 mmol) were heated at reflux in anhydrous 1,4-dioxane (1.5 mL) for 16 hours. The solution was cooled to ambient temperature, ammonium hydroxide/water (1:4, 5 mL) added and the precipitate collected and washed successively with water and diethyl ether. The title compound was obtained as a yellow solid (0.057 g, 59%) after recrystallisation from MeOH.

$^1$H NMR (400 MHz; d$_6$-DMSO; 25° C.): δ 8.81 (s, 1H), 8.79 (s, 1H), 8.70 (s, 1H), 7.95 (br s, 1H), 7.62 (m, 2H), 7.33 (br s, 1H), 4.25 (q, 2H), 3.91 (s, 3H), 3.13 (s, 3H), 1.47 (t, 3H). MS (ESI$^+$): 418 (M+H). HPLC (10 cm_apci_formic): Rt 3.50 min (HPLC purity 97%).

Example 2

4-(4-Carbamoyl-2-ethoxyphenylamino)-5-methylthieno[2,3-d]pyrimidine-6-carboxamide

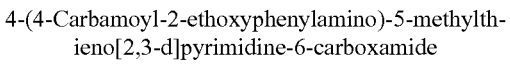
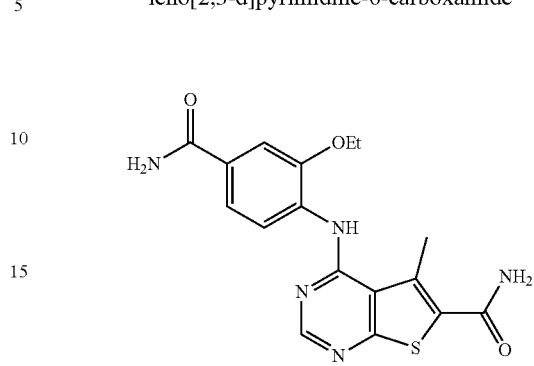

Methyl 4-(4-carbamoyl-2-ethoxyphenylamino)-5-methylthieno[2,3-d]pyrimidine-6-carboxylate (0.025 g, 0.06 mmol) and ammonium chloride (0.250 g, 4.67 mmol) in 7N ammonia/MeOH (3.5 mL) were heated at 100° C. in a sealed-tube for 14 days. The solution was cooled and the residue filtered. The precipitate was washed with water to yield white solid (0.015 g, 63%).

$^1$H NMR (400 MHz; d$_6$-DMSO; 25° C.): δ 8.81 (d, 1H), 8.76 (s, 1H), 8.68 (s, 1H), 7.75-8.00 (m, 3H), 7.63 (m, 2H), 7.34 (br s, 1H), 4.27 (q, 2H), 3.01 (s, 3H), 1.49 (t, 3H). MS (ESI$^+$): 372 (M+H). HPLC (10 cm_apci_formic): Rt 2.51 min (HPLC purity 97%).

Example 3

4-(4-Carbamoyl-2-ethoxyphenylamino)-5-methylthieno[2,3-d]pyrimidine-6-carboxylic acid

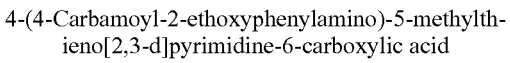
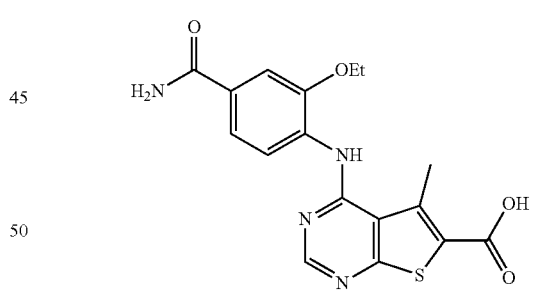

A suspension of methyl 4-(4-carbamoyl-2-ethoxyphenylamino)-5-methylthieno[2,3-d]pyrimidine-6-carboxylate (0.025 g, 0.06 mmol) in ammonium hydroxide (1.5 mL) was heated at 150° C. in a sealed-tube for 16 hours. The ammonium hydroxide was concentrated in vacuo and the residue redissolved in dimethyl sulfoxide. The sample was purified by reverse phase preparative HPLC to yield white solid (0.007 g, 29%).

$^1$H NMR (400 MHz; d$_6$-DMSO; 25° C.): δ 13.70 (br s, 1H), 8.82 (d, 1H), 8.80 (s, 1H), 8.70 (s, 1H), 7.98 (br s, 1H), 7.63 (s, 1H), 7.62 (d, 1H), 7.34 (br s, 1H), 3.17 (s, 3H), 2.70 (q, 2H), 1.49 (t, 3H). MS (ESI$^+$): 373 (M+H). HPLC (10 cm_apci_formic): Rt 2.84 min (HPLC purity 97%).

General Scheme 2

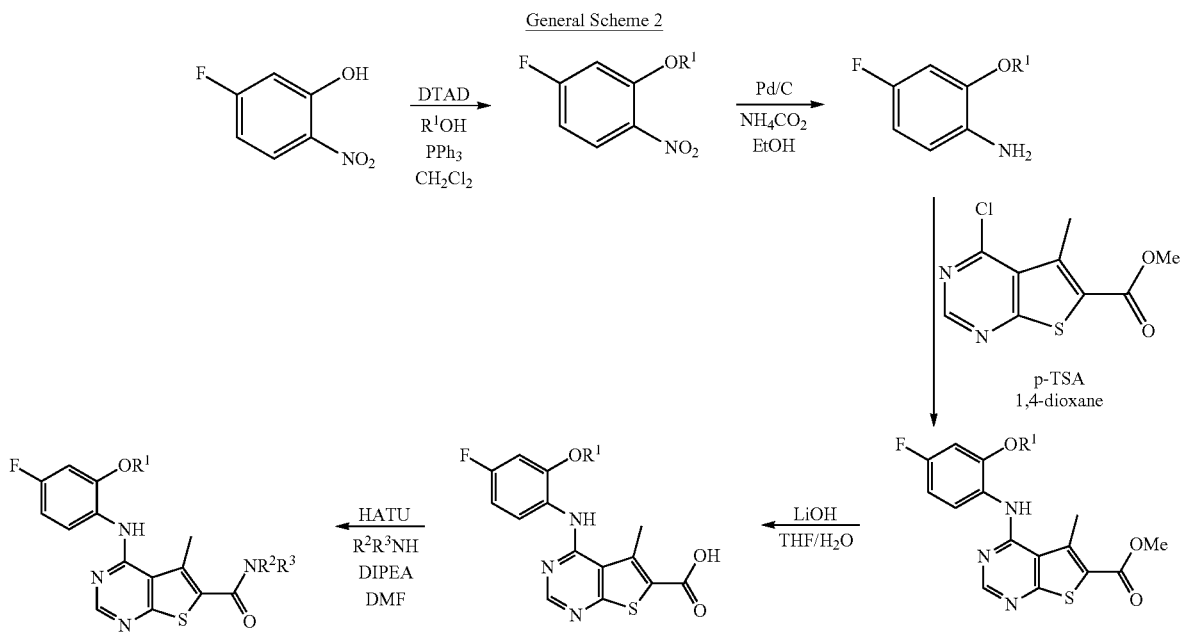

Preparation of
4-(5-fluoro-2-nitrophenoxy)tetrahydro-2H-pyran

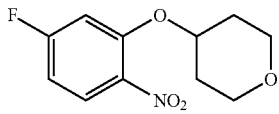

Di-tert-butyl azodicarboxylate (17.6 g, 76.4 mmol) was added into a solution of 5-fluoro-2-nitrophenol (10 g, 63.7 mmol), tetrahydro-2H-pyran-4-ol (7.3 mL, 76.4 mmol) and triphenyl phosphine (20 g, 76.4 mmol) in anhydrous DCM (120 mL) at 0° C. The solution was allowed to warm to ambient temperature overnight, concentrated in vacuo and the crude product triturated with n-pentane/diethyl ether (×2) to remove the triphenyl phosphine oxide (16.5 g) by-product. The sample was purified by flash column chromatography (5:1 petroleum ether (40-60° C.)/EtOAc) to yield yellow oil which was used in the next step directly.

$^1$H NMR (400 MHz; $d_6$-DMSO; 25° C.): δ 8.03 (dd, 1H), 7.48 (d, 1H), 7.00 (dd, 1H), 4.90-4.94 (m, 1H), 3.81-3.86 (m, 2H), 3.53-3.58 (m, 2H), 1.98-1.99 (m, 2H), 1.65-1.69 (m, 2H).

Preparation of
4-fluoro-2-(tetrahydro-2H-pyran-4-yloxy)aniline

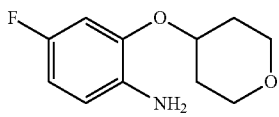

Ammonium formate (1.11 g, 17.6 mmol) was added into a suspension of 4-(5-fluoro-2-nitrophenoxy)tetrahydro-2H-pyran (1 g, 4.14 mmol) and palladium on carbon (5%, 0.250 g) in MeOH (10 mL) at ambient temperature. The solution was stirred for 0.5 hours, filtered through Celite and washed with MeOH. The filtrate was concentrated in vacuo and triturated from diethyl ether to remove the ammonium formate by-products. The sample was purified by flash column chromatography (5:1 petroleum ether (40-60° C.)/EtOAc→1:1 petroleum ether (40-60° C.)/EtOAc) to yield yellow oil (0.666 g, 76%).

$^1$H NMR (400 MHz; $d_6$-DMSO; 25° C.): δ 6.84 (d, 1H), 6.62-6.60 (m, 1H), 6.54 (app t, 1H), 4.52-4.57 (m, 3H), 3.86-3.92 (m, 2H), 3.47-3.52 (m, 2H), 1.95-1.98 (m, 2H), 1.60-1.69 (m, 2H).

Example 4

Methyl 4-(4-fluoro-2-(tetrahydro-2H-pyran-4-yloxy)phenylamino)-5-methylthieno[2,3-d]pyrimidine-6-carboxylate

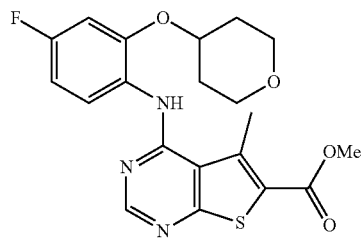 [SMILES: COC(=O)c1sc2ncnc(Nc3ccc(F)cc3OC3CCOCC3)c2c1C]

4-Fluoro-2-(tetrahydro-2H-pyran-4-yloxy)aniline (3.47 g, 16.4 mmol), methyl 4-chloro-5-methylthieno[2,3-d]pyrimidine-6-carboxylate (3.99 g, 16.4 mmol) and para-toluene sulfonic acid (0.313 g, 1.64 mmol) were heated at reflux in anhydrous 1,4-dioxane (30 mL) for 1.5 hours. The solution was cooled to ambient temperature, the precipitate collected and washed with cold 1,4-dioxane to yield the title compound as yellow solid (6.17 g, 90%).

$^1$H NMR (400 MHz; d$_6$-DMSO; 25° C.): δ 8.60 (s, 1H), 8.51 (s, 1H), 8.41 (t, 1H), 7.22 (d, 1H), 6.88 (t, 1H), 4.79 (m, 1H), 3.92 (s, 3H), 3.84 (m, 2H), 3.50 (m, 2H), 3.15 (s, 3H), 2.05 (2H, m), 1.62 (m, 2H). MS (ESI$^+$): 418 (M+H). HPLC (10 cm_ESI_formic): Rt 4.36 min (HPLC purity 99%).

Example 5

4-(4-Fluoro-2-(tetrahydro-2H-pyran-4-yloxy)phenylamino)-5-methylthieno[2,3-d]pyrimidine-6-carboxylic acid

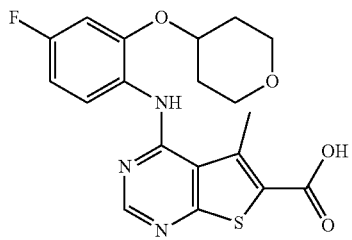 [SMILES: Cc1c(C(=O)O)sc2ncnc(Nc3ccc(F)cc3OC3CCOCC3)c12]

Methyl 4-(4-fluoro-2-(tetrahydro-2H-pyran-4-yloxy)phenylamino)-5-methylthieno[2,3-d]pyrimidine-6-carboxylate (9.0 g, 21.6 mmol) was suspended in THF/water (1:1; 200 mL). Into this solution was added lithium hydroxide monohydrate (5.31 g, 126.5 mmol) and the reaction stirred at ambient temperature overnight. The solution was cooled in an ice-bath and concentrated hydrochloric acid added until the solution reached pH 4. The precipitate was collected, washed with water and dried over P$_2$O$_5$ to yield off-white solid (8.642 g, 99%).

$^1$H NMR (400 MHz; d$_6$-DMSO; 25° C.): δ 13.70 (br s, 1H), 8.58 (s, 1H), 8.47-8.51 (m, 2H), 7.23 (d, 1H), 6.88 (app t, 1H), 4.74-4.81 (m, 1H), 3.84-3.89 (m, 2H), 3.47-3.53 (m, 2H), 3.13 (s, 3H), 2.06-2.09 (m, 2H), 1.60-1.69 (m, 2H). MS (ESI$^+$): 404 (M+H). HPLC (10 cm_apci_formic): Rt 3.68 min (HPLC purity 95%).

Example 6

4-(4-Fluoro-2-(tetrahydro-2H-pyran-4-yloxy)phenylamino)-N-(2-methoxyethyl)-5-methylthieno[2,3-d]pyrimidine-6-carboxamide

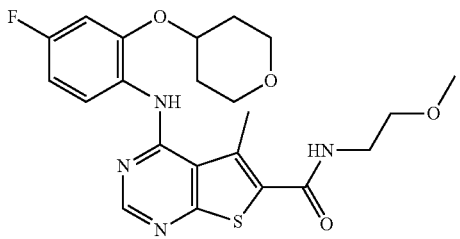 [SMILES: COCCNC(=O)c1sc2ncnc(Nc3ccc(F)cc3OC3CCOCC3)c2c1C]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 µL, 0.125 mmol) in DMF (2.0 mL) at 0° C. The reaction mixture was stirred at 0° C. for 0.5 hours. 2-Methoxyethylamine (54.3 µL, 0.625 mmol) was added and the coolant removed. The reaction mixture was stirred at ambient temperature overnight. The product was purified by reverse phase preparative HPLC to yield white solid (0.029 g, 50%)

$^1$H NMR (400 MHz; d$_6$-DMSO; 25° C.): δ 8.50 (m, 3H), 8.41 (s, 1H), 7.21 (d, 1H), 6.85 (t, 1H), 4.78 (m, 1H), 3.86 (m, 2H), 3.48 (m, 6H), 3.36 (s, 3H), 2.95 (s, 3H), 2.05 (m, 2H), 1.65 (2H, m). MS (ESI$^+$): 461 (M+H). HPLC (10 cm_ESI_formic): Rt 3.47 min (HPLC purity 99%).

Example 7

N-(2-(Dimethylamino)ethyl)-4-(4-fluoro-2-(tetrahydro-2H-pyran-4-yloxy)phenyl-amino)-5-methylthieno[2,3-d]pyrimidine-6-carboxamide

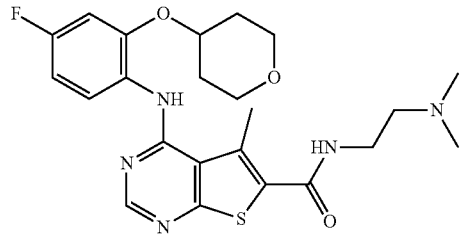 [SMILES: Cc1c(C(=O)NCCN(C)C)sc2ncnc(Nc3ccc(F)cc3OC3CCOCC3)c12]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 µL, 0.125 mmol) in DMF (2.0 mL) at 0° C. The reaction mixture was stirred at 0° C. for 0.5 hours. N,N-Dimethylethylenediamine (69 µL, 0.625 mmol) was added and the coolant removed. The reaction mixture was stirred at ambient temperature overnight. The product was purified by reverse phase preparative HPLC to yield white solid (0.031 g, 51%) after the resulting formate salt was free-based by stirring with polymer supported sodium carbonate in MeOH.

$^1$H NMR (400 MHz; d$_6$-DMSO; 25° C.): δ 8.56 (s, 1H), 8.50 (t, 1H), 8.39 (m, 2H), 7.22 (d, 1H), 6.89 (t, 1H), 4.28 (m, 1H), 3.85 (m, 2H), 3.50 (t, 2H), 3.39 (t, 2H), 2.96 (s, 3H), 2.46 (t, 2H), 2.23 (s, 6H), 2.06 (m, 2H), 1.63 (m, 2H). MS (ESI$^+$): 474 (M+H). HPLC (10 cm_ESI_formic): Rt 2.29 min (HPLC purity 99%).

Example 8

N-(2-(Dimethylamino)ethyl)-4-(4-fluoro-2-(tetrahydro-2H-pyran-4-yloxy)phenyl-amino)-N,5-dimethylthieno[2,3-d]pyrimidine-6-carboxamide

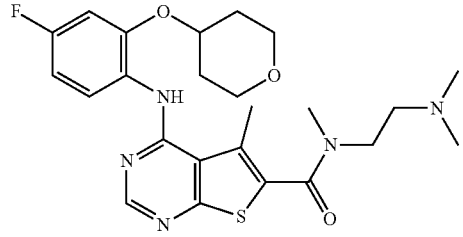 [SMILES: Cc1c(C(=O)N(C)CCN(C)C)sc2ncnc(Nc3ccc(F)cc3OC3CCOCC3)c12]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 µL, 0.125 mmol) in DMF (2.0 mL) at 0° C. The reaction mixture was stirred at 0° C. for 0.5 hours. N,N,N'-Trimethylethylenediamine (81 μL, 0.625 mmol) was added and the coolant removed. The reaction mixture was stirred at ambient temperature overnight. The product was purified by reverse phase preparative HPLC to yield white solid (0.031 g, 51%) after the resulting formate salt was free-based by stirring with polymer supported sodium carbonate in MeOH.

$^1$H NMR (400 MHz; $d_6$-DMSO; 25° C.): δ 8.52 (s, 1H), 8.42 (t, 1H), 8.17 (s, 1H), 7.09 (d, 1H), 6.82 (t, 1H), 4.77 (m, 1H), 3.86 (m, 2H), 3.64 (t, 2H), 3.51 (m, 2H), 3.07 (s, 3H), 2.73 (s, 5H), 2.37 (s, 6H), 2.06 (m, 2H), 1.67 (m, 2H). MS (ESI$^+$): 488 (M+H). HPLC (10 cm_ESI_formic): Rt 2.31 min (HPLC purity 98%).

Example 9

N-(3-(Dimethylamino)propyl)-4-(4-fluoro-2-(tetrahydro-2H-pyran-4-yloxy)phenyl-amino)-5-methylthieno[2,3-d]pyrimidine-6-carboxamide

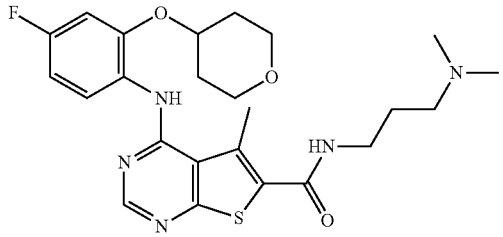 [SMILES: Cc1c(C(=O)NCCCN(C)C)sc2ncnc(Nc3ccc(F)cc3OC3CCOCC3)c12]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 μL, 0.125 mmol) in DMF (2.0 mL) at 0° C. The reaction mixture was stirred at 0° C. for 0.5 hours. 3-Dimethylamino-1-propylamine (69 μL, 0.625 mmol) was added and the coolant removed. The reaction mixture was stirred at ambient temperature overnight. The product was recrystallised from DMSO to yield off-white solid (0.031 g, 51%).

$^1$H NMR (400 MHz; $d_6$-DMSO; 25° C.): δ 8.58 (t, 1H), 8.49 (s, 1H), 7.01 (d, 1H), 6.74 (t, 1H), 4.71 (m, 1H), 3.93 (m, 2H), 3.56 (t, 2H), 3.43 (t, 2H), 2.99 (s, 3H), 2.51 (t, 2H), 2.32 (s, 6H), 2.15 (m, 2H), 1.85 (m, 2H), 1.73 (m, 2H). MS (ESI$^+$): 488 (M+H). HPLC (10 cm_ESI_formic): Rt 2.33 min (HPLC purity 95%).

Example 10

4-(4-Fluoro-2-(tetrahydro-2H-pyran-4-yloxy)phenylamino)-5-methyl-N-(2-morpholinoethyl)thieno[2,3-d]pyrimidine-6-carboxamide

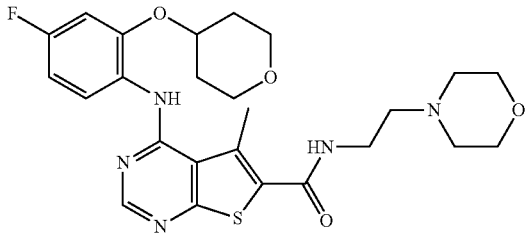 [SMILES: Cc1c(C(=O)NCCN2CCOCC2)sc2ncnc(Nc3ccc(F)cc3OC3CCOCC3)c12]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 μL, 0.125 mmol) in DMF (2.0 mL) at 0° C. The reaction mixture was stirred at 0° C. for 0.5 hours. 4-(2-Aminoethyl)morpholine (82 μL, 0.625 mmol) was added and the coolant removed. The reaction mixture was stirred at ambient temperature overnight. The product was recrystallised from DMSO to yield white solid (0.040 g, 62%).

$^1$H NMR (400 MHz; $d_6$-DMSO; 25° C.): δ 8.51 (m, 2H), 8.40 (m, 2H), 7.21 (d, 1H), 6.85 (t, 1H), 4.79 (m, 1H), 3.85 (m, 2H), 3.62 (m, 4H), 3.50 (m, 6H), 2.99 (s, 3H), 2.49 (m, 4H), 2.05 (m, 2H), 1.62 (m, 2H). MS (ESI$^+$): 516 (M+H). HPLC (10 cm_ESI_formic): Rt 2.34 min (HPLC purity 99%).

Example 11

4-(4-Fluoro-2-(tetrahydro-2H-pyran-4-yloxy)phenylamino)-N,5-dimethyl-thieno[2,3-d]pyrimidine-6-carboxamide

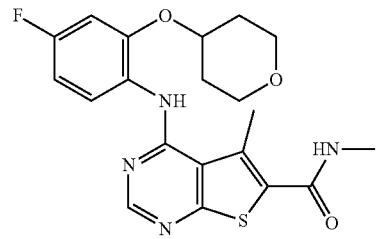 [SMILES: CNC(=O)c1sc2ncnc(Nc3ccc(F)cc3OC3CCOCC3)c2c1C]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 μL, 0.125 mmol) in DMF (2.0 mL) at 0° C. The reaction mixture was stirred at 0° C. for 0.5 hours. Methylamine (2M in THF, 1.0 mL, 2.0 mmol) was added and the coolant removed. The reaction mixture was stirred at ambient temperature overnight. The product was triturated with MeOH to yield a white solid (0.024 g, 46% yield).

$^1$H NMR (400 MHz; $d_6$-DMSO; 25° C.): δ 8.56 (s, 1H), 8.49 (t, 1H), 8.40 (m, 2H), 7.22 (d, 1H), 6.86 (t, 1H), 4.78 (m, 1H), 3.85 (m, 2H), 3.50 (t, 2H), 2.95 (s, 3H), 2.83 (s, 3H), 2.05 (m, 2H), 1.61 (m, 2H). MS (ESI$^+$): 417 (M+H). HPLC (10 cm_ESI_formic): Rt 3.38 min (HPLC purity 98%).

Example 12

4-[4-Fluoro-2-(tetrahydro-pyran-4-yloxy)-phenylamino]-5-methyl-thieno[2,3-d]pyrimidine-6-carboxylic acid dimethylamide

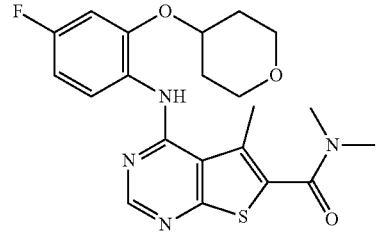 [SMILES: Cc1c(C(=O)N(C)C)sc2ncnc(Nc3ccc(F)cc3OC3CCOCC3)c12]

HATU (0.052 g, 0.138 mmol) was added into a mixture of methyl 4-(4-fluoro-2-(tetrahydro-2H-pyran-4-yloxy)phenylamino)-5-methylthieno[2,3-d]pyrimidine-6-carboxylate (0.050 g, 0.125 mmol) and Hünig's base (22 μL, 0.125 mmol) in DMF (2.0 mL) at 0° C. The reaction mixture was stirred at 0° C. for 0.5 hours. Dimethylamine (2M in THF, 1.0 mL, 2.0 mmol was added and the coolant removed. The reaction mixture was stirred at ambient temperature overnight. The solvent was concentrated in vacuo and the product purified by reverse phase preparative HPLC to yield white solid (0.017 g, 30%).

$^1$H NMR (400 MHz; $d_6$-DMSO; 25° C.): δ 8.55 (m, 2H), 8.33 (s, 1H), 7.22 (d, 1H), 6.88 (t, 1H), 4.78 (m, 1H), 3.85 (m, 2H), 3.49 (m, 2H), 3.02 (br s, 6H), 2.70 (s, 3H), 2.08 (m, 2H), 1.63 (m, 2H). MS (ESI$^+$): 431 (M+H). HPLC (10 cm_esci_BICARB): Rt 3.18 min (HPLC purity 99%).

Example 13

4-(4-Fluoro-2-(tetrahydro-2H-pyran-4-yloxy)phenylamino)-5-methylthieno[2,3-d]pyrimidine-6-carboxamide

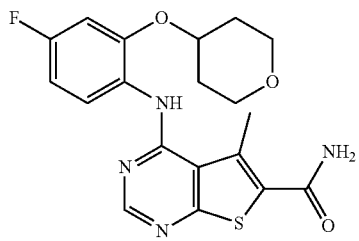 [SMILES: Cc1c(C(N)=O)sc2ncnc(Nc3ccc(F)cc3OC3CCOCC3)c12]

To a stirred suspension of 4-[4-fluoro-2-(tetrahydro-2H-pyran-4-yloxy)-phenylamino]-5-methyl-thieno[2,3-d]pyrimidine-6-carboxylic acid (0.5 g, 1.24 mmol) in THF/DMF (9.0 mL; 8:1) was added oxalyl chloride (0.33 mL, 3.7 mmol) and the mixture stirred for 18 hours. The solvent was concentrated and the residue co-evaporated with toluene. To the residue was added a solution of ammonia in dioxane (0.5 M, 20 mL) and the mixture stirred for 18 hours. The reaction mixture was diluted with 10% MeOH in DCM (50 mL) and absorbed onto silica. The crude product was chromatographed by flash column chromatography (3% MeOH in DCM) to give the product as pale yellow solid (0.278 g, 55.7%).

$^1$H NMR (400 MHz; $d_6$-DMSO; 25° C.): δ 8.56 (s, 1H), 8.50 (dd, 1H), 8.42 (s, 1H), 7.82 (bs, 2H), 7.25 (dd, 1H), 6.88 (dt, 1H), 4.78 (sept, 1H), 3.86 (dt, 2H), 3.50 (dt, 2H), 2.98 (s, 3H), 2.06 (d, 2H), 1.67-1.62 (m, 2H). MS (ESI$^+$): 403 (M+H). HPLC (10 cm_esci_BICARB): Rt 3.02 min (HPLC purity 97%).

Example 14

N-(3-Aminopropyl)-4-(4-fluoro-2-(tetrahydro-2H-pyran-4-yloxy)phenylamino)-5-methylthieno[2,3-d]pyrimidine-6-carboxamide

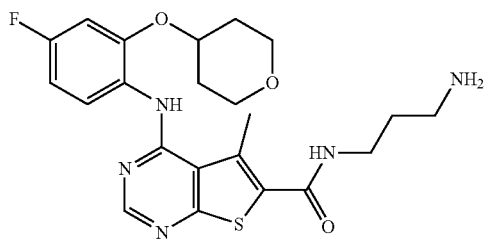 [SMILES: Cc1c(C(=O)NCCCN)sc2ncnc(Nc3ccc(F)cc3OC3CCOCC3)c12]

HATU (0.073 g, 0.193 mmol) was added into a mixture of methyl 4-(4-fluoro-2-(tetrahydro-2H-pyran-4-yloxy)phenylamino)-5-methylthieno[2,3-d]pyrimidine-6-carboxylate (0.07 g, 0.175 mmol) and Hünig's base (30 μL, 0.175 mmol) in DMF (2.0 mL) at 0° C. The reaction mixture was stirred at 0° C. for 0.5 hours. tert-Butyl 3-aminopropylcarbamate (0.152 g, 0.875 mmol) was added, the coolant removed and the reaction stirred at ambient temperature overnight. The product was recrystallised from EtOAc to yield colourless solid. The solid was dissolved in DCM (2.0 mL), treated with trifluoroacetic acid (0.50 mL) and the reaction stirred at ambient temperature for 2 hours. The reaction mixture was applied to an SCX cartridge and eluted with MeOH (30 mL) followed by ammonia in MeOH to elute the product. Evaporation of appropriate fractions gave the product as a colourless solid (0.049 g, 60%).

$^1$H NMR (400 MHz; CDCl$_3$; 25° C.): δ 8.75 (dd, 1H), 8.58 (s, 1H), 8.25 (s, 1H), 7.92 (s, 1H), 6.78-6.67 (m, 2H), 4.56-4.50 (m, 1H), 4.02 (dt, 2H), 3.63-3.51 (m, 4H), 3.06 (s, 3H), 2.97 (t, 2H), 2.14 (d, 2H), 1.85-1.74 (m, 4H). MS (ES$^-$): 458 (M−H). HPLC (10 cm_esci_BICARB): Rt 2.68 (HPLC purity 98%).

Example 15

4-(4-Fluoro-2-(tetrahydro-2H-pyran-4-yloxy)phenylamino)-5-methyl-N-(3-(methylamino)propyl)thieno[2,3-d]pyrimidine-6-carboxamide

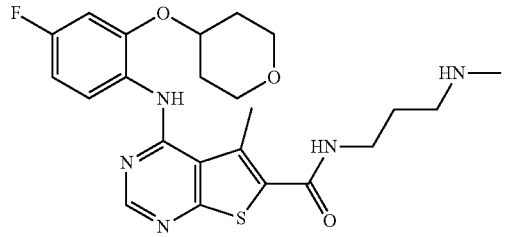 [SMILES: CNCCCNC(=O)c1sc2ncnc(Nc3ccc(F)cc3OC3CCOCC3)c2c1C]

HATU (0.073 g, 0.193 mmol) was added into a mixture of methyl 4-(4-fluoro-2-(tetrahydro-2H-pyran-4-yloxy)phenylamino)-5-methylthieno[2,3-d]pyrimidine-6-carboxylate (0.07 g, 0.175 mmol) and Hünig's base (30 μL, 0.175 mmol) in DMF (2.0 mL) at 0° C. The reaction mixture was stirred at 0° C. for 0.5 hours. tert-Butyl 3-aminopropyl(methyl)carbamate (0.164 g, 0.875 mmol) was added, the coolant removed and the reaction stirred at ambient temperature overnight. The product was recrystallised from EtOAc to yield colourless solid. The solid was dissolved in DCM (2.0 mL), treated with trifluoroacetic acid (0.50 mL) and the reaction stirred at ambient temperature for 2 hours. The reaction mixture was applied to an SCX cartridge and eluted with MeOH (30 mL) followed by ammonia in MeOH. Evaporation of appropriate fractions gave the product as a colourless solid (0.042 g, 50%).

$^1$H NMR (400 MHz; CDCl$_3$; 25° C.): δ 8.75 (dd, 1H), 8.58 (s, 2H), 8.27 (s, 1H), 6.79-6.68 (m, 2H), 4.57-4.49 (m, 1H), 4.02 (dt, 2H), 3.60-3.47 (m, 4H), 3.08 (s, 3H), 2.85 (t, 2H), 2.49 (s, 3H), 2.15 (d, 2H), 1.87-1.73 (m, 4H). MS (ES$^-$): 472 (M−H). HPLC (10 cm_esci_BICARB): Rt 2.69 (HPLC purity 98%).

Example 16

N-(4-Aminobutyl)-4-(4-fluoro-2-(tetrahydro-2H-pyran-4-yloxy)phenylamino)-5-methylthieno[2,3-d]pyrimidine-6-carboxamide

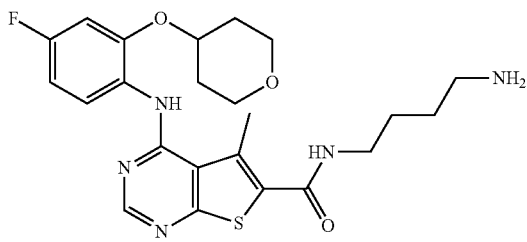 [SMILES: Cc1c(C(=O)NCCCCN)sc2ncnc(Nc3ccc(F)cc3OC3CCOCC3)c12]

HATU (0.073 g, 0.193 mmol) was added into a mixture of methyl 4-(4-fluoro-2-(tetrahydro-2H-pyran-4-yloxy)phenylamino)-5-methylthieno[2,3-d]pyrimidine-6-carboxylate (0.07 g, 0.175 mmol) and Hünig's base (30 μL, 0.175 mmol) in DMF (2.0 mL) at 0° C. The reaction mixture was stirred at 0° C. for 0.5 hours. tert-Butyl 4-aminobutylcarbamate (0.164 g, 0.875 mmol) was added, the coolant removed and the reaction stirred at ambient temperature overnight. The product was recrystallised from EtOAc to yield colourless solid. The solid was dissolved in DCM (2.0 mL), treated with trifluoroacetic acid (0.50 mL) and the reaction stirred at ambient temperature for 2 hours. The reaction mixture was applied to an SCX cartridge and eluted with MeOH (30 mL) followed by ammonia in MeOH. Evaporation of appropriate fractions gave the product as a colourless solid (0.024 g, 29%).
$^1$H NMR (400 MHz; CDCl$_3$; 25° C.): δ 8.76 (dd, 1H), 8.59 (s, 1H), 8.27 (s, 1H), 7.37 (s, 1H), 6.78-6.68 (m, 2H), 4.56-4.50 (m, 1H), 4.06-3.99 (m, 2H), 3.59-3.42 (m, 4H), 3.07 (s, 3H), 2.81 (t, 2H), 2.15 (d, 2H), 1.85-1.69 (m, 4H), 1.59 (m, 2H). MS (ES$^-$): 472 (M−H). HPLC (10 cm_esci_BICARB): Rt 2.73 (HPLC purity 98%).

Example 17

4-(4-Fluoro-2-(tetrahydro-2H-pyran-4-yloxy)phenylamino)-5-methyl-N-(4-(methylamino)butyl)thieno[2,3-d]pyrimidine-6-carboxamide

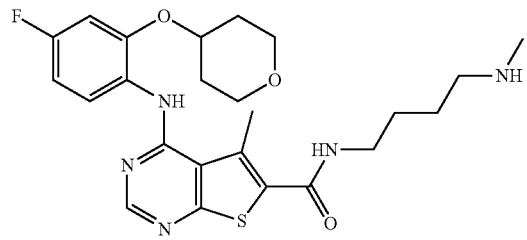 [SMILES: CNCCCCNC(=O)c1sc2ncnc(Nc3ccc(F)cc3OC3CCOCC3)c2c1C]

HATU (0.073 g, 0.193 mmol) was added into a mixture of methyl 4-(4-fluoro-2-(tetrahydro-2H-pyran-4-yloxy)phenylamino)-5-methylthieno[2,3-d]pyrimidine-6-carboxylate (0.07 g, 0.175 mmol) and Hünig's base (30 μL, 0.175 mmol) in DMF (2.0 mL) at 0° C. The reaction mixture was stirred at 0° C. for 0.5 hours. tert-Butyl 4-aminobutyl(methyl)carbamate (0.177 g, 0.875 mmol) was added, the coolant removed and the reaction stirred at ambient temperature overnight. The product was recrystallised from EtOAc to yield colourless solid. The solid was dissolved in DCM (2.0 mL), treated with trifluoroacetic acid (0.50 mL) and the reaction stirred at ambient temperature for 2 hours. The reaction mixture was applied to an SCX cartridge and eluted with MeOH (30 mL) followed by ammonia in MeOH. Evaporation of appropriate fractions gave the product as a colourless solid (0.042 g, 49%).
$^1$H NMR (400 MHz; CDCl$_3$; 25° C.): δ 8.76 (dd, 1H), 8.58 (s, 1H), 8.26 (s, 1H), 7.91 (s, 1H), 6.79-6.68 (m, 2H), 4.57-4.49 (m, 1H), 4.03 (dt, 2H), 3.60-3.42 (m, 4H), 3.06 (s, 3H), 2.69 (t, 2H), 2.44 (s, 3H), 2.15 (d, 2H), 1.95-1.61 (m, 6H). MS (ES$^-$): 486 (M−H). HPLC (10 cm_esci_BICARB): Rt 2.76 (HPLC purity 99%).

Example 18

N-(4-(Dimethylamino)butyl)-4-(4-fluoro-2-(tetrahydro-2H-pyran-4-yloxy)phenyl-amino)-5-methylthieno[2,3-d]pyrimidine-6-carboxamide

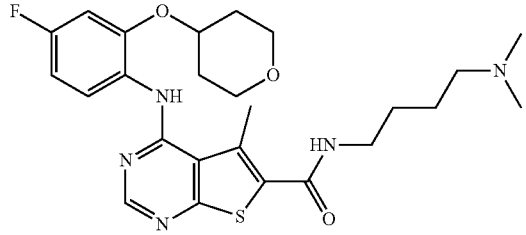 [SMILES: Cc1c(C(=O)NCCCCN(C)C)sc2ncnc(Nc3ccc(F)cc3OC3CCOCC3)c12]

HATU (0.073 g, 0.193 mmol) was added into a mixture of methyl 4-(4-fluoro-2-(tetrahydro-2H-pyran-4-yloxy)phenylamino)-5-methylthieno[2,3-d]pyrimidine-6-carboxylate (0.07 g, 0.175 mmol) and Hünig's base (30 μL, 0.175 mmol) in DMF (2.0 mL) at 0° C. The reaction mixture was stirred at 0° C. for 0.5 hours. N1,N1-dimethylbutane-1,4-diamine (0.177 g, 0.875 mmol) was added, the coolant removed and the reaction stirred at ambient temperature overnight. The crude reaction mixture was applied to an SCX cartridge and eluted with MeOH (30 mL) followed by ammonia in MeOH. The product was purified by flash column chromatography (10% MeOH/DCM→15% MeOH/DCM/0.5% NH$_4$OH) to give the title compound as a waxy colourless solid (0.012 g, 37%).
$^1$H NMR (400 MHz; CDCl$_3$; 25° C.): δ 8.76 (dd, 1H), 8.59 (s, 1H), 8.27 (s, 1H), 6.79-6.69 (m, 2H), 4.54 (dd, 1H), 4.03 (dt, 2H), 3.60-3.52 (m, 2H), 3.45 (q, 2H), 3.07 (s, 3H), 2.38 (t, 2H), 2.24 (s, 6H), 2.15 (d, 2H), 1.87-1.63 (m, 6H). MS (ESI$^+$): 502 (M+H). HPLC (10 cm_ESI_formic): Rt 2.18 (HPLC purity 97%).

Example 19

Methyl 4-(4-fluoro-2-iso-propoxyphenylamino)-5-methylthieno[2,3-d]pyrimidine-6-carboxylate

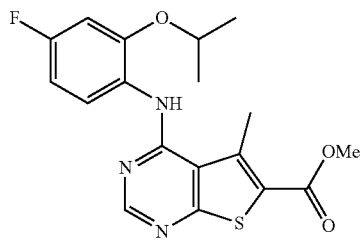 [SMILES: COC(=O)c1sc2ncnc(Nc3ccc(F)cc3OC(C)C)c2c1C]

Prepared from 4-fluoro-2-iso-propoxyaniline and methyl 4-chloro-5-methylthieno[2,3-d]pyrimidine-6-carboxylate in an analogous fashion to that given in general route 1. Yield (0.25 g, 53%)

$^1$H NMR (400 MHz; CDCl$_3$; 25° C.): δ 8.62-8.56 (m, 1H), 7.14 (d, 1H), 6.87 (t, 1H), 4.82 (sept, 2H), 3.92 (s, 3H), 3.15 (s, 3H), 1.36 (d, 6H). MS (ESI$^+$): 376 (M+H). HPLC (10 cm_ESI_formic): Rt 4.49 (HPLC purity 98%).

Example 20

4-(4-Fluoro-2-iso-propoxyphenylamino)-5-methylthieno[2,3-d]pyrimidine-6-carboxylic acid

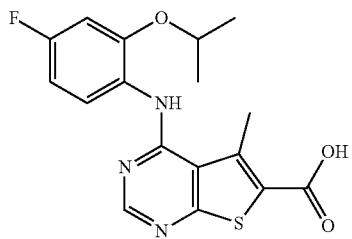 [SMILES: Cc1c(C(=O)O)sc2ncnc(Nc3ccc(F)cc3OC(C)C)c12]

Prepared in an analogous fashion to that given in general route 1. Yield (0.14 g, 72%).

$^1$H NMR (400 MHz; d$_6$-DMSO; 25° C.): δ 13.60 (bs, 1H), 8.65-8.53 (m, 3H), 7.15 (dd, 1H), 6.87 (dt, 1H), 4.84 (sept, 1H), 3.14 (s, 3H), 1.36 (d, 6H). MS (ESI$^+$): 362 (M+H). HPLC (10 cm_ESI_formic): Rt 3.90 min (HPLC purity 98%).

Preparation of methyl 4-chlorothieno[2,3-d]pyrimidine-6-carboxylate

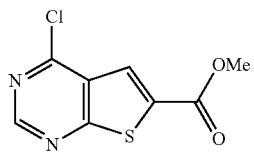 [SMILES: COC(=O)c1cc2c(Cl)ncnc2s1]

A solution of THF (50 mL) and Hünig's base (2.14 mL, 15.2 mmol) were cooled to −78° C. and n-BuLi (2.5 M in hexanes, 5.7 mL, 14.1 mmol) added drop wise. The solution was warmed to 0° C. for 10 minutes, re-cooled to −78° C. and 4-chlorothieno[2,3-d]pyrimidine (2.0 g, 11.7 mmol) added. The anion was stirred for 10 minutes at −78° C., methyl chloroformate (1.0 mL, 12.9 mmol) added drop wise and the reaction maintained at −78° C. for 0.5 hours. The reaction was allowed to warm to ambient temperature. After 1 hour, the mixture was poured into saturated aqueous ammonium chloride (50 mL) and extracted with EtOAc (4×50 mL). The combined organic layers were dried (Na$_2$SO$_4$), filtered and concentrated in vacuo. The crude product was purified by flash-column chromatography (100% DCM) to yield yellow solid (0.256 g, 10%).

$^1$H NMR (400 MHz; d$_6$-DMSO; 25° C.): δ 9.13 (s, 1H), 8.21 (s, 1H), 3.99 (s, 3H).

Example 21

Methyl 4-(4-fluoro-2-(tetrahydro-2H-pyran-4-yloxy) phenylamino)thieno[2,3-d]pyrimidine-6-carboxylate

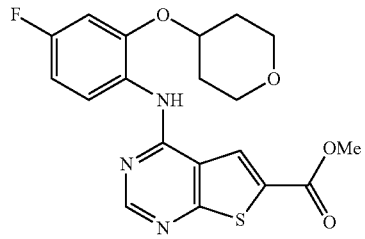 [SMILES: COC(=O)c1cc2c(Nc3ccc(F)cc3OC3CCOCC3)ncnc2s1]

Methyl 4-chlorothieno[2,3-d]pyrimidine-6-carboxylate (0.256 g, 1.12 mmol), 4-fluoro-2-(tetrahydro-2H-pyran-4-yloxy)aniline (0.236 g, 1.12 mmol) and para-toluene sulfonic acid (0.021 g, 0.01 mmol) were heated at reflux in anhydrous 1,4-dioxane (6 mL) for 4 hours. The solution was cooled, concentrated in vacuo and the crude product absorbed on to silica. The sample was purified by flash column chromatography (100% DCM→10% MeOH/DCM) to yield the title compound (0.220 g, 49%) after recrystallisation from MeOH.

$^1$H NMR (400 MHz; d$_6$-DMSO; 25° C.): δ 9.64 (s, 1H), 8.60 (br s, 1H), 8.44 (s, 1H), 4.49 (dd, 1H), 7.16 (d, 1H), 6.87 (app t, 1H), 4.63-4.65 (m, 1H), 3.93 (s, 3H), 3.39-3.44 (m, 2H), 1.85-1.89 (m, 2H), 1.45-1.49 (m, 2H). MS (ESI$^+$): 404 (M+H). HPLC (10 cm_ESI_formic): Rt 3.42 min (HPLC purity 96%).

Example 22

4-(4-Fluoro-2-(tetrahydro-2H-pyran-4-yloxy)phenylamino)thieno[2,3-d]pyrimidine-6-carboxylic acid

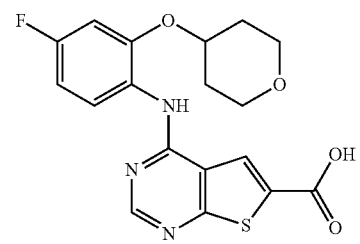 [SMILES: O=C(O)c1cc2c(Nc3ccc(F)cc3OC3CCOCC3)ncnc2s1]

Lithium hydroxide monohydrate (0.062 g, 1.49 mmol) was added into a suspension of methyl 4-(4-fluoro-2-(tetrahydro-2H-pyran-4-yloxy)phenylamino)thieno[2,3-d]pyrimidine-6-carboxylate (0.100 g, 0.25 mmol) in THF/water (1:1; 1.0 mL) and the reaction stirred at ambient temperature for 16 hours. The mixture was cooled in an ice-bath and 1 N hydrochloric acid added drop wise until the solution reached pH 5. The precipitate was collected, washed with water and dried over P$_2$O$_5$ to yield off-white solid (0.060 g, 62%).

$^1$H NMR (400 MHz; d$_6$-DMSO; 25° C.): δ 13.70 (br s, 1H), 9.56 (br s, 1H), 8.46 (br s, 1H), 8.43 (s, 1H), 7.50 (dd, 1H), 7.17 (dd, 1H), 6.86 (dd, 1H), 4.64-4.69 (m, 1H), 3.61-3.66 (m, 2H), 3.40-3.45 (m, 2H), 1.87-1.90 (m, 2H), 1.45-1.54 (m, 2H). MS (ESI$^+$): 390 (M+H). HPLC (10 cm_ESI_formic): Rt 2.90 min (HPLC purity 95%).

Example 23

N-(3-(Dimethylamino)propyl)-4-(4-fluoro-2-(tetrahydro-2H-pyran-4-yloxy)phenyl-amino)thieno[2,3-d]pyrimidine-6-carboxamide mono formate salt

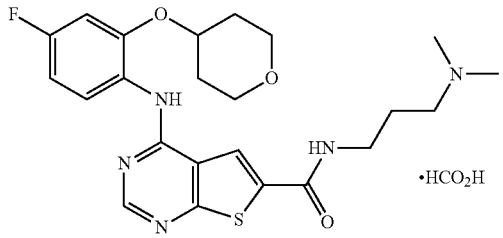 [SMILES: CN(C)CCCNC(=O)c1cc2c(Nc3ccc(F)cc3OC3CCOCC3)ncnc2s1 ; "·HCO2H"]

HATU (0.054 g, 0.14 mmol) was added into a solution of 4-(4-fluoro-2-(tetrahydro-2H-pyran-4-yloxy)phenylamino)thieno[2,3-d]pyrimidine-6-carboxylic acid (0.050 g, 0.13 mmol) and Hünig's base (22 µL, 0.13 mmol) in anhydrous DMF (1.0 mL) at 0° C. After 0.5 hours, 3-dimethylamino-1-propylamine (71 µL, 0.64 mmol) was added and the solution allowed to warm to ambient temperature over night. The reaction was concentrated in vacuo and the residue redissolved in dimethyl sulfoxide. The sample was purified by reverse phase preparative HPLC to yield off-white solid (0.007 g, 11%) as the mono-formate salt.

$^1$H NMR (400 MHz; CDCl$_3$; 25° C.): δ 8.86 (br s, 1H), 8.60 (s, 1H), 8.59 (s, 1H), 8.34 (dd, 1H), 8.22 (s, 1H), 7.91 (br s, 1H), 6.71-6.79 (m, 2H), 4.49-4.53 (m, 1H), 3.92-3.98 (m, 2H), 3.61 (br s, 2H), 3.55 (app dt, 2H), 3.07 (app t, 2H), 2.72 (s, 3H), 2.72 (s, 3H), 2.04-2.11 (m, 2H), 1.84-1.91 (m, 2H). MS (ESI$^+$): 474 (M+H). HPLC (10 cm_esci_bicarb): Rt 2.93 min (HPLC purity 99%).

Preparation of 3-nitro-2-(tetrahydro-2H-pyran-4-yloxy)pyridine

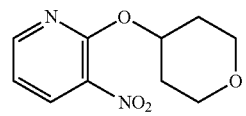

To a stirred solution of tetrahydro-2H-pyran-4-ol (2.5 g, 24.5 mmol) in anhydrous THF (20 mL) at 0° C. was added sodium hydride (60% dispersion in oil, 0.938 g, 24.5 mmol) and the mixture stirred at 0° C. for 0.5 h. A solution of 2-fluoro-3-nitro-pyridine (3.3 g, 23.2 mmol) in anhydrous THF (5 mL) was added drop wise with stirring and the solution allowed to warm to ambient temperature over 5 hours. The reaction was cooled in an ice-bath and water (50 mL) added. The mixture was extracted with EtOAc (2×100 mL) and the combined organic layers washed with brine (50 mL), dried (MgSO$_4$), filtered and concentrated in vacuo. The crude product was purified flash column chromatography (20% iso-hexane/DCM DCM) to yield the title compound as pale yellow oil (2.67 g, 48% yield).

General Scheme 3

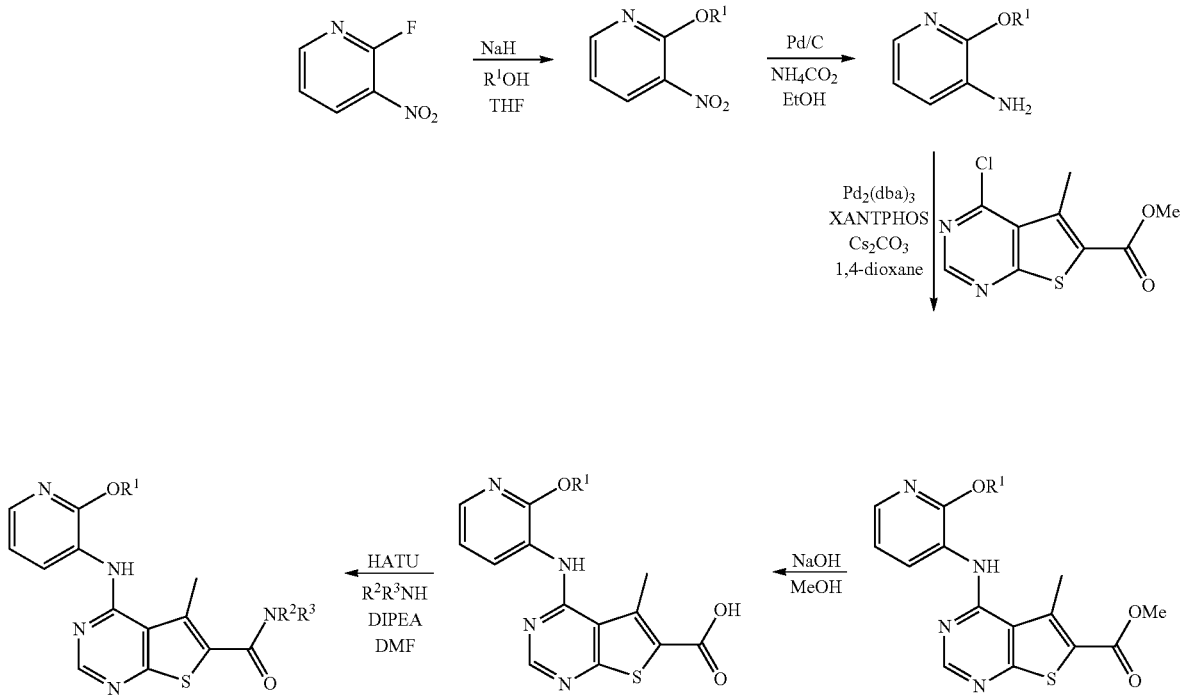

¹H NMR (400 MHz; CDCl₃; 25° C.): δ 8.35 (dd, 1H), 8.23 (dd, 1H), 7.02 (m, 1H), 5.50 (m, 1H), 4.00 (m, 2H), 3.65 (m, 2H), 2.07 (m, 2H), 1.91 (m, 2H).

Preparation of 2-(tetrahydro-2H-pyran-4-yloxy)pyridin-3-amine

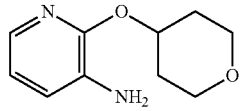

To a solution of 3-nitro-2-(tetrahydro-2H-pyran-4-yloxy)pyridine (2.31 g, 10.3 mmol) in anhydrous MeOH (20 mL) was added ammonium formate (1.2 g, 19.1 mmol) and palladium hydroxide on carbon (20%, 0.40 g). The mixture was stirred at ambient temperature for 8 hours when an additional aliquot of ammonium formate (1.0 g) was added. The mixture was heated at 50° C. for 4 hours, the solution adjusted to pH 8 with formic acid before further heating at 50° C. for one hour. The reaction was filtered through Celite and the catalyst residue washed with MeOH. The solvent was concentrated in vacuo to give a deep purple solid. The crude product was purified by ion-exchange chromatography (SCX-2 eluting with hydrochloric acid/MeOH ammonia/MeOH). The product crystallised as a white solid (1.8 g, 90%).

¹H NMR (400 MHz; CDCl₃; 25° C.): δ 7.53 (dd, 1H), 6.88 (dd, 1H), 6.70 (dd, 1H), 5.28 (m, 1H), 3.99 (m, 2H), 3.77 (br s, 2H), 3.62 (m, 2H), 2.1 (m, 2H), 1.78 (m, 2H).

Example 24

Preparation of methyl 5-methyl-4-(2-(tetrahydro-2H-pyran-4-yloxy)pyridin-3-ylamino)thieno[2,3-d]pyrimidine-6-carboxylate

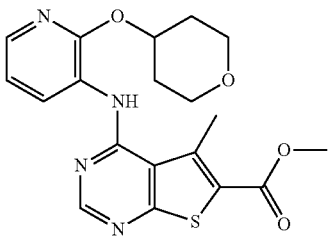 [SMILES: COC(=O)c1sc2ncnc(Nc3cccnc3OC3CCOCC3)c2c1C]

2-(Tetrahydro-2H-pyran-4-yloxy)pyridin-3-amine (0.99 g, 5.10 mmol), methyl 4-chloro-5-methylthieno[2,3-d]pyrimidine-6-carboxylate (1.237 g, 5.10 mmol) and para-toluene sulfonic acid (0.097 g, 0.51 mmol) were heated at reflux in anhydrous 1,4-dioxane (20 mL) for 16 hours. The solution was cooled to ambient temperature and poured into a stirred solution of ammonium hydroxide/water (1:4). The precipitate was filtered off, washed with water, diethyl ether and dried. The product was purified by reverse phase preparative HPLC to yield grey solid (0.963 g, 47%).

¹H NMR (400 MHz; d₆-DMSO; 25° C.): δ 8.83 (d, 1H), 8.69 (s, 1H), 8.58 (s, 1H), 7.92 (d, 1H), 7.10 (t, 1H), 5.31 (m, 1H), 3.90 (m, 5H), 3.55 (m, 2H), 3.17 (s, 3H), 2.10 (m, 2H), 1.72 (m, 2H). MS (ESI⁺): 401 (M+H). HPLC (10 cm_ESI_formic): Rt 4.18 min (HPLC purity 96%).

Example 25

Preparation of 5-methyl-4-(2-(tetrahydro-2H-pyran-4-yloxy)pyridin-3-ylamino)thieno[2,3-d]pyrimidine-6-carboxylic acid

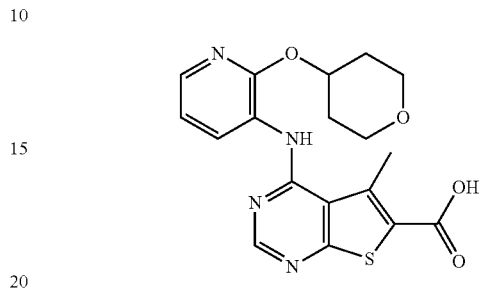

Methyl 5-methyl-4-(2-(tetrahydro-2H-pyran-4-yloxy)pyridin-3-ylamino)thieno[2,3-d]pyrimidine-6-carboxylate (0.921 g, 2.30 mmol) was added into a solution of MeOH (8 mL) and 2M aqueous sodium hydroxide (2.0 mL). The reaction was stirred at 60° C. for two hours. The mixture was cooled to ambient temperature and acidified with concentrated hydrochloric acid. On addition of DCM a precipitate formed which was collected and washed with water. The product was purified by reverse phase preparative HPLC to yield off-white solid which was used in the next step without further purification.

¹H NMR (400 MHz; d₆-DMSO; 25° C.): δ 8.89 (d, 1H), 8.68 (s, 1H), 8.55 (s, 1H), 7.91 (d, 1H), 7.10 (m, 1H), 5.30 (m, 1H), 3.90 (m, 2H), 3.53 (m, 2H), 3.18 (s, 3H), 2.10 (m, 2H), 1.75 (m, 2H). MS (ESI⁺): 387 (M+H). HPLC (10 cm_ESI_formic): Rt 3.39 min (HPLC purity 92%).

Example 26

Preparation of N-(2-(dimethylamino)ethyl)-5-methyl-4-(2-(tetrahydro-2H-pyran-4-yloxy)pyridin-3-ylamino)thieno[2,3-d]pyrimidine-6-carboxamide

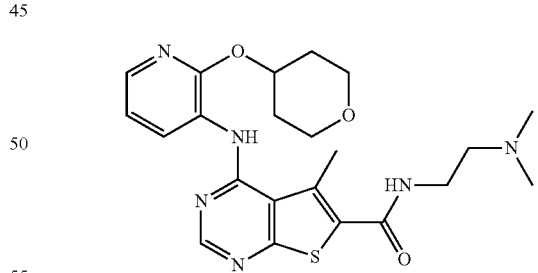

HATU (0.105 g, 0.28 mmol) was added into a mixture of 5-methyl-4-(2-(tetrahydro-2H-pyran-4-yloxy)pyridin-3-ylamino)thieno[2,3-d]pyrimidine-6-carboxylic acid (0.097 g, 0.25 mmol) and Hünig's base (44 μL, 0.25 mmol) in DMF (2.0 mL) at 0° C. The reaction mixture was stirred at 0° C. for 0.5 hours. N,N-Dimethylethylenediamine (137 μL, 1.25 mmol) was added and the coolant removed. The reaction mixture was stirred at ambient temperature overnight. The solvent was concentrated in vacuo and the product purified by reverse phase preparative HPLC to yield off-white solid (0.026 g, 22%).

¹H NMR (400 MHz; d₆-DMSO; 25° C.): δ 8.88 (d, 1H, d), 8.65 (s, 1H), 8.55 (t, 1H), 8.50 (s, 1H), 7.92 (d, 1H), 7.10 (m, 1H), 3.90 (m, 2H), 5.32 (m, 1H), 3.53 (m, 4H), 2.90-3.01 (m, 5H), 2.62 (s, 6H), 2.10 (m, 2H), 1.71 (m, 2H). MS (ESI⁺): 457 (M+H). HPLC (10 cm_ESI_formic): Rt 2.06 min (HPLC purity 97%).

Example 27

Preparation of N-(3-(dimethylamino)propyl)-5-methyl-4-(2-(tetrahydro-2H-pyran-4-yloxy)pyridin-3-ylamino)thieno[2,3-d]pyrimidine-6-carboxamide

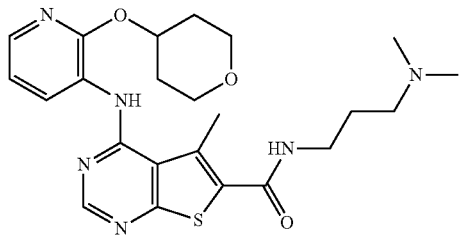 [SMILES: Cc1c(C(=O)NCCCN(C)C)sc2ncnc(Nc3cccnc3OC3CCOCC3)c12]

HATU (0.105 g, 0.28 mmol) was added into a mixture of 5-methyl-4-(2-(tetrahydro-2H-pyran-4-yloxy)pyridin-3-ylamino)thieno[2,3-d]pyrimidine-6-carboxylic acid (0.097 g, 0.25 mmol) and Hünig's base (44 µL, 0.25 mmol) in DMF (2.0 mL) at 0° C. The reaction mixture was stirred at 0° C. for 0.5 hours. 3-Dimethylamino-1-propylamine (138 µL, 1.25 mmol) was added and the coolant removed. The reaction mixture was stirred at ambient temperature overnight. The solvent was concentrated in vacuo and the product purified by reverse phase preparative HPLC to yield off-white solid (0.029 g, 24%).

¹H NMR (400 MHz; d₆-DMSO; 25° C.): δ 8.89 (d, 1H), 8.64 (s, 1H), 8.61 (t, 1H), 8.50 (s, 1H), 7.92 (d, 1H), 7.10 (m, 1H), 5.32 (m, 1H), 3.90 (m, 2H), 3.55 (m, 2H), 3.35 (m, 2H), 3.00 (s, 3H), 2.79 (m, 2H), 2.55 (s, 6H), 2.10 (m, 2H), 1.55 (m, 2H), 1.71 (m, 2H). MS (ESI⁺): 471 (M+H). HPLC (10 cm_ESI_formic): Rt 2.02 min (HPLC purity 98%).

Example 28

Preparation of 5-methyl-N-(2-(methylamino)ethyl)-4-(2-(tetrahydro-2H-pyran-4-yloxy)pyridin-3-ylamino)thieno[2,3-d]pyrimidine-6-carboxamide

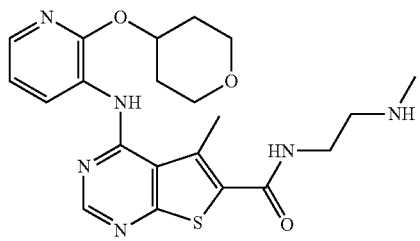 [SMILES: CNCCNC(=O)c1sc2ncnc(Nc3cccnc3OC3CCOCC3)c2c1C]

HATU (0.157 g, 0.41 mmol) was added into a mixture of 5-methyl-4-(2-(tetrahydro-2H-pyran-4-yloxy)pyridin-3-ylamino)thieno[2,3-d]pyrimidine-6-carboxylic acid (0.145 g, 0.38 mmol) and Hünig's base (65 µL, 0.38 mmol) in DMF (2.0 mL) at 0° C. The reaction mixture was stirred at 0° C. for 0.5 hours. N-Boc-N-methylethylenediamine (335 µL, 1.88 mmol) was added, the coolant removed and the reaction mixture stirred at ambient temperature overnight. The solvent was concentrated in vacuo and the crude product dissolved in DCM. The organic layer was washed with water, concentrated in vacuo (10 mL) and trifluoroacetic acid added (3.0 mL). The mixture was stirred at ambient temperature overnight, concentrated in vacuo and purified by ion-exchange chromatography (SCX-2 eluting with hydrochloric acid/MeOH→ammonia/MeOH). Further purification by flash-column chromatography (100% DCM→10% ammonia/MeOH/DCM) yielded the title compound as pale yellow solid (0.043 g, 25%).

¹H NMR (400 MHz; CDCl₃; 25° C.): δ 9.08 (d, 1H), 8.64 (s, 1H), 8.38 (s, 1H), 7.83 (d, 1H), 6.98 (m, 1H), 6.59 (m, 1H), 5.34-5.40 (m, 1H), 4.03 (dt, 2H), 3.62 (m, 2H), 3.52 (m, 2H), 3.07 (s, 3H), 2.85 (m, 2H), 2.46 (m, 3H), 2.20 (d, 2H), 1.77-1.87 (m, 2H). MS (ESI⁺): 443 (M+H). HPLC (10 cm_esci_BICARB): Rt 2.56 min (HPLC purity 95%).

Example 29

Preparation of N-(2-aminoethyl)-5-methyl-4-(2-(tetrahydro-2H-pyran-4-yloxy)pyridin-3-ylamino)thieno[2,3-d]pyrimidine-6-carboxamide

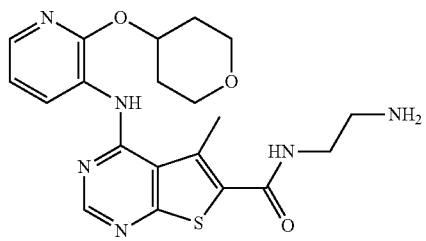 [SMILES: Cc1c(C(=O)NCCN)sc2ncnc(Nc3cccnc3OC3CCOCC3)c12]

HATU (0.157 g, 0.41 mmol) was added into a mixture of 5-methyl-4-(2-(tetrahydro-2H-pyran-4-yloxy)pyridin-3-ylamino)thieno[2,3-d]pyrimidine-6-carboxylic acid (0.145 g, 0.38 mmol) and Hünig's base (65 µL, 0.38 mmol) in DMF (2.0 mL) at 0° C. The reaction mixture was stirred at 0° C. for 0.5 hours. Tert-butyl-N-(2-aminoethyl) carbamate (296 µL, 1.88 mmol) was added and the coolant removed. The reaction mixture was stirred at ambient temperature overnight. The solvent was concentrated in vacuo and the crude product dissolved in DCM. The organic layer was washed with water, concentrated in vacuo (10 mL) and trifluoroacetic acid added (3.0 mL). The mixture was stirred at ambient temperature overnight, concentrated in vacuo and purified by ion-exchange chromatography (SCX-2 eluting with hydrochloric acid/MeOH→ammonia/MeOH). Further purification by flash-column chromatography (100% DCM→10% ammonia/MeOH/DCM) yielded the title compound as pale yellow solid (0.063 g, 39%).

¹H NMR (400 MHz; CDCl₃; 25° C.): δ 9.09 (d, 1H), 8.63 (s, 1H), 8.37 (s, 1H), 7.83 (d, 1H), 6.97 (t, 1H), 6.56 (t, 1H), 5.38 (m, 1H), 4.04 (m, 2H), 3.59 (m, 2H), 3.51 (q, 2H), 3.06 (s, 3H), 2.98 (t, 2H), 2.18 (m, 2H), 1.81 (m, 2H), 1.26 (m, 2H). MS (ESI⁺): 427 (M+H). HPLC (10 cm_esci_BICARB): Rt 2.47 min (HPLC purity 98%).

Example 30

Preparation of 5-methyl-N-(2-(pyrrolidin-1-yl)ethyl)-4-(2-(tetrahydro-2H-pyran-4-yloxy)pyridin-3-ylamino)thieno[2,3-d]pyrimidine-6-carboxamide

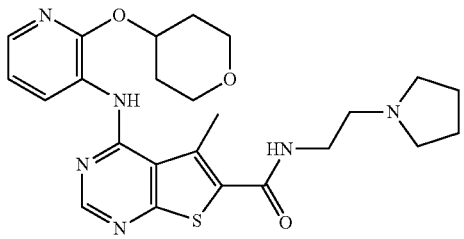 [SMILES: Cc1c(C(=O)NCCN2CCCC2)sc2ncnc(Nc3cccnc3OC3CCOCC3)c12]

HATU (0.105 g, 0.28 mmol) was added into a mixture of 5-methyl-4-(2-(tetrahydro-2H-pyran-4-yloxy)pyridin-3-ylamino)thieno[2,3-d]pyrimidine-6-carboxylic acid (0.097 g, 0.25 mmol) and Hünig's base (44 µL, 0.25 mmol) in DMF (2.0 mL) at 0° C. The reaction mixture was stirred at 0° C. for 0.5 hours. 1-(2-Aminoethyl)-pyrrolidine (157 µL, 1.25 mmol) was added and the coolant removed. The reaction mixture was stirred at ambient temperature overnight. The solvent was concentrated in vacuo, the crude material added into water (10 mL) and the aqueous layer extracted into DCM. The product was purified by flash-column chromatography (DCM→10% ammonia/MeOH/DCM) to yield the title compound as off-white solid (0.051 g, 42% yield).

$^1$H NMR (400 MHz; CDCl$_3$; 25° C.): δ 9.08 (d, 1H), 8.62 (s, 1H), 8.35 (s, 1H), 7.81 (d, 1H), 6.96 (t, 1H), 6.73 (t, 1H), 5.36 (m, 1H), 4.00 (m, 2H), 3.52-3.65 (m, 4H), 3.05 (s, 3H), 2.72 (t, 2H), 2.58 (m, 4H), 2.18 (m, 2H), 1.80 (m, 6H). MS (ESI$^+$): 483 (M+H). HPLC (10 cm_esci_BICARB): Rt 2.94 min (HPLC purity 98%).

Example 31

Protocol for the Preparation of 4-(2-iso-propoxypyridin-3-ylamino)-5-methylthieno[2,3-d]pyrimidine-6-carboxylic acid

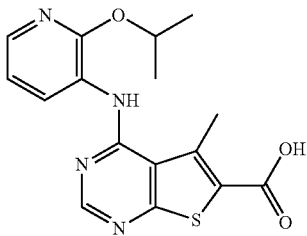 [SMILES: Cc1c(C(=O)O)sc2ncnc(Nc3cccnc3OC(C)C)c12]

a) Preparation of 2-iso-propoxy-3-nitro-pyridine

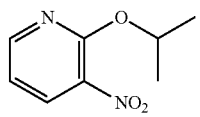

iso-Propanol (1.41 mL, 18.48 mmol) was added drop wise into a stirred suspension of sodium hydride (60% dispersion in oil, 0.739 g, 18.48 mmol) in anhydrous THF (20 mL) at 0° C. and the resulting solution stirred for 0.5 hours. To this solution was added 2-fluoro-3-nitropyridine (2.50 g, 17.60 mmol) drop wise in anhydrous THF (10 mL). After complete addition the solution was stirred at 0° C. for 0.5 hours, before being allowed to warm to ambient temperature. The reaction was stirred at ambient temperature for 18 hours, quenched with water (50 mL) and the aqueous layer extracted with diethyl ether (3×50 mL). The organic layers were combined, washed with brine (50 mL), dried (Na$_2$SO$_4$), filtered and concentrated in vacuo. The title compound was obtained as a yellow solid (1.975 g, 61% yield) after purification by flash-column chromatography (petroleum ether (40-60° C.)/DCM).

$^1$H NMR (400 MHz; CDCl$_3$; 25° C.): δ 8.36 (d, 1H), 8.18 (d, 1H), 6.97 (t, 1H), 5.51 (m, 1H), 1.41 (d, 6H). MS (ESI$^+$): Mass ion not observed. HPLC (10 cm_esci_BICARB): Rt 3.43 min (HPLC purity 94%).

b) Preparation of iso-propoxypyridin-3-amine

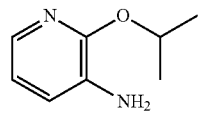

Palladium hydroxide on carbon (20%, 0.076 g, 0.54 mmol) was added into a solution of 2-iso-propoxy-3-nitro-pyridine (1.97 g, 10.8 mmol) and ammonium formate (3.40 g, 54.0 mmol) in ethanol (100 mL) at ambient temperature. The solution was stirred for 2 hours at 90° C., cooled to ambient temperature, filtered through Celite and washed with MeOH. The filtrate was concentrated in vacuo and triturated from diethyl ether to yield brown oil which was used in the next step without further purification.

$^1$H NMR (400 MHz; CDCl$_3$; 25° C.): δ 7.56 (d, 1H), 7.26 (d, 1H), 6.65 (m, 1H), 5.33 (m, 1H), 3.65 (br s, 2H), 1.35 (d, 6H). MS (ESI$^+$): 153 (M+H). HPLC (10 cm_ESI_formic): Rt 2.24 min (HPLC purity 99%).

c) Preparation of methyl 4-(2-iso-propoxypyridin-3-ylamino)-5-methylthieno[2,3-d]pyrimidine-6-carboxylate

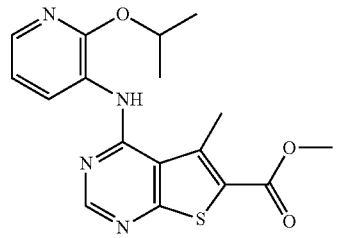 [SMILES: COC(=O)c1sc2ncnc(Nc3cccnc3OC(C)C)c2c1C]

iso-Propoxypyridin-3-amine (1.30 g, 8.60 mmol) was added into a solution of methyl 4-chloro-5-methylthieno[2,3-d]pyrimidine-6-carboxylate (2.295 g, 9.46 mmol), XANT-PHOS (0.995 g, 1.72 mmol) and cesium carbonate (3.922 g, 12.04 mmol) in degassed 1,4-dioxane (40 mL). The mixture was degassed under sonnication, tris(dibenzylideneacetone)dipalladium (0.394 g, 0.430 mmol) added and the mixture sonnicated further. The reaction was sealed, heated at 90° C. for 3.0 hours, cooled, filtered and the solid washed with cold 1,4-dioxane. The filtrate was poured into ammonium hydroxide solution and the precipitate collected to yield the title compound as dark yellow solid (2.05 g, 66%).

$^1$H NMR (400 MHz; d$_6$-DMSO; 25° C.): δ 8.89 (d, 1H), 8.68 (s, 1H), 8.59 (br s, 1H), 7.93 (d, 1H), 7.08 (m, 1H), 5.37

(m, 1H), 3.92 (s, 3H), 3.16 (s, 3H), 1.41 (d, 6H). MS (ESI+): 359 (M+H). HPLC (10 cm_ESI_formic): Rt 4.60 min (HPLC purity 87%).

d) Preparation of 4-(2-iso-propoxypyridin-3-ylamino)-5-methylthieno[2,3-d]pyrimidine-6-carboxylic acid

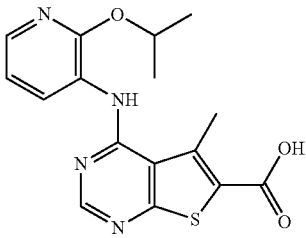 [SMILES: Cc1c(C(=O)O)sc2ncnc(Nc3cccnc3OC(C)C)c12]

Methyl 4-(2-iso-propoxypyridin-3-ylamino)-5-methylthieno[2,3-d]pyrimidine-6-carboxylate (2.04 g, 5.7 mmol) was suspended in MeOH (24 mL). Into this solution was added a solution of aqueous 2M sodium hydroxide (6.0 mL, 12 mmol) and the reaction stirred at 60° C. for 1 hour. The solution was cooled in an ice-bath and concentrated hydrochloric acid added until the solution reached pH 5. The precipitate was collected, washed with water and dried to yield off-white solid (1.50 g, 76%).

$^1$H NMR (400 MHz; $d_6$-DMSO; 25° C.): δ 13.75 (br s, 1H), 8.92 (d, 1H), 8.68 (s, 1H), 8.58 (s, 1H), 7.92 (d, 1H), 7.09 (m, 1H), 5.36 (m, 1H), 3.16 (s, 3H), 1.42 (d, 6H). MS (ESI+): 345 (M+H). HPLC (10 cm_ESI_formic): Rt 3.81 min (HPLC purity 98%).

Example 32

Protocol for the Preparation of tert-butyl 3-(3-(2-(methoxycarbonyl)-3-methyl benzo[b]thiophen-4-ylamino)pyridin-2-yloxy)azetidine-1-carboxylate

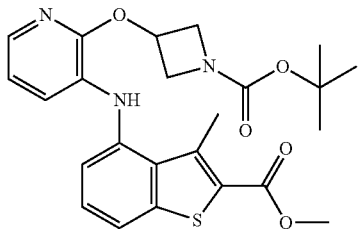 [SMILES: COC(=O)c1sc2cccc(Nc3cccnc3OC3CN(C(=O)OC(C)(C)C)C3)c2c1C]

a) Preparation of tert-butyl 3-(3-nitropyridin-2-yloxy)azetidine-1-carboxylate

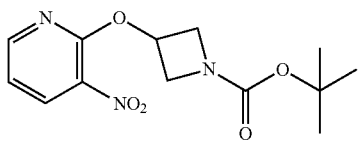 [SMILES: CC(C)(C)OC(=O)N1CC(Oc2ncccc2[N+](=O)[O-])C1]

Sodium hydride (60% dispersion in oil, 2.30 g, 57.64 mmol) was added portionwise into a solution of 1-Boc-3-(hydroxy)azetidine (9.94 g, 57.64 mmol) in anhydrous THF (110 mL) at 0° C. and stirred for 0.5 hour. A solution of 2-fluoro-3-nitro-pyridine (7.80 g, 54.9 mmol) in anhydrous THF (15 mL) was added drop wise and the mixture allowed to warm to ambient temperature overnight. The mixture was cooled in an ice-bath and water (50 mL) added. The product was extracted with EtOAc, washed with water, brine and dried ($Na_2SO_4$). The product was purified by flash-column chromatography (petroleum ether (40-60° C.)/DCM) to yield the title compound as a yellow solid (4.37 g, 27%).

$^1$H NMR (400 MHz; $CDCl_3$; 25° C.): δ 8.36 (m, 1H), 8.30 (d, 1H), 7.09 (m, 1H), 5.45 (m, 1H), 4.35 (m, 2H), 4.06 (m, 2H), 1.45 (s, 9H). MS (ESI+): 296 (M+H). HPLC (10 cm_esci_BICARB): Rt 3.47 min (HPLC purity 93%).

b) Preparation of tert-butyl 3-(3-aminopyridin-2-yloxy)azetidine-1-carboxylate

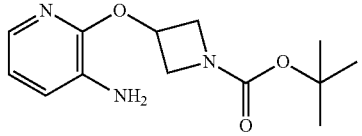

Palladium hydroxide on carbon (20%, 0.071 g, 0.51 mmol) was added into a solution of tert-butyl 3-(3-nitropyridin-2-yloxy)azetidine-1-carboxylate (3.0 g, 10.2 mmol) and ammonium formate (3.20 g, 50.8 mmol) in ethanol (100 mL). The solution was stirred at ambient temperature for 18 hours, filtered through Celite and concentrated in vacuo. The crude product was extracted with chloroform (×3) and the combined organic fractions concentrated in vacuo to yield pale brown solid (2.48 g, 92%).

$^1$H NMR (400 MHz; $CDCl_3$; 25° C.): δ 7.33 (m, 1H), 6.92 (d, 1H), 6.74 (m, 1H), 5.27 (m, 1H), 5.07 (s, 2H), 4.26 (m, 2H), 3.86 (m, 2H), 1.42 (s, 9H). MS (ESI+): 266 (M+H). HPLC (10 cm_esci_BICARB): Rt 3.09 min (HPLC purity 90%).

c) Preparation of tert-butyl 3-(3-(2-(methoxycarbonyl)-3-methylbenzo[b]thiophen-4-ylamino)pyridin-2-yloxy)azetidine-1-carboxylate

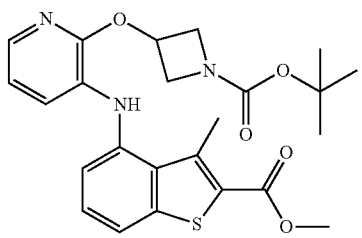 [SMILES: COC(=O)c1sc2cccc(Nc3cccnc3OC3CN(C(=O)OC(C)(C)C)C3)c2c1C]

Tert-butyl 3-(3-aminopyridin-2-yloxy)azetidine-1-carboxylate (1.56 g, 5.90 mmol) was added into a solution of methyl 4-chloro-5-methylthieno[2,3-d]pyrimidine-6-carboxylate (1.57 g, 6.49 mmol), XANTPHOS (0.683 g, 1.18 mmol) and cesium carbonate (2.69 g, 8.26 mmol) in degassed 1,4-dioxane (50 mL). The mixture was degassed under sonnication, tris(dibenzylideneacetone)dipalladium (0.270 g, 0.30 mmol) added and the mixture sonnicated further. The reaction was sealed, heated at 90° C. overnight and concentrated in vacuo. The product was purified by flash-column chromatography (petroleum ether (40-60° C.) 1:1 petroleum ether (40-60° C.)/EtOAc), trituration from MeCN and reverse phase preparative HPLC to yield the title compound as yellow solid.

$^1$H NMR (400 MHz; $d_6$-DMSO; 25° C.): δ 8.73 (d, 1H), 8.61 (s, 1H), 8.55 (s, 1H), 7.91 (d, 1H), 7.13 (t, 1H), 5.42 (m, 1H), 4.31 (m, 2H), 3.92 (m, 5H), 3.16 (s, 3H), 1.43 (s, 9H). MS (ESI+): 470 (M+H). HPLC (10 cm_esci_BICARB): Rt 4.33 min (HPLC purity 98%).

General Scheme 4

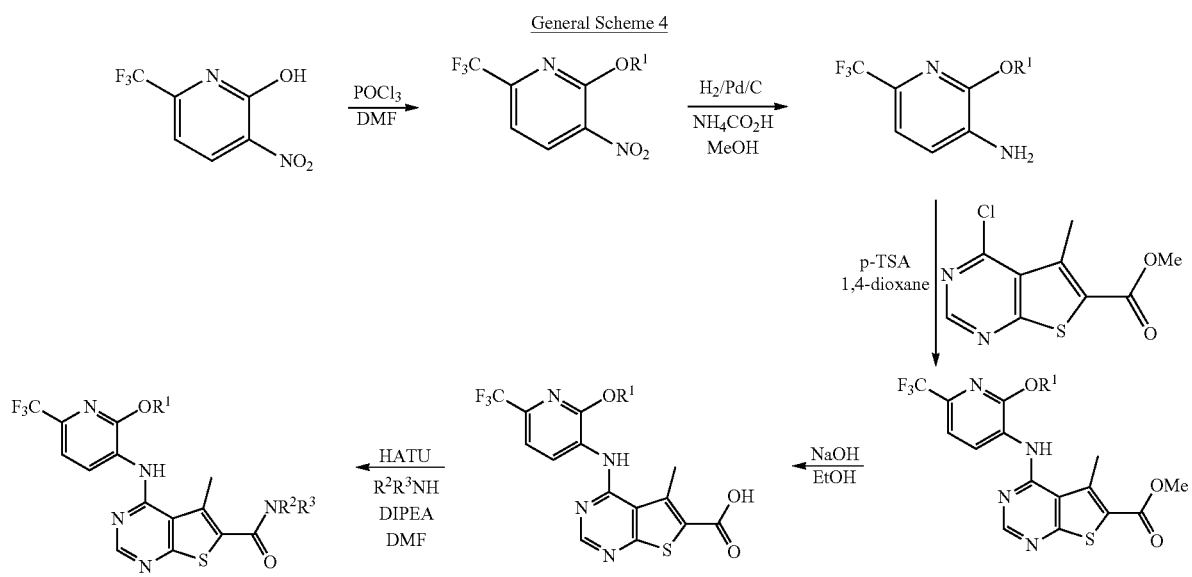

Preparation of 3-nitro-2-(tetrahydro-2H-pyran-4-yloxy)-6-(trifluoromethyl)pyridine

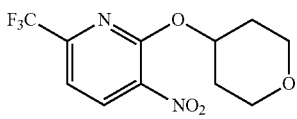 [SMILES: O=[N+]([O-])c1ccc(C(F)(F)F)nc1OC1CCOCC1]

To a solution of 3-nitro-6-(trifluoromethyl)-2(1'-1)-pyridone (prepared according to WO2001/96338, 0.208 g, 1.00 mmol) and triphenylphosphine (0.314 g, 1.20 mmol) in anhydrous THF (5.0 mL) was added di-tert-butylazodicarbonate (0.275 mL, 1.20 mmol). The reaction mixture was stirred for 1 hour. To the resultant suspension was added tetrahydro-2H-pyran-4-ol (0.114 mL, 1.20 mmol) and the resultant solution stirred at ambient temperature for 17 hours. The solvent was removed in vacuo and the residue was purified by flash column chromatography (100% iso-hexane 60:10 iso-hexane/EtOAc) to afford the title compound as an off-white solid (0.266 g, 91%).

$^1$H NMR (400 MHz; CDCl$_3$; 25° C.): δ 8.39 (d, 1H), 7.40 (m, 1H), 5.56-5.50 (m, 1H), 4.02-3.96 (m, 2H), 3.71-3.66 (m, 2H), 2.15-2.08 (m, 2H), 1.95-1.87 (m, 2H).

Preparation of 2-(tetrahydro-2H-pyran-4-yloxy)-6-(trifluoromethyl)pyridin-3-amine

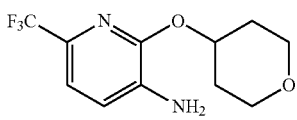

Prepared as described for 2-(tetrahydro-2H-pyran-4-yloxy)-5-(trifluoromethyl)pyridin-3-amine to afford the title compound as an oil (0.195 g, 84%).

$^1$H NMR (400 MHz; CDCl$_3$; 25° C.): δ 7.10 (d, 1H), 6.89 (d, 1H), 5.36-5.30 (m, 1H), 4.10 (br s, 2H), 4.01-3.96 (m, 2H), 3.67-3.61 (m, 2H), 2.17-2.10 (m, 2H), 1.87-1.77 (m, 2H).

Example 33

Methyl 4-(2-(tetrahydro-2H-pyran-4-yloxy)-6-(trifluoromethyl)pyridin-3-ylamino)-5-methylthieno[2,3-d]pyrimidine-6-carboxylate

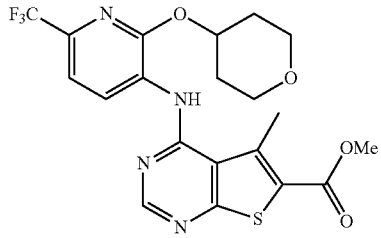 [SMILES: COC(=O)c1sc2ncnc(Nc3ccc(C(F)(F)F)nc3OC3CCOCC3)c2c1C]

Prepared as described for methyl 4-(6-chloro-2-(tetrahydro-2H-pyran-4-yloxy)pyridin-3-ylamino)-5-methylthieno[2,3-d]pyrimidine-6-carboxylate to afford the title compound as a red solid (0.159 g, 48%).

$^1$H NMR (400 MHz; CDCl$_3$; 25° C.): δ 9.27 (d, 1H), 8.72 (s, 1H), 8.54 (br s, 1H), 7.38 (d, 1H), 5.45-5.40 (1H, m), 4.08-4.03 (m, 2H), 3.96 (s, 3H), 3.68-3.62 (m, 2H), 3.19 (s, 3H), 2.26-2.22 (m, 2H), 1.90-1.80 (m, 2H). MS (ESI$^+$): 469 (M+H). HPLC (10 cm_ESI_formic): Rt 4.64 min (HPLC purity 99%).

Example 34

4-(2-(Tetrahydro-2H-pyran-4-yloxy)-6-(trifluoromethyl)pyridin-3-ylamino)-N-(3-(dimethylamino)propyl)-5-methylthieno[2,3-d]pyrimidine-6-carboxamide

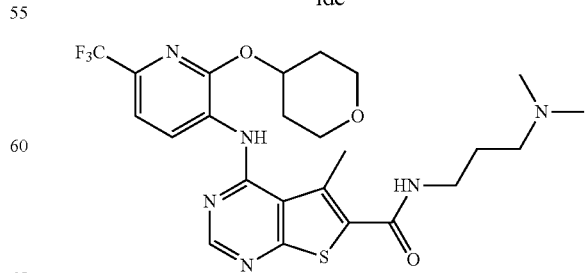

To a suspension of methyl 4-(2-(tetrahydro-2H-pyran-4-yloxy)-6-(trifluoromethyl)-pyridin-3-ylamino)-5-methylthieno[2,3-d]pyrimidine-6-carboxylate (0.139 g, 0.29 mmol) in EtOH/THF (5 mL; 3:2) was added aqueous sodium hydroxide (2 M, 0.625 mL, 1.25 mmol) and the reaction mixture stirred at ambient temperature for 24 hours. The mixture was diluted with DCM and 10% aqueous KHSO$_4$ and the mixture separated. The organic phase was washed with brine, dried (MgSO$_4$) and the solvent removed in vacuo. The residue was diluted with DMF (2.0 mL) and cooled in ice-water. Hünig's base (44 L, 0.25 mmol) and HATU (0.105 g, 0.28 mmol) were added and the mixture was stirred at this temperature for 20 minutes when 3-(dimethylamino)-propylamine (0.136 mL, 1.24 mmol) was added. The coolant was removed and the reaction stirred at ambient temperature for 18 hours. The mixture was diluted with EtOAc, washed with water and with brine (×2). The organic phase was dried (MgSO$_4$), filtered and the solvent removed in vacuo. The residue was purified by flash column chromatography (100% iso-hexane→100% DCM→250:10:1 DCM/MeOH/NH$_4$OH) followed by trituration of the major component with diethyl ether to afford the title compound as off-white solid (0.01 g, 8%).

$^1$H NMR (400 MHz; CDCl$_3$; 25° C.): δ 9.29 (d, 1H), 9.09 (s, 1H), 8.69 (s, 1H), 8.55 (br s, 1H), 7.37 (d, 1H), 5.43-5.37 (m, 1H), 4.05-4.01 (m, 2H), 3.67-3.56 (m, 4H), 3.14 (s, 3H), 2.56-2.54 (m, 2H), 2.32 (s, 6H), 2.24-2.21 (m, 2H), 1.89-1.76 (m, 4H). MS (ESI$^+$): 539 (M+H). HPLC (10 cm_ESI_formic): Rt 2.43 min (HPLC purity 98%).

solvent removed in vacuo. The residue was triturated with n-hexane to afford the title compound as an off-white solid (0.197 g, 66%).

$^1$H NMR (400 MHz; CDCl$_3$; 25° C.): δ 8.33-8.31 (m, 1H), 8.06-8.05 (m, 1H), 7.65 (m, 1H), 7.13-7.11 (m, 1H), 6.85-6.84 (m, 1H), 5.60-5.55 (m, 1H), 4.06-4.02 (m, 2H), 3.73-3.67 (m, 2H), 2.16-2.09 (m, 2H), 1.99-1.91 (m, 2H).

Preparation of 6-(furan-3-yl)-2-(tetrahydro-2H-pyran-4-yloxy)pyridin-3-amine

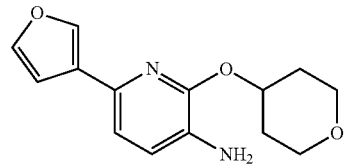 [SMILES: Nc1ccc(-c2ccoc2)nc1OC1CCOCC1]

Prepared as described for 2-(tetrahydro-2H-pyran-4-yloxy)-5-(trifluoromethyl)pyridin-3-amine to afford the title compound as an oil (0.162 g, 94%).

$^1$H NMR (400 MHz; CDCl$_3$; 25° C.): δ 7.81 (m, 1H), 7.42 (m, 1H), 6.90 (s, 2H), 6.75 (m, 1H), 5.39-5.35 (m, 1H), 4.03-3.98 (m, 2H), 3.78 (br s, 2H), 3.68-3.62 (m, 2H), 2.16-2.12 (m, 2H), 1.89-1.81 (m, 2H).

General Scheme 5

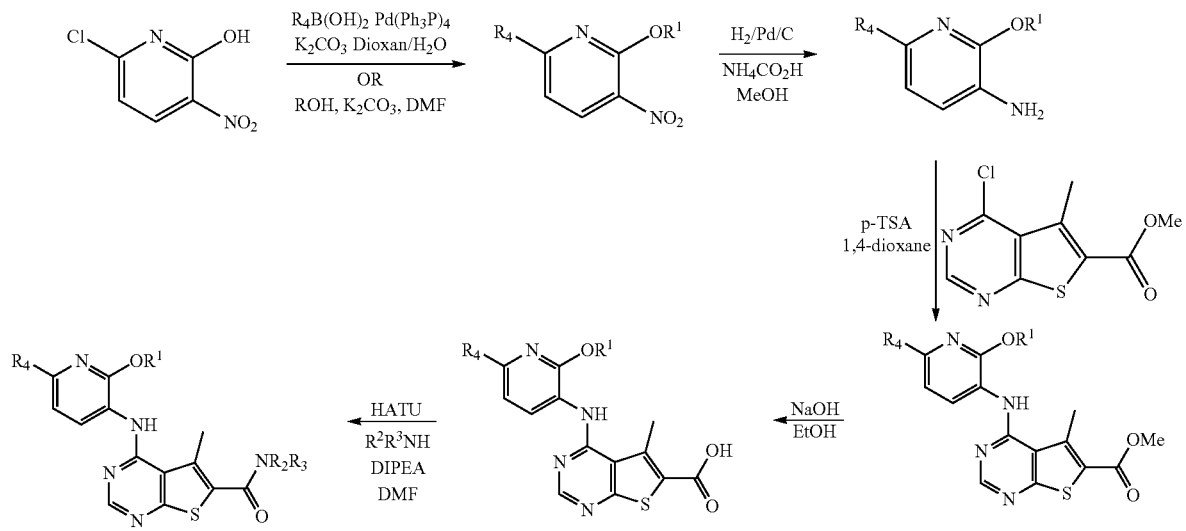

Preparation of 6-(furan-3-yl)-3-nitro-2-(tetrahydro-2H-pyran-4-yloxy)pyridine

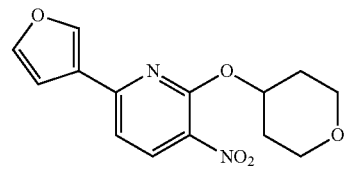

A solution of 6-chloro-3-nitro-2-(tetrahydro-2H-pyran-4-yloxy)pyridine (0.259 g, 1.00 mmol), furan-3-boronic acid (0.123 g, 1.10 mmol), tetrakis(triphenylphosphine)palladium(0) (0.058 g, 0.05 mmol) and potassium carbonate (0.276 g, 2.00 mmol) in 1,4-dioxane/water (5 mL, 4:1) was de-gassed with nitrogen and then heated at 80° C. for 18 hours. The reaction mixture was diluted with EtOAc, washed with water and brine. The organic phase was dried (MgSO$_4$) and the Example 35

Methyl 4-(6-(furan-3-yl)-2-(tetrahydro-2H-pyran-4-yloxy)pyridin-3-ylamino)-5-methylthieno[2,3-d]pyrimidine-6-carboxylate

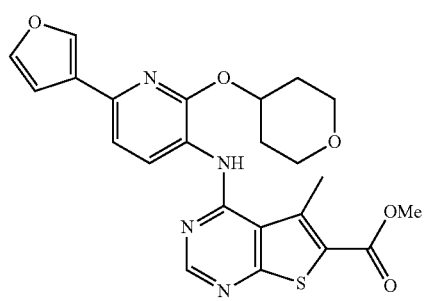 [SMILES: COC(=O)c1sc2ncnc(Nc3ccc(-c4ccoc4)nc3OC3CCOCC3)c2c1C]

Prepared as described for methyl 4-(6-chloro-2-(tetrahydro-2H-pyran-4-yloxy)pyridin-3-ylamino)-5-methylthieno[2,3-d]pyrimidine-6-carboxylate to afford the title compound as a red solid (0.155 g, 56%).

¹H NMR (400 MHz; CDCl₃; 25° C.): δ 9.08 (d, 1H), 8.69 (s, 1H), 8.42 (s, 1H), 7.93 (s, 1H), 7.48 (m, 1H), 7.15 (d, 1H), 6.82 (m, 1H), 5.48-5.42 (m, 1H), 4.09-4.04 (m, 2H), 3.95 (s, 3H), 3.69-3.63 (m, 2H), 3.18 (s, 3H), 2.26-2.23 (m, 2H), 1.92-1.83 (m, 2H). MS (ESI⁺): 467 (M+H). HPLC (10 cm_ESI_formic): Rt 4.63 min (HPLC purity 99%).

Example 36

N-(3-(Dimethylamino)propyl)-4-(6-(furan-3-yl)-2-(tetrahydro-2H-pyran-4-yloxy)pyridin-3-ylamino)-5-methylthieno[2,3-d]pyrimidine-6-carboxamide

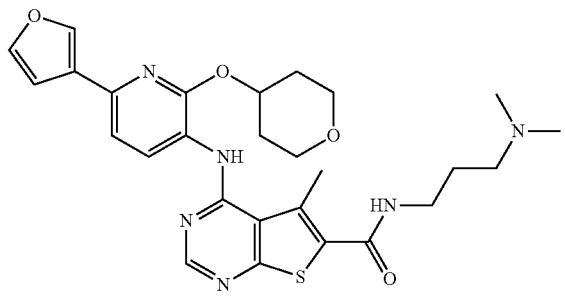 [SMILES: Cc1c(C(=O)NCCCN(C)C)sc2ncnc(Nc3ccc(-c4ccoc4)nc3OC3CCOCC3)c12]

To a suspension of methyl 4-(6-(furan-3-yl)-2-(tetrahydro-2H-pyran-4-yloxy)pyridin-3-ylamino)-5-methylthieno[2,3-d]pyrimidine-6-carboxylate (0.155 g, 0.33 mmol) in EtOH/THF (5 mL, 3:2) was added aqueous sodium hydroxide (2M, 0.714 mL, 1.43 mmol) and the reaction mixture stirred at ambient temperature for 24 hours. The mixture was diluted with DCM and 10% aqueous KHSO₄ and the organic layer separated. The organic phase was washed with brine, dried (MgSO₄) and the solvent removed in vacuo. The residue was diluted with DMF (2.0 mL) and cooled in ice-water. Hünig's base (32 L, 0.18 mmol) and HATU (0.076 g, 0.20 mmol) were added and the mixture was stirred at this temperature for 20 minutes when 3-(dimethylamino)-propylamine (0.100 mL, 0.91 mmol) was added. The coolant was removed and the reaction stirred at ambient temperature for 18 hours. The mixture was diluted with EtOAc, washed with water and brine (×2). The organic phase was dried (MgSO₄), filtered and the solvent was removed in vacuo. The residue was purified by SCX-2 ion exchange chromatography to afford the title compound as an off-white solid (0.02 g, 11%).

¹H NMR (400 MHz; CDCl₃; 25° C.): δ 9.08 (d, 1H), 8.95 (br s, 1H), 8.64 (s, 1H), 8.41 (s, 1H), 7.92 (m, 1H), 7.48 (m, 1H), 7.15 (d, 1H), 6.82 (m, 1H), 5.45-5.38 (m, 1H), 4.07-4.02 (m, 2H), 3.68-3.49 (m, 4H), 2.59-2.56 (m, 2H), 2.34 (s, 6H), 2.26-2.21 (m, 2H), 1.91-1.76 (m, 4H). MS (ESI⁺): 537 (M+H). HPLC (10 cm_ESI_formic): Rt 2.39 min (HPLC purity 96%).

Preparation of 6-(3-methoxypropoxy)-3-nitro-2-(tetrahydro-2H-pyran-4-yloxy)pyridine

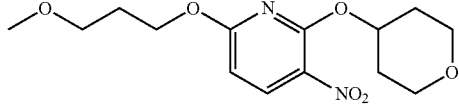

A mixture of 6-chloro-3-nitro-2-(tetrahydro-2H-pyran-4-yloxy)pyridine (0.259 g, 1.00 mmol), K₂CO₃ (0.276 g, 2.00 mmol) and 3-methoxy-1-propanol (0.191 mL, 2.00 mmol) in DMF (3.0 mL) was heated at 60° C. for 6 hours and then at 100° C. for 24 hours. The reaction mixture was diluted with EtOAc, washed with water and brine (×2). The organic phase was dried (MgSO₄), filtered and the solvent removed in vacuo. The residue was purified by flash column chromatography (100% iso-hexane 75% iso-hexane/EtOAc) to afford an oil (0.17 g, 54%).

¹H NMR (400 MHz; CDCl₃; 25° C.): δ 8.33 (d, 1H), 6.36 (d, 1H), 5.45 (m, 1H), 4.41 (t, 2H), 4.04-3.99 (m, 2H), 3.70-3.65 (m, 2H), 3.53 (t, 2H), 3.36 (s, 3H), 2.08-2.05 (m, 4H), 1.94-1.91 (m, 2H).

Preparation of 6-(3-methoxypropoxy)-2-(tetrahydro-2H-pyran-4-yloxy)pyridin-3-amine

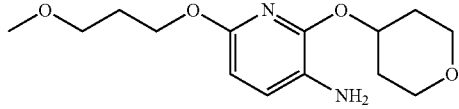 [SMILES: COCCCOc1ccc([N+](=O)[O-])c(OC2CCOCC2)n1]

Prepared as described for 2-(tetrahydro-2H-pyran-4-yloxy)-5-(trifluoromethyl)pyridin-3-amine to afford the title compound as an oil (0.135 g, 90%).

¹H NMR (400 MHz; CDCl₃; 25° C.): δ 6.96 (d, 1H), 6.18 (d, 1H), 5.22 (m, 1H), 4.21 (t, 2H), 4.00-3.96 (m, 2H), 3.65-3.59 (m, 2H), 3.55-3.51 (m, 2H), 3.39 (br s, 2H), 3.33 (s, 3H), 2.11-1.99 (m, 4H), 1.84-1.79 (m, 2H).

Example 37

Methyl 4-(6-(3-methoxypropoxy)-2-(tetrahydro-2H-pyran-4-yloxy)pyridin-3-ylamino)-5-methylthieno[2,3-d]pyrimidine-6-carboxylate

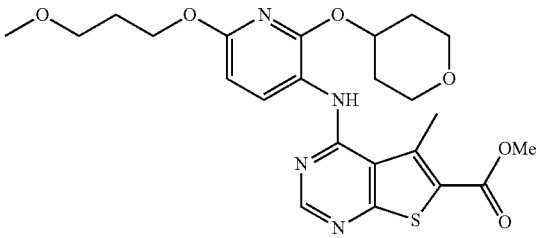 [SMILES: COCCCOc1ccc(Nc2ncnc3sc(C(=O)OC)c(C)c23)c(OC2CCOCC2)n1]

Prepared as described for methyl 4-(6-chloro-2-(tetrahydro-2H-pyran-4-yloxy)pyridin-3-ylamino)-5-methylthieno[2,3-d]pyrimidine-6-carboxylate to afford the title compound as off-white solid (0.053 g, 25%).

¹H NMR (400 MHz; CDCl₃; 25° C.): δ 8.91 (d, 1H), 8.59 (s, 1H), 8.04 (br s, 1H), 6.42 (d, 1H), 5.32-5.27 (m, 1H), 4.32-4.29 (t, 2H), 4.04-3.99 (m, 2H), 3.94 (s, 3H), 3.65-3.59 (m, 2H), 3.55 (t, 2H), 3.37 (s, 3H), 3.15 (s, 3H), 2.19-2.15 (m, 2H), 2.08-2.02 (m, 2H), 1.88-1.78 (m, 2H). MS (ESI⁺): 489 (M+H). HPLC (10 cm_ESI_formic): Rt 4.40 min (HPLC purity 99%).

Example 38

4-(6-(3-Methoxypropoxy)-2-(tetrahydro-2H-pyran-4-yloxy)pyridin-3-ylamino)-5-methylthieno[2,3-d]pyrimidine-6-carboxylic acid

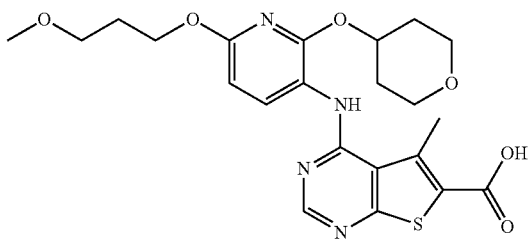 [SMILES: COCCCOc1ccc(Nc2ncnc3sc(C(=O)O)c(C)c23)c(OC2CCOCC2)n1]

Aqueous NaOH (2M, 0.175 mL) was added into a suspension of methyl 4-(6-(3-methoxypropoxy)-2-(tetrahydro-2H-pyran-4-yloxy)pyridin-3-ylamino)-5-methylthieno[2,3-d]pyrimidine-6-carboxylate (0.034 g, 0.07 mmol) and the reaction mixture stirred at ambient temperature for 18 hours. The solution was adjusted to pH 2 using 10% aqueous KHSO₄ and the resultant suspension was filtered. The solid was washed with water, diethyl ether and dried in vacuo over P₂O₅ to afford off-white solid (0.024 g, 73%).

¹H NMR (400 MHz; d₆-DMSO; 25° C.) 13.0 (br s, 1H), 8.52 (s, 1H), 8.48 (d, 1H), 8.32 (br s, 1H), 6.49 (d, 1H), 5.25-5.19 (m, 1H), 4.32-4.29 (m, 2H), 3.84-3.79 (m, 2H), 3.57-3.46 (m, 4H), 3.29 (s, 3H), 3.11 (s, 3H), 2.09-1.96 (m, 4H), 1.74-1.66 (m, 2H). MS (ESI⁺): 475 (M+H). HPLC (10 cm_ESI_formic): Rt 3.66 min (HPLC purity 99%).

Example 39

4-(6-(2-Methoxyethoxy)-2-(tetrahydro-2H-pyran-4-yloxy)pyridin-3-ylamino)-5-methylthieno[2,3-d]pyrimidine-6-carboxylic acid

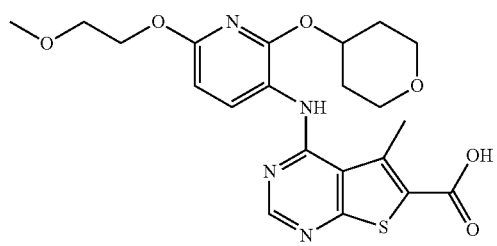 [SMILES: COCCOc1ccc(Nc2ncnc3sc(C(=O)O)c(C)c23)c(OC2CCOCC2)n1]

Prepared as described for 4-(6-(3-methoxypropoxy)-2-(tetrahydro-2H-pyran-4-yloxy)pyridin-3-ylamino)-5-methylthieno[2,3-d]pyrimidine-6-carboxylic acid except that 2-methoxyethanol was used in place of 3-methoxypropan-1-ol in the first step.

¹H NMR (400 MHz; d₆-DMSO; 25° C.) 13.5 (br s, 1H), 8.50 (d, 1H), 8.32 (br s, 1H), 6.51 (d, 1H), 5.24-5.19 (m, 1H), 4.38-4.36 (m, 2H), 3.84-3.79 (m, 2H), 3.71-3.69 (m, 2H), 3.57-3.51 (m, 2H), 3.34 (s, 3H), 3.11 (s, 3H), 2.08-2.05 (m, 2H), 1.74-1.66 (m, 2H). MS (ESI⁺): 461 (M+H). HPLC (10 cm_ESI_slow_formic): Rt 4.61 min (HPLC purity 91.5%).

Example 40

4-[4-Fluoro-2-(tetrahydro-2H-pyran-4-yloxy)-phenylamino]-5,8-dihydro-6H-pyrido[4',3':4,5]thieno[2,3-d]pyrimidine-7-carboxylic acid tert-butyl ester

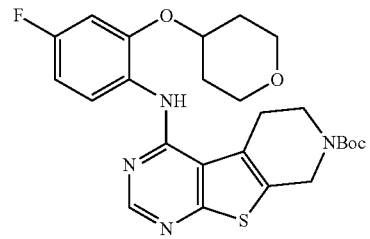 [SMILES: CC(C)(C)OC(=O)N1CCc2c(sc3ncnc(Nc4ccc(F)cc4OC4CCOCC4)c23)C1]

A solution of 4-chloro-5,8-dihydro-6H-pyrido[4',3':4,5]thieno[2,3-d]pyrimidine-7-carboxylic acid tert-butyl ester (prepared according to WO2007/109279, 0.141 g, 0.43 mmol), 4-fluoro-2-(tetrahydro-2H-pyran-4-yloxy)aniline (0.092 g, 0.44 mmol) and para-toluene sulfonic acid (0.08 g, 0.04 mmol) in 1,4-dioxane (2 mL) was purged with nitrogen and then heated at 120° C. for 5 hours. The reaction mixture was diluted with EtOAc, washed with 10% aqueous K₂CO₃ and brine. The organic phase was dried (MgSO₄), filtered and concentrated in vacuo. The residue was purified by flash column chromatography (100% iso-hexane→66% iso-hexane/EtOAc→100% EtOAc) followed by trituration with MeOH afforded the title compound as white solid (0.042 g, 20%).

¹H NMR (400 MHz; CDCl₃; 25° C.) 8.74-8.71 (m, 1H), 8.54 (s, 1H), 7.76 (br s, 1H), 6.78-6.69 (m, 2H), 4.72 (br s, 2H), 4.54 (m, 1H), 4.07-4.02 (m, 2H), 3.87-3.84 (m, 2H), 3.60-3.54 (m, 2H), 3.18 (m, 2H), 2.18-2.15 (m, 2H), 1.82-1.77 (m, 2H), 1.52 (s, 9H). MS (ESP): 501 (M+H). HPLC (10 cm_ESI_slow_formic): Rt 4.42 min (HPLC purity 99%).

Example 41

Preparation of [4-fluoro-2-(tetrahydro-2H-pyran-4-yloxy)-phenyl]-(5,6,7,8-tetrahydro-pyrido[4',3':4,5]thieno[2,3-d]pyrimidin-4-yl)-amine

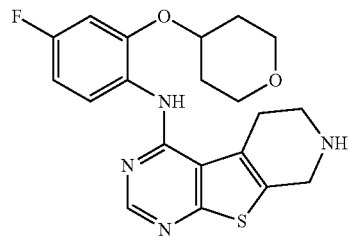 [SMILES: Fc1ccc(Nc2ncnc3sc4c(c23)CCNC4)c(OC2CCOCC2)c1]

Trifluoroacetic acid (0.50 mL) was added into a solution of 4-[4-fluoro-2-(tetrahydro-2H-pyran-4-yloxy)-phenylamino]-5,8-dihydro-6H-pyrido[4',3':4,5]thieno[2,3-d]pyrimidine-7-carboxylic acid tert-butyl ester (0.031 g, 0.06 mmol) in DCM (1 mL) and the reaction mixture was stirred at ambient temperature for 2 hours. The reaction mixture was diluted with DCM and washed with 2M NaOH. The organic phase was dried (MgSO$_4$), filtered and concentrated in vacuo. The residue was washed with hexane to afford the title compound as a white solid (0.016 g, 65%).

$^1$H NMR (400 MHz; CHCl$_3$; 25° C.) 8.78-8.74 (m, 1H), 8.53 (s, 1H), 7.82 (s, 1H), 6.79-6.68 (m, 2H), 4.57-4.50 (m, 1H), 4.14-4.13 (m, 2H), 4.07-4.02 (m, 2H), 3.60-3.54 (m, 2H), 3.33-3.30 (m, 2H), 3.14-3.11 (m, 2H), 2.19-2.14 (m, 2H), 1.83-1.74 (m, 2H), 1.59 (br s, 1H). MS (ESI$^+$): 401 (M+H). HPLC (10 cm_ESCI_bicarb): Rt 3.52 min (HPLC purity 99%).

Example 42

Preparation of 2-dimethylamino-1-{4-[4-fluoro-2-(tetrahydro-2H-pyran-4-yloxy)-phenylamino]-5,8-dihydro-6H-pyrido[4',3':4,5]thieno[2,3-d]pyrimidin-7-yl}-ethanone

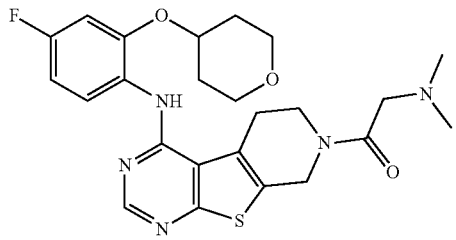 [SMILES: CN(C)CC(=O)N1CCc2c(sc3ncnc(Nc4ccc(F)cc4OC4CCOCC4)c23)C1]

HATU (0.285 g, 0.75 mmol) was added into a stirred solution of Hünig's base (0.13 mL, 0.75 mmol) and N,N-dimethylglycine (0.077 g, 0.75 mmol) in DMF (1.0 mL) and the mixture stirred for 20 minutes at ambient temperature. [4-Fluoro-2-(tetrahydro-2H-pyran-4-yloxy)-phenyl]-(5,6,7,8-tetrahydro-pyrido[4',3':4,5]thieno[2,3-d]pyrimidin-4-yl)-amine (0.10 g, 0.25 mmol) was added and the mixture stirred for 18 hours. Water (5 mL) was added and the mixture stirred for 20 minutes. The precipitated solid was collect by filtration, washed with water (10 mL), diethyl ether (10 mL), and dried under vacuum to give a colourless solid (0.049 g, 40%).

$^1$H NMR (400 MHz; d$_6$-DMSO; 125° C.): δ 8.50 (s, 1H), 8.39 (t, 1H), 7.82 (bs, 1H), 7.09 (dd, 1H), 6.84 (dt, 1H), 4.89 (s, 2H), 4.80-4.70 (m, 1H), 4.30 (s, 2H), 3.99-3.90 (m, 2H), 3.89-3.84 (m, 2H), 3.60-3.50 (m, 2H), 3.35-3.30 (2H, m), 2.97 (s, 6H), 2.15-2.05 (m, 2H), 1.75-1.70 (m, 2H). MS (ESI$^+$): 486 (M+H). HPLC (10 cm_ESI_formic): Rt 2.15 min (HPLC purity 98%).

Example 43

Preparation of [4-Fluoro-2-(tetrahydro-2H-pyran-4-yloxy)-phenyl]-(5,7-dihydro-1H-pyrrolo[3',4':4,5]thieno[2,3-d]pyrimidin-4-yl)-amine

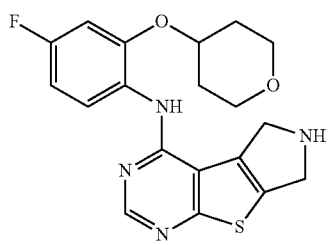 [SMILES: Fc1ccc(Nc2ncnc3sc4c(c23)CNC4)c(OC2CCOCC2)c1]

A solution of 4-chloro-5,7-dihydro-1H-pyrolo[3',4':4,5]thieno[2,3-d]pyrimidine-6-carboxylic acid benzyl ester (prepared in an analogous fashion to 4-chloro-5,8-dihydro-6H-pyrido[4',3':4,5]thieno[2,3-d]pyrimidine-7-carboxylic acid tert-butyl ester, WO2007/109279, 0.135 g, 0.39 mmol), 4-fluoro-2-(tetrahydro-2H-pyran-4-yloxy)aniline (0.090 g, 0.39 mmol) and para-toluene sulfonic acid (0.08 g, 0.04 mmol) in 1,4-dioxane (2 mL) was purged with nitrogen and heated at 120° C. for 21 hours. The reaction mixture was diluted with EtOAc, washed with 10% aqueous K$_2$CO$_3$ and brine. The organic phase was dried (MgSO$_4$), filtered and concentrated in vacuo. The residue was purified by flash column chromatography (100% iso-hexane→100% DCM→3% MeOH/DCM→200:10:1 DCM/MeOH/NH$_4$OH) to afford the title compound as white solid (0.015 g, 10%).

$^1$H NMR (400 MHz; CHCl$_3$; 25° C.) 8.76-8.72 (m, 1H), 8.55 (s, 1H), 7.38 (s, 1H), 6.79-6.87 (m, 2H), 4.56-4.49 (m, 3H), 4.40-4.38 (m, 2H), 4.08-4.03 (m, 2H), 3.59-3.53 (m, 2H), 2.18-2.15 (m, 2H), 1.84 (br s, 1H), 1.87-1.78 (m, 2H). MS (ESI$^+$): 387 (M+H). HPLC (10 cm_ESCI_bicarb): Rt 3.13 min (HPLC purity 98.4%).

General Scheme 6

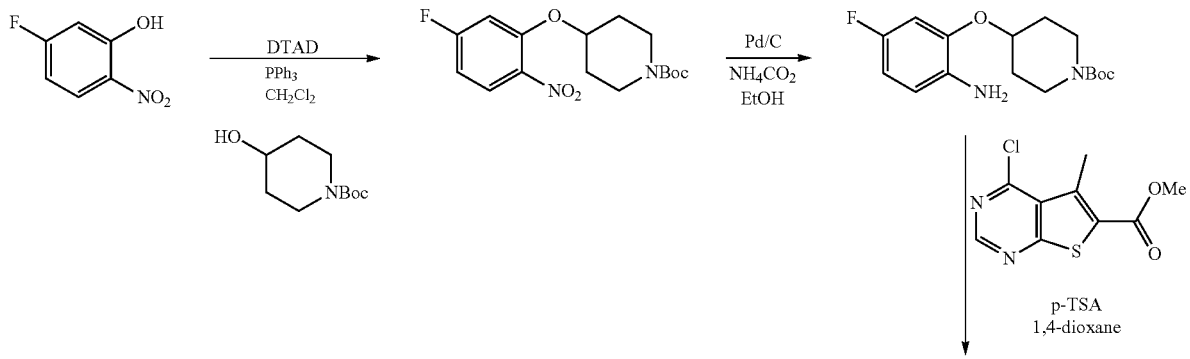

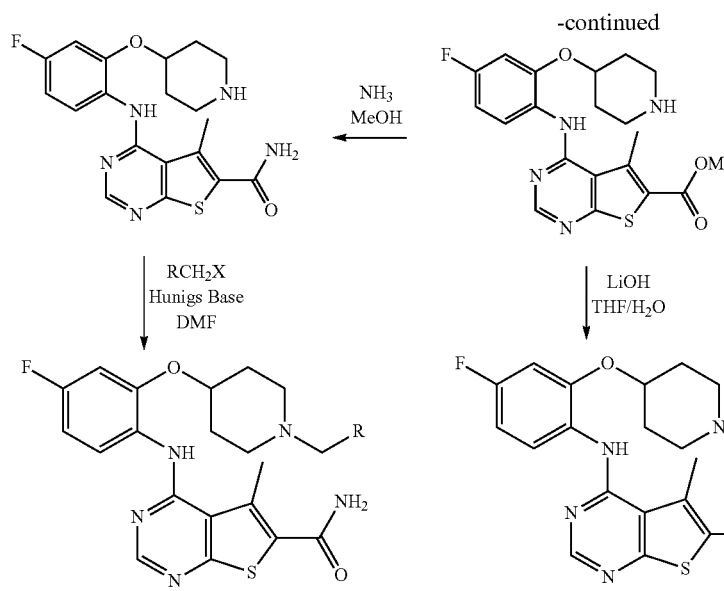
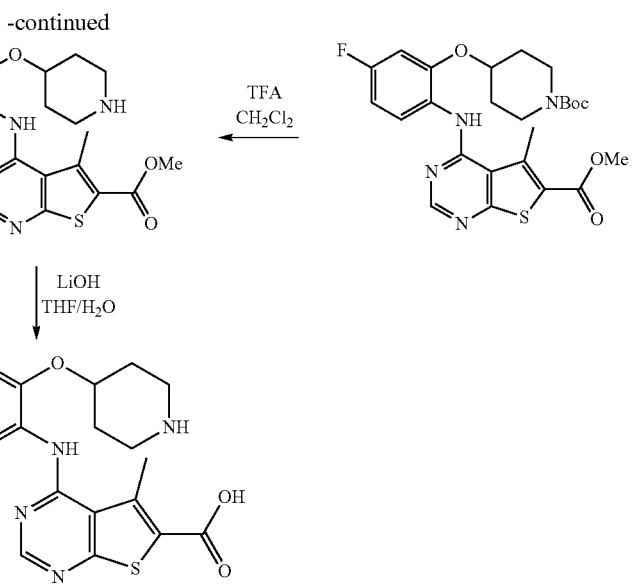

Preparation of tert-butyl 4-(5-fluoro-2-nitrophenoxy)piperidine-1-carboxylate

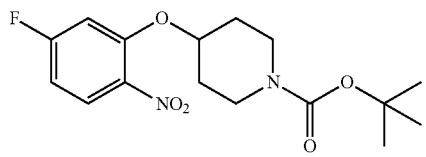

Di-tert-butyl azodicarboxylate (5.27 g, 23.0 mmol) in DCM (10 mL) was added into a solution of 5-fluoro-2-nitrophenol (10 g, 63.7 mmol), tert-butyl 4-hydroxypiperidine-1-carboxylate (4.22 g, 21.0 mmol) and triphenyl phosphine (6.0 g, 23.0 mmol) in anhydrous DCM (40 mL) at 0° C. The solution was allowed to warm to ambient temperature overnight, concentrated in vacuo and the crude product triturated with n-pentane/diethyl ether (×2) to remove the triphenyl phosphine oxide by-product. The sample was purified by dry flash chromatography (1:10→1:1 EtOAc/iso-hexane) to yield yellow oil (2.6 g, 40%).

$^1$H NMR (400 MHz; CDCl$_3$; 25° C.): δ 7.93 (1H, dd), 6.78-6.71 (2H, m), 4.67-4.63 (1H, m), 3.59-3.52 (4H, m), 1.92-1.87 (4H, m), 1.47 (s, 9H).

Preparation of tert-butyl 4-(2-amino-5-fluorophenoxy)piperidine-1-carboxylate

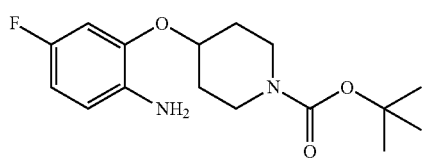 [SMILES: CC(C)(C)OC(=O)N1CCC(Oc2cc(F)ccc2[N+](=O)[O-])CC1]

Ammonium formate (1.2 g, 19.1 mmol) was added into a suspension of tert-butyl 4-(5-fluoro-2-nitrophenoxy)piperidine-1-carboxylate (2.0 g, 5.8 mmol) and palladium on carbon (5%, 0.4 g) in MeOH (30 mL) at ambient temperature. The solution was stirred for 0.5 hours, filtered through Celite and washed with MeOH. The filtrate was concentrated in vacuo and triturated from diethyl ether to remove the ammonium formate by-products. The sample was purified by flash column chromatography (1:10→1:1 EtOAc/DCM) to yield a colourless oil which crystallised from diethyl ether/petroleum ether (40-60° C.) as a colourless solid (1.6 g, 87%).

$^1$H NMR (400 MHz; CDCl$_3$; 25° C.): δ 6.62-6.55 (m, 3H), 4.43-4.39 (m, 1H), 3.82-3.75 (m, 2H), 3.34-3.29 (m, 2H), 1.97-1.93 (m, 2H), 1.79-1.75 (m, 2H), 1.47 (s, 9H).

Example 44

Preparation of methyl 4-(2-(1-(tert-butoxycarbonyl)piperidin-4-yloxy)-4-fluorophenylamino)-5-methylthieno[2,3-d]pyrimidine-6-carboxylate

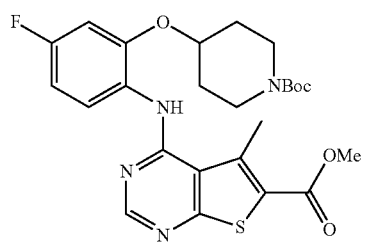 [SMILES: COC(=O)c1sc2ncnc(Nc3ccc(F)cc3OC3CCN(C(=O)OC(C)(C)C)CC3)c2c1C]

tert-Butyl 4-(2-amino-5-fluorophenoxy)piperidine-1-carboxylate (0.865 g, 2.8 mmol), methyl 4-chloro-5-methylthieno[2,3-d]pyrimidine-6-carboxylate (0.675 g, 2.8 mmol) and para-toluene sulfonic acid (0.026 g, 0.14 mmol) were heated at 90° C. in anhydrous 1,4-dioxane (8 mL) for 1.5 hours. The solution was cooled to ambient temperature, diluted with water (2 mL) and adjusted to pH 10 (4:1 water/ammonium hydroxide solution). The precipitate was collected, washed with water and diethyl ether to yield the title compound as yellow solid (0.95 g, 65%).

$^1$H NMR (400 MHz; d$_6$-DMSO; 25° C.): δ 8.58 (s, 1H), 8.50 (bs, 1H), 8.37 (dd, 1H), 7.21 (dd, 1H), 6.89 (dt, 1H), 4.75-4.72 (m, 1H), 3.91 (s, 3H), 3.72-3.67 (m, 2H), 3.15-3.09 (m, 5H), 2.10-1.89 (m, 2H), 1.55-1.49 (m, 2H), 1.43 (s, 9H).

Example 45

Methyl 4-(4-fluoro-2-(piperidin-4-yloxy)phenylamino)-5-methylthieno[2,3-c]pyrimidine-6-carboxylate

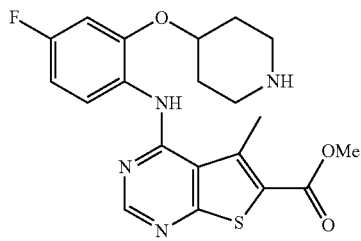 [SMILES: COC(=O)c1sc2ncnc(Nc3ccc(F)cc3OC3CCNCC3)c2c1C]

To a suspension of 4-(2-(1-(tert-butoxycarbonyl)piperidin-4-yloxy)-4-fluorophenyl-amino)-5-methylthieno[2,3-d]pyrimidine-6-carboxylate (0.8 g, 1.5 mmol) in DCM (4 mL) at 0° C. was added trifluoroacetic acid (4.0 mL) and the mixture stirred for 4 hours. The solvent was removed in vacuo, the residue re-suspended in DCM and the solution adjusted to pH 9 with 2N sodium carbonate solution. The mixture was passed through a PTFE separation frit and the filtrate concentrated in vacuo to give beige solid (0.72 g, 96%).

$^1$H NMR (400 MHz; $d_6$-DMSO; 25° C.): δ 8.62 (s, 1H), 8.58 (s, 1H), 8.49 (bs, 2H), 8.29 (dd, 1H), 7.23 (dd, 1H), 6.90 (dt, 1H), 4.82-4.78 (m, 1H), 3.90 (s, 3H), 3.30-3.20 (m, 2H), 3.12 (s, 3H), 3.10-3.00 (m, 2H), 2.20-2.10 (m, 2H), 1.90-1.75 (m, 2H). MS (ESI$^+$): 417 (M+H). HPLC (10 cm_esci_bicarb): Rt 3.68 min (HPLC purity 93%).

Example 46

4-(4-Fluoro-2-(piperidin-4-yloxy)phenylamino)-5-methylthieno[2,3-d]pyrimidine-6-carboxylic acid

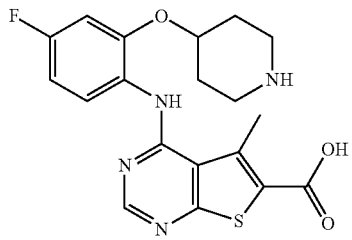

Lithium hydroxide monohydrate (0.05 g, 1.2 mmol) in water (1.0 mL) was added into a stirred suspension of methyl 4-(4-fluoro-2-(piperidin-4-yloxy)phenylamino)-5-methylthieno[2,3-d]pyrimidine-6-carboxylate (0.10 g, 0.2 mmol) in THF (3 mL) and the reaction stirred at ambient temperature overnight. The solution was cooled in an ice-bath and 2N hydrochloric acid added until the solution reached pH 5. The precipitate was collected, washed with water and dried over $P_2O_5$ to yield colourless solid (0.056 g, 58%).

$^1$H NMR (400 MHz; $d_6$-DMSO; 25° C.): δ 8.72 (dd, 1H), 8.49 (s, 1H), 8.39 (bs, 1H), 7.24 (dd, 1H), 6.89 (dt, 1H), 4.85-4.81 (m, 1H), 3.60-3.30 (m, 2H), 3.19 (s, 3H), 3.08 (t, 2H), 2.29-2.27 (m, 2H), 2.12-2.04 (m, 2H). MS (ESI$^+$): 404 (M+H). HPLC (10 cm_esci_bicarb): Rt 2.40 min (HPLC purity 98%).

Example 47

4-(4-Fluoro-2-(piperidin-4-yloxy)phenylamino)-5-methylthieno[2,3-d]pyrimidine-6-carboxamide

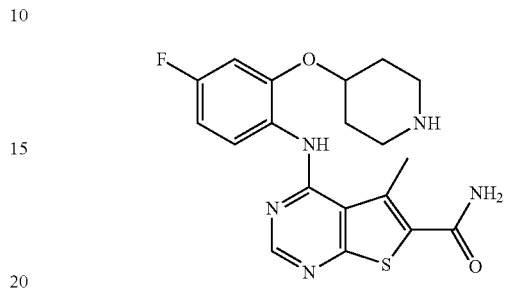

A suspension of methyl 4-(4-fluoro-2-(piperidin-4-yloxy) phenylamino)-5-methylthieno[2,3-d]pyrimidine-6-carboxylate (0.1 g, 0.2 mmol) in 7N ammonia in MeOH (6 mL) was heated in a sealed tube at 120° C. for 18 hours. After cooling to ambient temperature the precipitated solid was collected by filtration, washed with cold MeOH and dried under vacuum to give beige solid (0.035 g, 36%).

$^1$H NMR (400 MHz; $d_6$-DMSO; 25° C.): δ 8.56 (s, 1H), 8.53 (dd, 1H), 8.43 (bs, 1H), 7.91 (bs, 1H), 7.89 (bs, 1H), 7.20 (dd, 1H), 6.87 (dt, 1H), 4.85-4.81 (m, 1H), 3.60-3.30 (m, 2H), 3.19 (s, 3H), 3.08 (t, 2H), 2.29-2.27 (m, 2H), 2.12-2.04 (m, 2H). MS (ESI$^+$): 402 (M+H). HPLC (10 cm_esci_bicarb): Rt 2.81 min (HPLC purity 94%).

Example 48

4-(2-(1-((1,2,4-Oxadiazol-3-yl)methyl)piperidin-4-yloxy)-4-fluorophenylamino)-5-methylthieno[2,3-d]pyrimidine-6-carboxamide

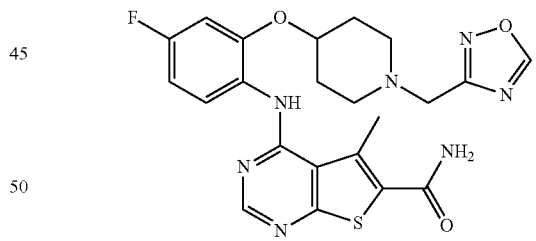

To a suspension of methyl 4-(4-fluoro-2-(piperidin-4-yloxy)phenylamino)-5-methylthieno[2,3-d]pyrimidine-6-carboxamide (0.06 g, 0.15 mmol) in DMF (2.0 mL) was added Hünigs base (0.06 mL, 0.35 mmol) and 3-(chloromethyl)-1,2,4-oxadiazole (0.035 g, 0.3 mmol) and the mixture was warmed to 60° C. for 18 hours. After cooling to ambient temperature water (2 mL) was added and the mixture stirred for 0.5 hours. The precipitated solid was collected by filtration and triturated from boiling MeCN. The solid was collected by filtration and dried under vacuum to give beige solid (0.046 g, 63%).

$^1$H NMR (400 MHz; $d_6$-DMSO; 25° C.): δ 9.58 (s, 1H), 8.55 (s, 1H), 8.48 (t, 1H), 8.39 (s, 1H), 7.40 (bs, 2H), 7.18 (d, 1H), 6.86 (t, 1H), 4.58-4.53 (m, 1H), 3.75 (s, 2H), 2.98 (s,

3H), 2.87-2.80 (m, 2H), 2.42 (t, 2H), 2.12-2.05 (m, 2H), 1.75-1.69 (m, 2H). MS (ESI+): 484 (M+H). HPLC (10 cm_esci_bicarb): Rt 2.87 min (HPLC purity 95%).

Example 49

4-(4-Fluoro-2-(tetrahydro-2H-pyran-4-yloxy)phenylamino)-5-methylthieno[2,3-d]pyrimidine-6-carbonitrile

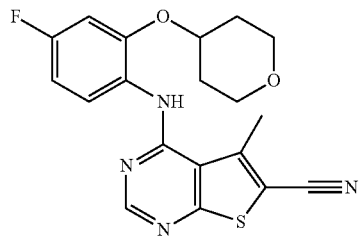 [SMILES: Cc1c(C#N)sc2ncnc(Nc3ccc(F)cc3OC3CCOCC3)c12]

To a stirred suspension of 4-(4-fluoro-2-(tetrahydro-2H-pyran-4-yloxy)phenylamino)-5-methylthieno[2,3-d]pyrimidine-6-carboxamide (0.1 g, 0.25 mmol) in DCM/pyridine (2.5 mL; 4:1) was added trifluoroacetic anhydride (0.138 mL, 1.0 mmol) at 0° C. and the mixture stirred for 4 hours. The reaction was quenched with ice and adjusted to pH 7 with saturated sodium hydrogen carbonate solution. The mixture was partitioned between DCM (10 mL) and water (10 mL). The aqueous phase was washed with DCM (10 mL) and the combined organic layers dried (MgSO$_4$) filtered and concentrated in vacuo. The crude product was purified by flash column chromatography (DCM→49:1 DCM/MeOH) to give the title compound as a pale yellow solid (0.065 g, 68%) after crystallisation from MeOH.

$^1$H NMR (400 MHz; CDCl$_3$; 25° C.): δ 8.73 (dd, 1H), 8.65 (s, 1H), 8.13 (bs, 1H), 6.78-6.70 (m, 2H), 4.62-4.50 (m, 1H), 4.06 (dt, 2H), 3.56 (dt, 2H), 2.95 (s, 3H), 2.22-2.15 (d, 2H), 1.82-1.79 (m, 2H). MS (ESI+): 385 (M+H). HPLC (10 cm_esci_BICARB): Rt 4.01 min (HPLC purity 99%).

Example 50

N-(4-Fluoro-2-(tetrahydro-2H-pyran-4-yloxy)phenyl)-5-methyl-6-(1H-tetrazol-5-yl)thieno[2,3-d]pyrimidin-4-amine

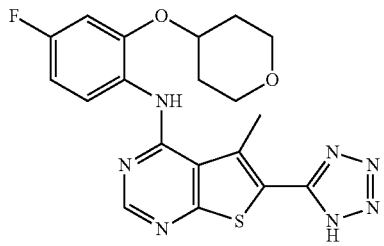 [SMILES: Cc1c(-c2nnn[nH]2)sc2ncnc(Nc3ccc(F)cc3OC3CCOCC3)c12]

To a stirred solution of 4-(4-fluoro-2-(tetrahydro-2H-pyran-4-yloxy)phenylamino)-5-methylthieno[2,3-d]pyrimidine-6-carbonitrile (0.036 g, 0.093 mmol) in DMF (1.0 mL) was added sodium azide (0.012 g, 0.18 mmol) and ammonium chloride (0.01 g, 0.18 mmol) and the mixture heated at 125° C. for 1.5 hours. The solvent was concentrated in vacuo and the residue co-evaporated with toluene. The crude product was dissolved in 10% MeOH in DCM and the insoluble material removed by filtration. The residue was triturated from MeCN, the solid collected and dried under vacuum. The solid was purified by reverse phase preparative HPLC to give the product as beige solid after lyophilisation (0.021 g, 54%).

$^1$H NMR (400 MHz; d$_6$-DMSO; 25° C.): δ 8.61 (dd, 1H), 8.51 (s, 1H), 8.47 (bs, 1H), 7.22 (dd, 1H), 4.82-4.79 (m, 1H), 3.91 (dt, 2H), 3.50 (dt, 2H), 3.21 (s, 3H), 2.10 (d, 2H), 1.72-1.61 (m, 2H). MS (ESI+): 428 (M+H). HPLC (10 cm_esci_BICARB): Rt 2.87 min (HPLC purity 98%).

Example 51

4-(4-Carbamoyl-2-(tetrahydro-2H-pyran-4-yloxy)phenylamino)-5-methylthieno[2,3-d]pyrimidine-6-carboxylic acid

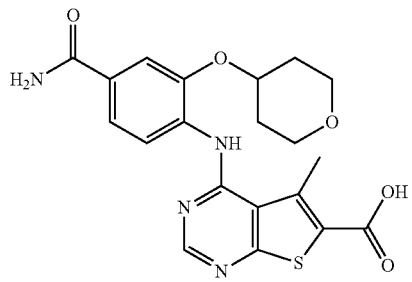 [SMILES: Cc1c(C(=O)O)sc2ncnc(Nc3ccc(C(N)=O)cc3OC3CCOCC3)c12]

Prepared from methyl 4-(4-carbamoyl-2-(tetrahydro-2H-pyran-4-yloxy)phenylamino)-5-methylthieno[2,3-d]pyrimidine-6-carboxylate in an analogous fashion to that given in general route 2. Yield (0.112 g, 57%)

$^1$H NMR (400 MHz; d$_6$-DMSO; 25° C.): δ 8.82-8.79 (m, 2H), 8.70 (s, 1H), 8.47 (bs, 1H), 8.04 (bs, 1H), 7.68 (bs, 1H), 7.63 (dd, 1H), 7.41 (bs, 1H), 4.87-4.82 (m, 1H), 3.94 (dt, 2H), 3.53 (t, 2H), 3.17 (s, 3H), 2.17-2.11 (m, 2H), 1.73-1.68 (m, 2H). MS (ESI+): 429 (M+H). HPLC (10 cm_ESI_Formic): Rt 2.54 min (HPLC purity 92%).

Example 52

6-Chloro-N-(4-fluoro-2-(tetrahydro-2H-pyran-4-yloxy)phenyl)-5-methylthieno[2,3-d]pyrimidin-4-amine

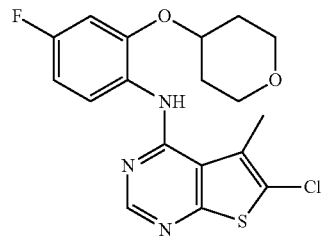 [SMILES: Cc1c(Cl)sc2ncnc(Nc3ccc(F)cc3OC3CCOCC3)c12]

4-Fluoro-2-(tetrahydro-2H-pyran-4-yloxy)aniline (0.057 g, 0.27 mmol), 4,6-dichloro-5-methylthieno[2,3-d]pyrimidine (0.06 g, 0.27 mmol, CA56844-14-5) and para-toluene sulfonic acid (0.005 g, 0.03 mmol) were heated at 90° C. in anhydrous 1,4-dioxane (1.5 mL) for 18 hours. The solution was cooled to ambient temperature, diluted with water (2 mL)

and adjusted to pH 10 (4:1 water/ammonium hydroxide solution). The precipitate was collected, washed with water and diethyl ether to yield the title compound as yellow solid (0.012 g, 11%).

$^1$H NMR (400 MHz; CDCl$_3$; 25° C.): δ 8.75-8.70 (m, 1H), 8.53 (s, 1H), 8.01 (s, 1H), 6.75-6.70 (m, 2H), 4.57-4.48 (m, 1H), 4.09-4.01 (m, 2H), 3.59-3.50 (m, 2H), 2.71 (s, 3H), 2.19-2.10 (m, 2H), 1.83-1.78 (m, 2H). MS (ESI$^+$): 394 (M+H). HPLC (10 cm_ESI_Formic): Rt 4.55 min (HPLC purity 97%).

Example 53

N-(3-(Dimethylamino)propyl)-4-(4-fluoro-2-iso-propoxyphenylamino)-5-methylthieno[2,3-d]pyrimidine-6-carboxamide

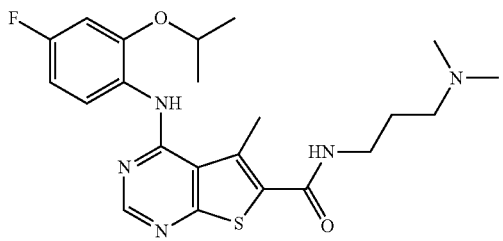 [SMILES: Cc1c(C(=O)NCCCN(C)C)sc2ncnc(Nc3ccc(F)cc3OC(C)C)c12]

Prepared from 4-(4-fluoro-2-iso-propoxyphenylamino)-5-methylthieno[2,3-d]pyrimidine-6-carboxylic acid in an analogous fashion to that given in general route 1. Yield (0.125 g, 65%)

$^1$H NMR (400 MHz; d$_6$-DMSO; 25° C.): δ 8.65-8.53 (m, 3H), 8.45 (bs, 1H), 7.14 (dd, 1H), 6.87 (dt, 1H), 4.86-4.82 (m, 1H), 3.35-3.28 (2H, m), 2.96 (s, 3H), 2.32 (t, 2H), 2.18 (s, 6H), 1.75-1.68 (m, 2H), 1.36 (d, 6H). MS (ESI$^+$): 446 (M+H). HPLC (10 cm_ESI_formic): Rt 2.29 min (HPLC purity 96%).

Preparation of 5-methyl-4-oxo-3,4-dihydrothieno[2,3-d]pyrimidine-6-sulfonyl chloride

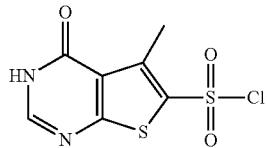

5-Methylthieno[2,3-d]pyrimidin-4(3H)-one (2 g, 12 mmol) was added portionwise into chlorosulfonic acid (8.0 mL, 120 mmol) maintaining the internal temperature below 0° C. After addition the reaction was stirred for 10 minutes, thionyl chloride (4.4 mL, 60 mmol) added drop wise, the mixture stirred for 0.5 hours at ambient temperature and then at reflux for 2 hours. The solution was poured onto crushed ice, the precipitated solid collected by filtration, washed with ice-water, and dried under vacuum to give cream solid. (1.1 g, 34%).

$^1$H NMR (400 MHz; d$_6$-DMSO; 25° C.): δ 12.40 (br s, 1H), 8.07 (s, 1H), 2.61 (s, 3H).

Preparation of N-(3-(dimethylamino)propyl)-5-methyl-4-oxo-3,4-dihydrothieno[2,3-d]pyrimidine-6-sulfonamide

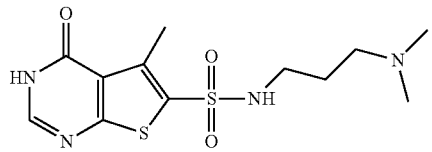 [SMILES: Cc1c(S(=O)(=O)NCCCN(C)C)sc2nc[nH]c(=O)c12]

General Scheme 7

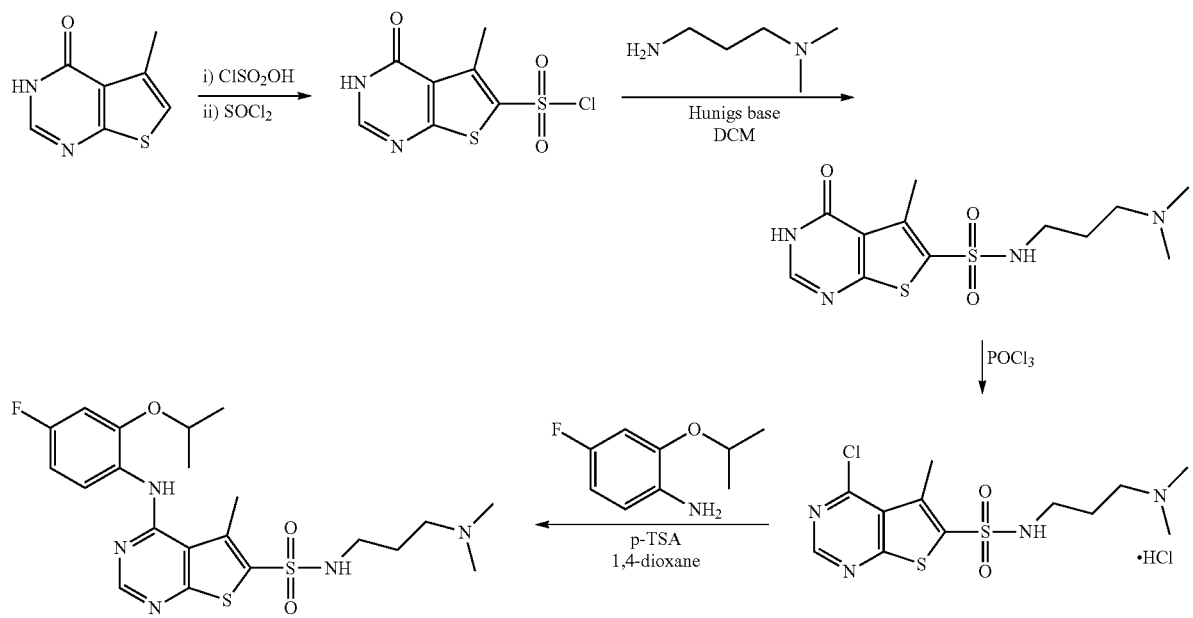

To a stirred suspension of 5-methyl-4-oxo-3,4-dihydrothieno[2,3-d]pyrimidine-6-sulfonyl chloride (1.0 g, 12 mmol) in DCM (10 mL) at 0° C. was added Hünig's base (0.79 mL, 4.5 mmol) followed by N1,N1-dimethylpropane-1,3-diamine (0.52 mL, 4.2 mmol) and the solution stirred at ambient temperature for 2 hours. The suspension was adjusted to pH 8 with 2N hydrochloric acid, the precipitate collected by filtration, washed with water, diethyl ether and dried under vacuum to give the product as off-white solid (1.12 g, 89%).

$^1$H NMR (400 MHz; $d_6$-DMSO; 25° C.): δ 12.50 (bs, 1H), 8.32 (bs, 1H), 8.25 (s, 1H), 3.07-2.95 (m, 4H), 2.76 (s, 3H), 2.71 (s, 6H), 1.92-1.85 (m, 2H).

Preparation of 4-chloro-N-(3-(dimethylamino)propyl)-5-methylthieno[2,3-d]pyrimidine-6-sulfonamide hydrochloride salt

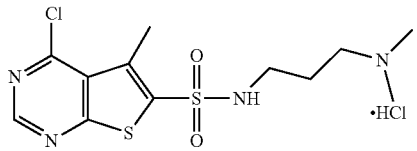 [SMILES: Cc1c(S(=O)(=O)NCCCN(C)C)sc2ncnc(Cl)c12 ; Cl]

To N-(3-(dimethylamino)propyl)-5-methyl-4-oxo-3,4-dihydrothieno[2,3-d]pyrimidine-6-sulfonamide (0.6 g, 1.8 mmol) was added phosphorus oxychloride (5.0 mL, 36 mmol) and the suspension heated at reflux for 1.5 hours. The reaction was cooled to ambient temperature and the excess phosphorus oxychloride removed under vacuum. The residue was co-evaporated several times with chloroform. Drying under vacuum gave a hydroscopic cream solid that was used without further purification (0.65 g, 92%).

$^1$H NMR (400 MHz; $d_6$-DMSO; 25° C.): δ 9.07 (s, 1H), 8.70 (t, 1H), 3.15-3.05 (m, 4H), 2.90 (s, 3H), 2.76 (s, 6H), 1.93-1.87 (m, 2H).

Example 54

N-(3-(Dimethylamino)propyl)-4-(4-fluoro-2-iso-propoxyphenylamino)-5-methylthieno[2,3-d]pyrimidine-6-sulfonamide

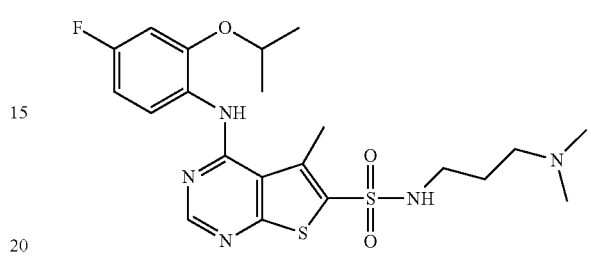

4-Fluoro-2-iso-propoxyaniline (0.049 g, 0.28 mmol) and 4-chloro-N-(3-(dimethylamino)propyl)-5-methylthieno[2,3-d]pyrimidine-6-sulfonamide hydrochloride salt (0.1 g, 0.28 mmol) were heated at 70° C. in anhydrous 1,4-dioxane (1.5 mL) for 4 hours. The solution was cooled to ambient temperature and diluted with water (2.0 mL) and adjusted to pH 9 (4:1 water/ammonium hydroxide solution). The precipitate was collected, washed with water and diethyl ether to yield the title compound as beige solid (0.039 g, 28%).

$^1$H NMR (400 MHz; $d_6$-DMSO; 25° C.): δ 8.60 (s, 1H), 8.55-8.50 (m, 1H), 8.49 (s, 1H), 8.30 (bs, 1H), 7.13 (dd, 1H), 6.87 (dt, 1H), 4.85-4.80 (m, 1H), 3.00 (s, 3H), 2.99-2.93 (m, 2H), 2.25 (t, 2H), 2.10 (s, 6H), 1.59-1.55 (m, 2H), 1.35 (d, 6H). MS (ESI$^+$): 482 (M+H). HPLC (10 cm_ESI_Formic): Rt 2.41 min (HPLC purity 98%).

The following examples have been prepared according to the aforementioned synthetic procedures:

| Example | Structure | Mass | HPLC method | retention time [min] |
|---|---|---|---|---|
| 55 | 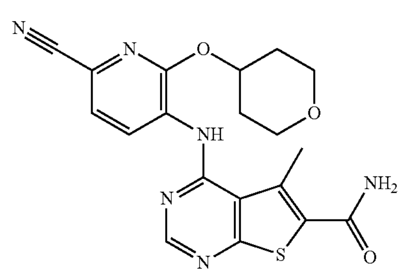 [SMILES: Cc1c(C(N)=O)sc2ncnc(Nc3ccc(C#N)nc3OC3CCOCC3)c12] | 487 | 25cm_Bicarb_Xterra25_HPLC | 15.0 |
| 56 | 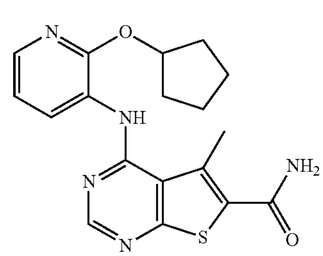 [SMILES: Cc1c(C(N)=O)sc2ncnc(Nc3cccnc3OC3CCCC3)c12] | 482 | 10cm_esci_BICARB | 2.6 |

| Example | Structure | Mass | HPLC method | retention time [min] |
|---|---|---|---|---|
| 57 | 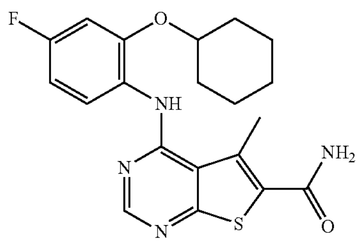 [SMILES: Cc1c(C(N)=O)sc2ncnc(Nc3ccc(F)cc3OC3CCCCC3)c12] | 444 | 10cm_ESI_formic | 2.7 |
| 58 | 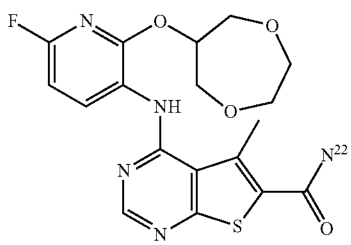 | 509 | 10cm_ESI_formic | 3.2 |
| 59 | 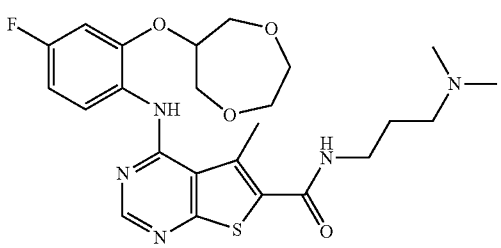 [SMILES: Cc1c(C(=O)NCCCN(C)C)sc2ncnc(Nc3ccc(F)cc3OC3COCCOC3)c12] | 488 | 10cm_ESI_formic | 2.8 |
| 60 | 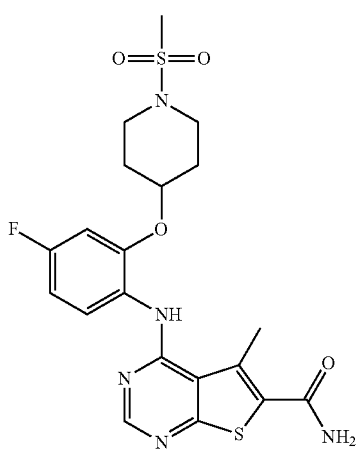 [SMILES: Cc1c(C(N)=O)sc2ncnc(Nc3ccc(F)cc3OC3CCN(S(C)(=O)=O)CC3)c12] | 493 | 10cm_esci_BICARB | 2.8 |

-continued

| Example | Structure | Mass | HPLC method | retention time [min] |
|---|---|---|---|---|
| 61 | 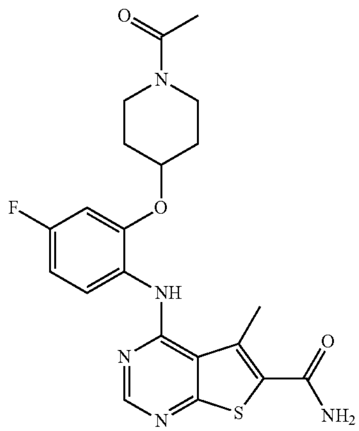 [SMILES: CC(=O)N1CCC(Oc2cc(F)ccc2Nc2ncnc3sc(C(N)=O)c(C)c23)CC1] | 445 | 15cm_Formic_Slow_Sunfire_HPLC | 10.4 |
| 62 | 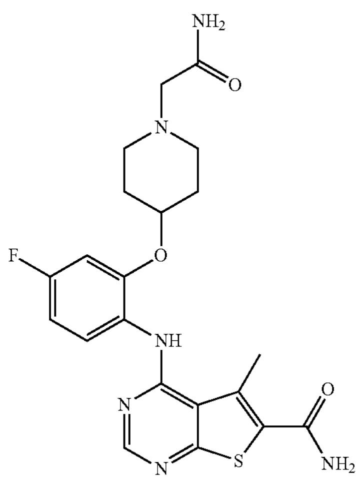 [SMILES: Cc1c(C(N)=O)sc2ncnc(Nc3ccc(F)cc3OC3CCN(CC(N)=O)CC3)c12] | 419 | 10cm_esci_BICARB | 2.7 |
| 63 | 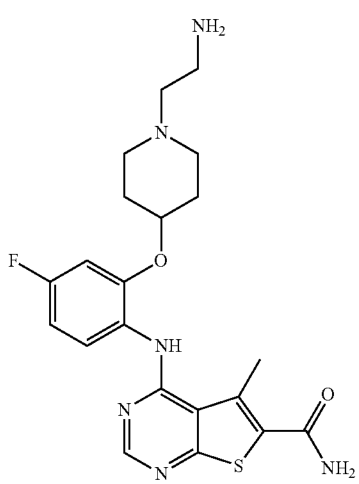 [SMILES: Cc1c(C(N)=O)sc2ncnc(Nc3ccc(F)cc3OC3CCN(CCN)CC3)c12] | 370 | 10cm_ESI_formic | 3.6 |

-continued

| Example | Structure | Mass | HPLC method | retention time [min] |
|---|---|---|---|---|
| 64 | 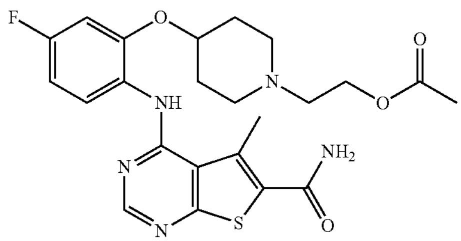 [SMILES: CC(=O)OCCN1CCC(Oc2cc(F)ccc2Nc2ncnc3sc(C(N)=O)c(C)c23)CC1] | 401 | 15cm_esci_Synergy_Formic | 18.3 |
| 65 | 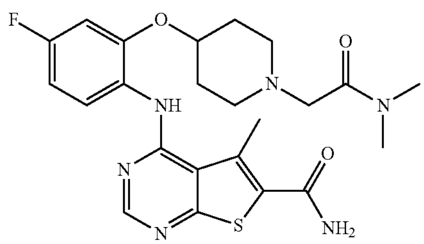 [SMILES: Cc1c(C(N)=O)sc2ncnc(Nc3ccc(F)cc3OC3CCN(CC(=O)N(C)C)CC3)c12] | 514 | 15cm_Formic_Slow_Sunfire_HPLC | 11.0 |
| 66 | 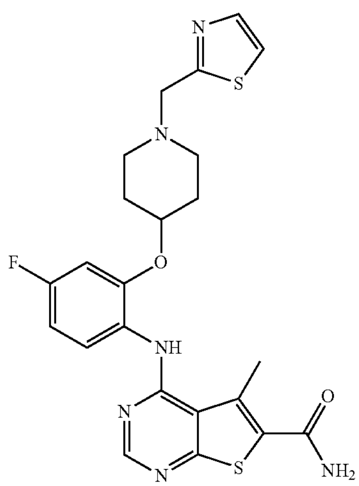 [SMILES: Cc1c(C(N)=O)sc2ncnc(Nc3ccc(F)cc3OC3CCN(Cc4nccs4)CC3)c12] | 504 | 10cm_ESI_formic | 2.8 |
| 67 | 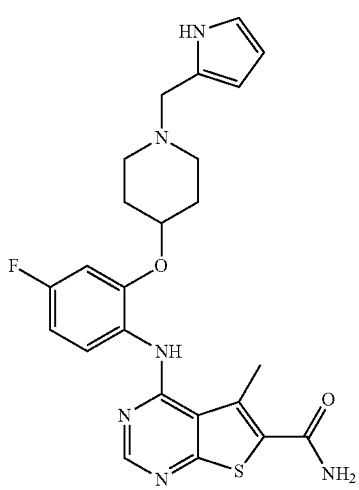 [SMILES: Cc1c(C(N)=O)sc2ncnc(Nc3ccc(F)cc3OC3CCN(Cc4ccc[nH]4)CC3)c12] | 459 | 10cm_esci_BICARB | 2.5 |

-continued

| Example | Structure | Mass | HPLC method | retention time [min] |
|---|---|---|---|---|
| 68 | 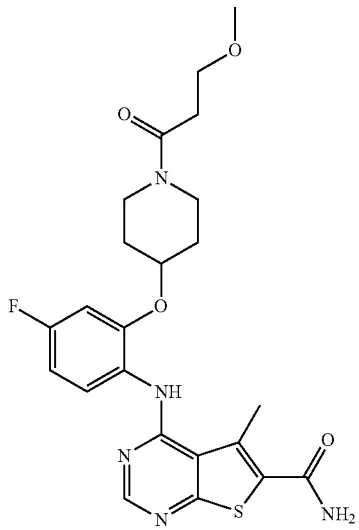 [SMILES: COCCC(=O)N1CCC(Oc2cc(F)ccc2Nc2ncnc3sc(C(N)=O)c(C)c23)CC1] | 481 | 25cm_Bicarb_Xterra25_HPLC | 17.2 |
| 69 | 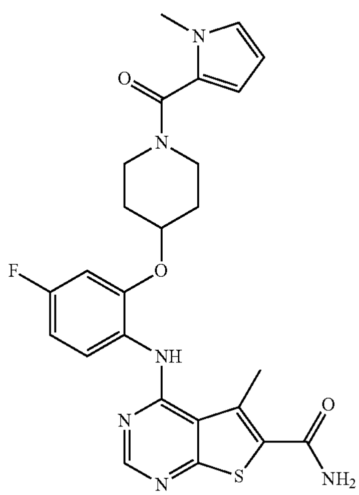 [SMILES: Cc1c(C(N)=O)sc2ncnc(Nc3ccc(F)cc3OC3CCN(C(=O)c4cccn4C)CC3)c12] | 499 | 10cm_esci_BICARB | 2.9 |
| 70 | 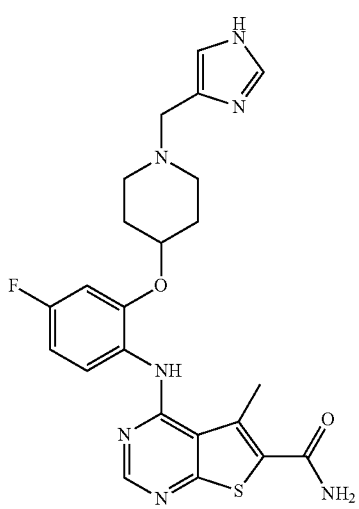 [SMILES: Cc1c(C(N)=O)sc2ncnc(Nc3ccc(F)cc3OC3CCN(Cc4c[nH]cn4)CC3)c12] | 529 | 15cm_Formic_Slow_Sunfire_HPLC | 11.4 |

-continued

| Example | Structure | Mass | HPLC method | retention time [min] |
|---|---|---|---|---|
| 71 | 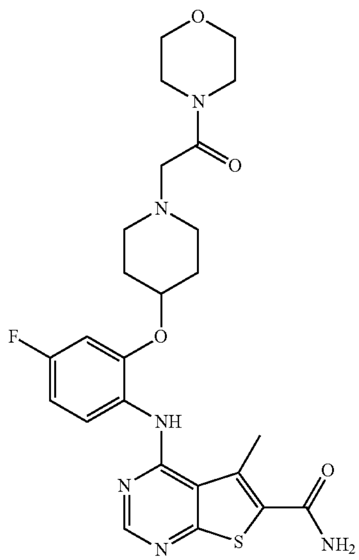 [SMILES: Cc1c(C(N)=O)sc2ncnc(Nc3ccc(F)cc3OC3CCN(CC(=O)N4CCOCC4)CC3)c12] | 480 | 10cm_ESI_formic | 2.9 |
| 72 | 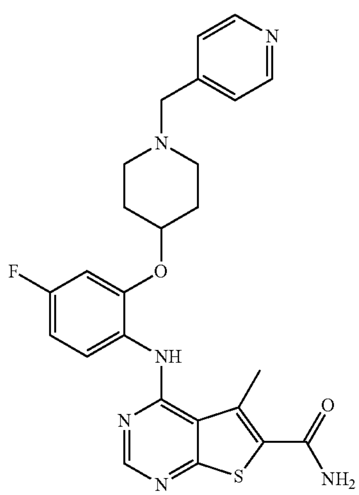 [SMILES: Cc1c(C(N)=O)sc2ncnc(Nc3ccc(F)cc3OC3CCN(Cc4ccncc4)CC3)c12] | 493 | 15cm_Formic_Slow_Sunfire_HPLC | 11.8 |
| 73 | 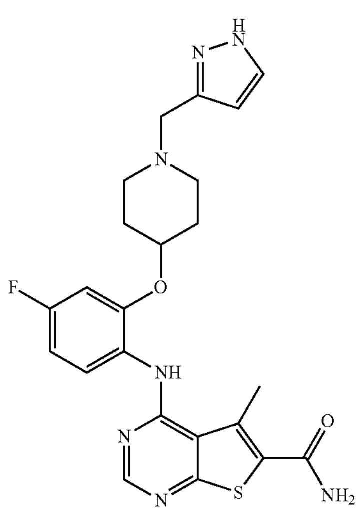 [SMILES: Cc1c(C(N)=O)sc2ncnc(Nc3ccc(F)cc3OC3CCN(Cc4cc[nH]n4)CC3)c12] | 488 | 15cm_Formic_Slow_Sunfire_HPLC | 11.4 |

| Example | Structure | Mass | HPLC method | retention time [min] |
|---|---|---|---|---|
| 74 | 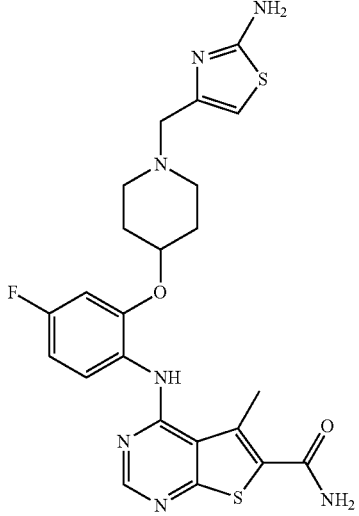 [SMILES: Cc1c(C(N)=O)sc2ncnc(Nc3ccc(F)cc3OC3CCN(Cc4csc(N)n4)CC3)c12] | 482 | 15cm_Formic_Slow_Sunfire_HPLC | 10.5 |
| 75 | 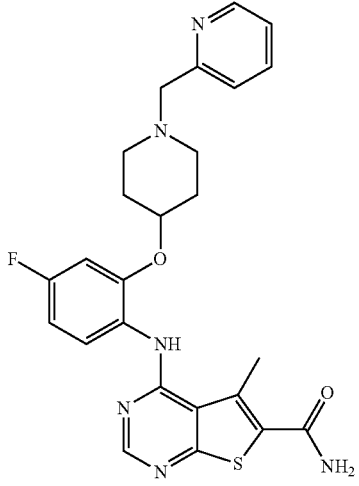 [SMILES: Cc1c(C(N)=O)sc2ncnc(Nc3ccc(F)cc3OC3CCN(Cc4ccccn4)CC3)c12] | 411 | 10cm_ESI_formic | 3.1 |

Example 2

Kinase Fluorescence Polarization Assays

Assay Principle:

Inhibitory potency of compounds against Mnk1, Mnk2a and other kinases was assessed with assays based on a format known to those skilled in the art as the indirect (competitive) fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay

Example 2a

Mnk1 and Mnk2a In Vitro Kinase Assay

As a source of enzyme, human Mnk1 and human Mnk2a were expressed as GST fusion proteins in *E. coli*, purified to >80% homogeneity by glutathione affinity chromatography and activated in vitro with pre-activated ERK2. In brief, the open reading frames of human Mnk1 and Mnk2a were amplified from cDNA using the forward/reverse primer pairs SEQ ID NO: 1
5'TTTA<u>GGATCC</u>GTATCTTCTCAAAAGTTGG/

SEQ ID NO: 2
5' CTGG<u>GTCGAC</u>TCAGAGTGCTGTGGGCGG
and

```
                                              SEQ ID NO: 3
5' ACAGGGATCCGTGCAGAAGAAACCAGCC/

SEQ ID NO: 4
5' GATGGTCGACTCAGGCGTGGTCTCCCACC
```

(utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione S-transferase (GST) tag, referred to as GST-Mnk1 or GST-Mnk2a. The following expression and purification procedure was identical for GST-Mnk1 and GST-Mnk2a, referring in general to GST-Mnk, when not distinguishing between the two isoforms. Expression of GST-Mnk was in E. coli BL21 (Merck Biosciences, Germany, cat. no. 69449). Cells were grown in LB-Bouillon (Merck, Germany, cat. no. 1.10285) supplemented with 100 µg/ml ampicillin (Sigma, Germany, cat. no. A9518) at 37° C. When the culture had reached a density corresponding to an $A_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiotreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycol-bis(2-aminoethylether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. $SO_{389}$) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 µM of either purified GST-Mnk1 or GST-Mnk2a by incubation with 150 nM pre-activated NHis-ERK2 (see ERK2 assay for preparation) and 50 µM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12mer peptide with the sequence
SEQ ID NO: 5 TATKSGSTTKNR,
derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR (SEQ ID NO: 6), containing an amidated carboxyterminus and conjugated at the amino-terminus with the oxazine derived fluorophore depicted below was synthesized and used as ligand.

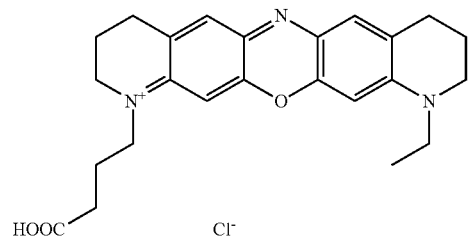 [SMILES: CCN1CCCc2cc3c(cc21)Oc1cc2c(cc1=N3)CCC[N+]=2CCCC(=O)O ; [Cl-]]

ANTIBODY: SPF New Zealand White Rabbits have been immunized according to standard protocols with the peptide NH2-CTATKSG-pS-TTKNR-CONH2 (SEQ ID NO: 7), coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 µM substrate peptide, 20 µM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 µM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

The activity of Mnk proteins can be assayed also by other in vitro kinase assay formats. For example, suitable kinase assays have been described in the literature in Knauf et al., Mol Cell Biol. 2001 August; 21(16):5500-11 or in Scheper et al., Mol Cell Biol. 2001 February; 21(3):743-54. In general, Mnk kinase assays can be performed such that a Mnk substrate such as a protein or a peptide, which may or may not include modifications as further described below, or others are phosphorylated by Mnk proteins having enzymatic activity in vitro. The activity of a candidate agent can then be determined via its ability to decrease the enzymatic activity of the Mnk protein. The kinase activity may be detected by change of the chemical, physical or immunological properties of the substrate due to phosphorylation.

In one example, the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues (SEQ ID NO: 8), an amino acid sequence or hapten to function as an epitope tag, a fluorochrome, an enzyme or enzyme fragment. The kinase substrate may be linked to these or other features with a molecular spacer arm to avoid steric hindrance.

In another example the kinase substrate may be labelled with a fluorophore. The binding of the reagent to the labelled substrate in solution may be followed by the technique of fluorescence polarization as it is described in the literature. In a variation of this example, a fluorescent tracer molecule may compete with the substrate for the analyte to detect kinase activity by a technique which is know to those skilled in the art as indirect fluorescence polarization.

In yet another example, radioactive gamma-ATP is used in the kinase reaction, and the effect of the test agent on the incorporation of radioactive phosphate in the test substrate is determined relative to control conditions.

It has been shown that the particular preferred compounds of the invention exhibit $IC_{50}$ values below 1 micromolar in in vitro biological screening assays as described in example 2a for inhibition of Mnk 1 and/or Mnk 2 kinase activity. The following table contains the test results for exemplary compounds.

| Example | $IC_{50}$ Mnk1 [µM] | $IC_{50}$ Mnk2a [µM] |
| --- | --- | --- |
| 2 | 0.12 | 0.028 |
| 6 | 0.18 | 0.035 |
| 9 | 0.1 | 0.027 |
| 10 | 0.21 | 0.034 |
| 19 | 0.59 | 0.06 |
| 34 | 0.68 | 0.56 |
| 41 | 0.21 | 0.11 |
| 48 | 0.46 | 0.092 |
| 53 | 0.035 | 0.006 |
| 71 | 0.4 | 0.16 |

The invention claimed is:
1. A compound of the formula (I)

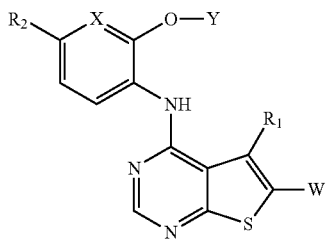

wherein
X is CH or N;
R$_2$ is selected from H, CN, CF$_3$, CON(R$_4$)$_2$; O—C$_{1-8}$ alkyl optionally substituted by R$_3$; monocyclic saturated or unsaturated three to ten membered heterocyclyl containing 1 to 4 heteroatoms selected from N, S and O; mono- or bicyclic five to ten membered heteroaryl containing 1 to 4 heteroatoms selected from N, S and O; and C$_{1-8}$ alkyl optionally substituted by R$_6$; and when X is CH, R$_2$ may also be F, Cl, SO$_2$NH$_2$;
Y is selected from straight chain or branched C$_{1-8}$ alkyl, optionally substituted by one or more of R$_3$; C$_{3-8}$ cycloalkyl, optionally substituted by one or more of R$_9$; and heterocyclyl systems selected from any one of the formulae:

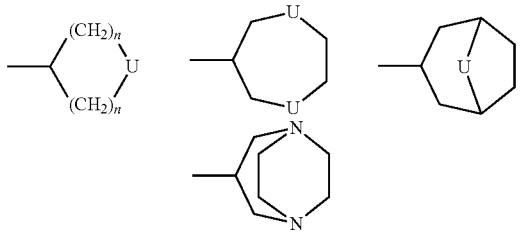

optionally substituted by one or more of R$_9$,
wherein n is independently 1 to 3 and U is independently O or NR$_5$;
R$_1$ is selected from H; Cl; and C$_{1-8}$ alkyl, optionally substituted by N(R$_4$)$_2$ or F;
R$_3$ is selected from OH, OR$_4$ and N(R$_4$)$_2$ from the second carbon atom of the alkyl chain to which R$_3$ is attached onwards; F; CO$_2$H; CON(R$_4$)$_2$; SO$_2$N(R$_4$)$_2$; monocyclic saturated or unsaturated three to ten membered heterocyclyl containing 1 to 4 heteroatoms selected from N, S and O, wherein the nitrogen atom may be substituted by H or C$_{1-3}$ alkyl; and mono- or bicyclic five to ten membered heteroaryl containing 1 to 4 heteroatoms selected from N, S and O;
R$_4$ is selected from H and C$_{1-8}$ alkyl;
R$_5$ is selected from H; C$_{1-8}$ alkyl; C$_{2-8}$ alkenyl; C$_{3-10}$ cycloalkyl; monocyclic saturated or unsaturated three to ten membered heterocyclyl containing 1 to 4 heteroatoms selected from N, S and O; mono- or bicyclic five to ten membered heteroaryl containing 1 to 4 heteroatoms selected from N, S and O; COR$_6$; CO$_2$R$_4$; CONH(CH$_2$)$_m$R$_6$; (CH$_2$)$_m$R$_6$; CO(CH$_2$)$_m$R$_6$; (CH$_2$)$_m$C(O)R$_6$; SO$_2$R$_4$; and SO$_2$(CH$_2$)$_m$R$_6$; wherein m is 1-4;
R$_6$ is selected from H; OH; OR$_4$; OC(O)R$_4$; N(R$_4$)$_2$; F; CO$_2$H; CON(R$_4$)$_2$; SO$_2$N(R$_4$)$_2$; monocyclic saturated or unsaturated three to ten membered heterocyclyl containing 1 to 4 at least one heteroatoms selected from N, S and O; mono- or bicyclic five to ten membered heteroaryl containing 1 to 4 heteroatoms selected from N, S and O, which is optionally substituted by C$_{1-3}$ alkyl or N(R$_4$)$_2$;
W is selected from F; Cl; Br; I; CN; —(CH$_2$)$_{1-2}$NR$_7$R$_8$; —C(S)NH$_2$; —CONR$_7$R$_8$; —C(=NR$_7$)NR$_7$R$_8$; —CO$_2$R$_7$; and —SO$_2$NR$_7$R$_8$;
or W together with R$_1$ can form a five to seven membered monocyclic saturated or unsaturated heterocyclic ring containing 1 to 4 heteroatoms selected from N, S and O, wherein the nitrogen atom may be substituted by H, —C(O)—O—C$_{1-4}$ alkyl, —CO—(CH$_2$)$_{1-2}$—NH$_2$, —CO—(CH$_2$)$_{1-2}$—NH(C$_{1-3}$ alkyl) or —CO—(CH$_2$)$_{1-2}$—N(C$_{1-3}$ alkyl)$_2$;
R$_7$ is selected from H and C$_{1-8}$ alkyl;
R$_8$ is selected from H; C$_{1-8}$ alkyl optionally substituted by R$_3$; monocyclic saturated or unsaturated three to ten membered heterocyclyl containing 1 to 4 heteroatoms selected from N, S and O; and mono- or bicyclic five to ten membered heteroaryl containing 1 to 4 heteroatoms selected from N, S and O;
R$_9$ is selected from OH, OR$_4$, N(R$_4$)$_2$, N(R$_4$)COR$_4$, NR$_4$SO$_2$R$_4$ and N(R$_4$)—(CH$_2$)$_m$—R$_4$ on any carbon atom other than one attached to O or N; F; CO$_2$H; CON(R$_4$)$_2$; SO$_2$N(R$_4$)$_2$; SO$_2$R$_4$; (CH$_2$)$_m$OR$_4$; (CH$_2$)$_m$N(R$_4$)$_2$; monocyclic saturated or unsaturated three to ten membered heterocyclyl containing 1 to 4 heteroatoms selected from N, S and O; and mono- or bicyclic five to ten membered heteroaryl containing 1 to 4 heteroatoms selected from N, S and O;
with the proviso that the compound ethyl 4-(2-methoxyphenylamino)-5-methylthieno[2,3-d]pyrimidine-6-carboxylate is excluded;
or a tautomer, or a pharmaceutically acceptable salt thereof.

2. A compound of formula (I) according to claim 1, wherein
X is CH or N;
R$_2$ is H, CN, CF$_3$, CON(R$_4$)$_2$, O—C$_{1-4}$ alkyl optionally substituted by C$_{1-3}$ alkoxy; or furanyl; and when X is CH, R$_2$ may also be F, Cl;
Y is straight chain or branched C$_{1-4}$ alkyl, optionally substituted by R$_3$; C$_{3-8}$ cycloalkyl, optionally substituted by one or two R$_9$; or a heterocyclyl system selected from any one of the formulae:

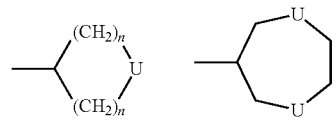

optionally substituted by one or more of R$_9$,
wherein n is independently 1 to 3 and U is independently O or NR$_5$;
R$_1$ is H; or C$_{1-3}$ alkyl;
R$_3$ is OH, OR$_4$ and N(R$_4$)$_2$ from the second carbon atom of the alkyl chain to which R$_3$ is attached onwards; or monocyclic saturated or unsaturated five to seven membered heterocyclyl containing one or two heteroatoms selected from N, S and O, wherein the nitrogen atom may be substituted by H or C$_{1-3}$ alkyl;
R$_4$ is H or C$_{1-4}$ alkyl;

$R_5$ is H; $C_{1-4}$ alkyl; $COR_6$; $CO_2R_4$; $SO_2R_4$; $C(O)-(CH_2)_m-R_6$; $(CH_2)_mC(O)R_6$; or $(CH_2)_mR_6$;

wherein m is 1-4;

$R_6$ is H; OH; $OR_4$; $OC(O)R_4$; $N(R_4)_2$; F; $CO_2H$; $CON(R_4)_2$; $SO_2N(R_4)_2$; monocyclic saturated or unsaturated three to ten membered heterocyclyl containing 1 to 4 heteroatoms selected from N, S and O; or mono- or bicyclic ve to ten membered heteroaryl containing 1 to 4 heteroatoms selected from N, S and O, which is optionally substituted by $C_{1-3}$ alkyl or $N(R_4)_2$;

W is F; Cl; Br; CN; $-C(S)NH_2$; $-CONR_7R_8$; $-C(=NR_7)NR_7R_8$; $-CO_2R_7$; or $-SO_2NR_7R_8$;

or W together with $R_1$ can form a five to seven membered monocyclic saturated or unsaturated heterocyclic ring containing 1 to 4 at least one heteroatom selected from N, S and O, wherein the nitrogen atom may be substituted by H, $-C(O)-O-C_{1-4}$ alkyl, $-CO-(CH_2)_{1-2}-NH_2$, $-CO-(CH_2)_{1-2}-NH(C_{1-3}$ alkyl) or $-CO-(CH_2)_{1-2}-N(C_{1-3}$ alkyl)$_2$;

$R_7$ is H or $C_{1-3}$ alkyl;

$R_8$ is H; $C_{1-4}$ alkyl optionally substituted by $R_3$; monocyclic saturated or unsaturated three to ten membered heterocyclyl containing 1 to 4 heteroatoms selected from N, S and O; or mono- or bicyclic five to ten membered heteroaryl containing 1 to 4 heteroatoms selected from N, S and O;

$R_9$ is OH, $OR_4$, $N(R_4)_2$, $N(R_4)COR_4$, $NR_4SO_2R_4$ or $N(R_4)-(CH_2)_m-R_4$ on any carbon atom other than one attached to O or N; $SO_2R_4$; $-(CH_2)_m-OR_4$; or monocyclic saturated or unsaturated heterocyclic ring containing 1 to 4 comprising at least one heteroatom selected from N, S and O;

with the proviso that the compound ethyl 4-(2-methoxyphenylamino)-5-methylthieno[2,3-d]pyrimidine-6-carboxylate is excluded;

or a tautomer, or a pharmaceutically acceptable salt thereof.

3. A compound of the formula (I) according to claim 2, wherein

X is CH or N;

$R_2$ is H, CN, $CF_3$, or $CONH_2$; and when X is CH, $R_2$ may also be F, Cl;

Y is $C_{3-8}$ cycloalkyl, optionally substituted by $N(R_4)$ $COR_4$, $SO_2R_4$, $-(CH_2)_m-OR_4$ or morpholino; or a heterocyclyl system selected from any one of the formulae:

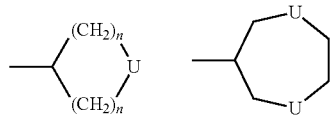

wherein n is independently 1 to 3 and U is independently O or $NR_5$;

$R_1$ is H; or $C_{1-3}$ alkyl;

$R_3$ is OH, $OR_4$, $N(R_4)_2$; or a heterocycle selected from morpholinyl or pyrrolidinyl, wherein the nitrogen atom or the heterocycle may be substituted by $C_{1-3}$ alkyl;

$R_4$H or $C_{1-4}$ alkyl;

$R_5$ is H; $COR_6$; $CO_2R_4$; $SO_2R_4$; $-C(O)-(CH_2)_m-R_6$; $(CH_2)_mC(O)R_6$; or $(CH_2)_mR_6$; wherein m is 1 to 4;

$R_6$ is H; OH; $OR_4$; $OC(O)R_4$; $N(R_4)_2$; F; $CO_2H$; $CON(R_4)_2$; $SO_2N(R_4)_2$; morpholinyl; or a heteroaryl group selected from pyrrolyl, pyrazolyl, imidazolyl, thiazolyl, oxadiazolyl and pyridinyl, each optionally substituted by methyl or $NH_2$;

W is F; Cl; Br; CN; $-C(S)NH_2$; $-CONR_7R_8$; $-C(=NR_7)NR_7R_8$; $-CO_2R_7$; or $-SO_2NR_7R_8$;

$R_7$ is H or $C_{1-3}$ alkyl;

$R_8$ is H; $C_{1-4}$ alkyl; $C_{2-4}$ alkyl substituted terminally by $R_3$; or piperidinyl optionally substituted by $C_{1-3}$ alkyl;

or a tautomer, or a pharmaceutically acceptable salt thereof.

4. A compound of formula (I) according to claim 1 wherein $R_1$ is methyl, with the proviso that the compound ethyl 4-(2-methoxyphenylamino)-5-methylthieno[2,3-d]pyrimidine-6-carboxylate is excluded;

or a tautomer, or a pharmaceutically acceptable salt thereof.

5. A compound of formula (I) according to claim 4, wherein

Y is a heterocyclyl system selected from any one of the formulae:

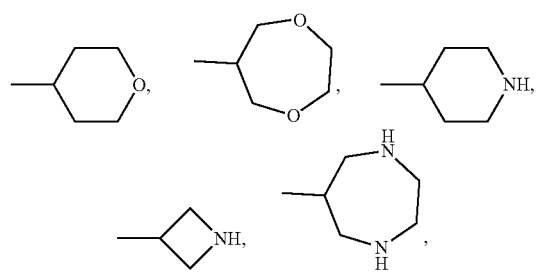

wherein the nitrogen atoms are optionally independently substituted by $C_{1-3}$ alkyl, $-C(O)OC_{1-4}$ alkyl, $-C(O)C_{1-4}$ alkyl, $-C(O)-(CH_2)_q-OC_{1-4}$ alkyl, $-C(O)-(CH_2)_q-N(CH_3)_2$, $-SO_2C_{1-3}$ alkyl, $-(CH_2)_p-NH_2$, $-(CH_2)_p-OH$, $-(CH_2)_p-OC(O)C_{1-3}$ alkyl, $-(CH_2)_qC(O)NH_2$, $-(CH_2)_qC(O)N(CH_3)_2$; $-CH_2$-heteroaryl, which is optionally substituted in the heteroaryl moiety by $NH_2$ and wherein the heteroaryl moiety is selected from pyrrolyl, pyrazolyl, imidazolyl, thiazolyl, oxadiazolyl and pyridinyl; $-C(O)$-pyrrolyl, which is optionally substituted by $C_{1-3}$ alkyl; or $-CH_2-C(O)$-morpholino, wherein q is 1 to 3 and p is 2 or 3, or a tautomer, or a pharmaceutically acceptable salt thereof.

6. A compound of formula (I) according to claim 1 wherein

W together with $R_1$ and the thieno moiety of the core structure depicted in formula (I) form a ring selected from the formulae (II)-(VI)

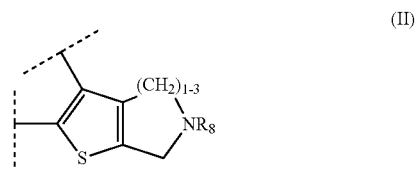

(II)

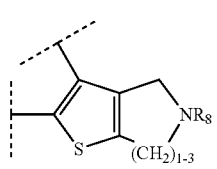
(III)

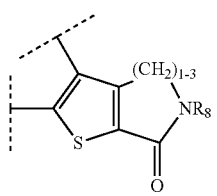
(IV)

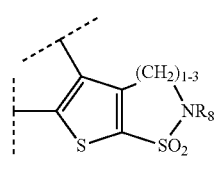
(V)

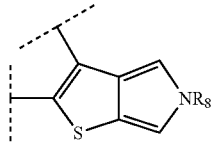
(VI)

wherein R$_8$ is H, —C(O)OC$_{1-4}$ alkyl or —C(O)—CH$_2$—N(CH$_3$)$_2$, or a tautomer, or a pharmaceutically acceptable salt thereof.

7. A compound of formula (I) according to claim 6, wherein
W together with R$_1$ and the thieno moiety of the core structure depicted in formula (I) form a ring of formula (II),
wherein R$_8$ is H, —C(O)OC$_{1-4}$ alkyl or —C(O)—CH$_2$—N(CH$_3$)$_2$, or a tautomer, or a pharmaceutically acceptable salt thereof.

8. A compound of formula (I) according to claim 1 wherein
W is selected from —CONR$_7$R$_8$ or —CO$_2$R$_7$,
wherein R$_7$ is H or methyl and
R$_8$ is C$_{1-4}$ alkyl optionally substituted by OH, —O—C$_{1-3}$ alkyl, —NH$_2$, —NH(C$_{1-3}$ alkyl), —N(C$_{1-3}$ alkyl)$_2$, morpholino, pyrrolidinyl or N-methyl-pyrrolidinyl,
or a tautomer, or a pharmaceutically acceptable salt thereof.

9. A compound of formula (I) according to claim 8, wherein
W is —C(O)NH$_2$ or —C(O)NHR$_8$,
wherein R$_8$ is C$_{1-4}$ alkyl optionally substituted by OH, —O—C$_{1-3}$ alkyl, —NH$_2$, —NH(C$_{1-3}$ alkyl), —N(C$_{1-3}$ alkyl)$_2$, morpholino, pyrrolidinyl or N-methyl-pyrrolidinyl,
or a tautomer, or a pharmaceutically acceptable salt thereof.

10. A compound of formula (I) according to claim 1 wherein
X is CH and
R$_2$ is F, Cl, CN or C(O)NH$_2$,
or a tautomer, or a pharmaceutically acceptable salt thereof.

11. A compound of formula (I) according to claim 1 wherein
X is N and
R$_2$ is H or CN,
or a tautomer, or a pharmaceutically acceptable salt thereof.

12. The compound according to claim 1 selected from a group consisting of:

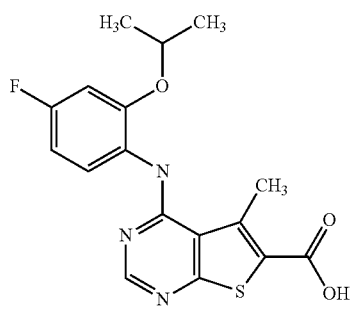

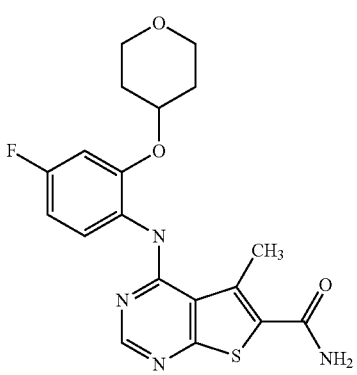

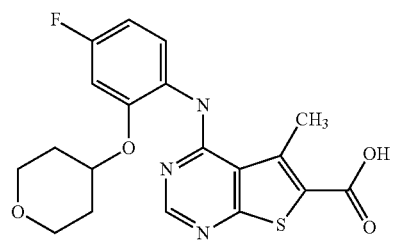

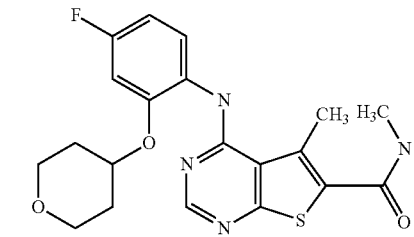

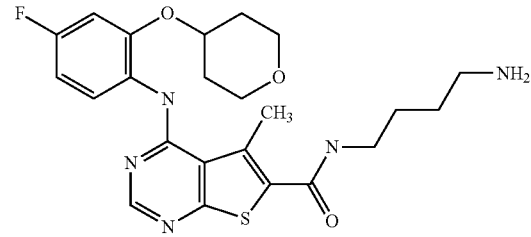

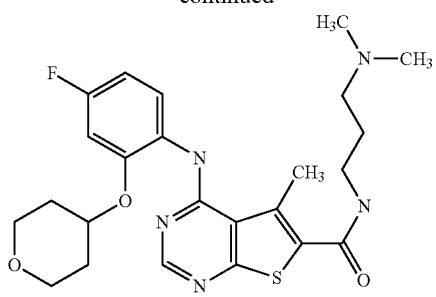
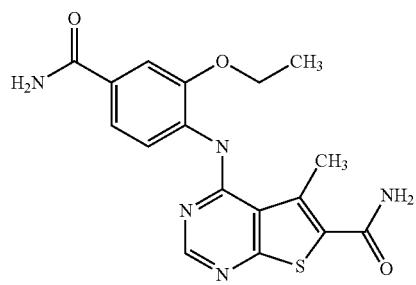
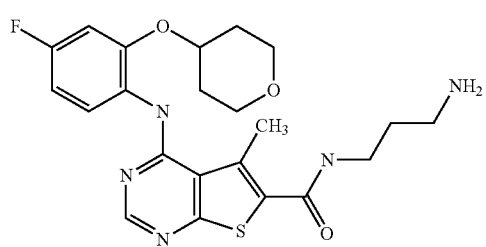
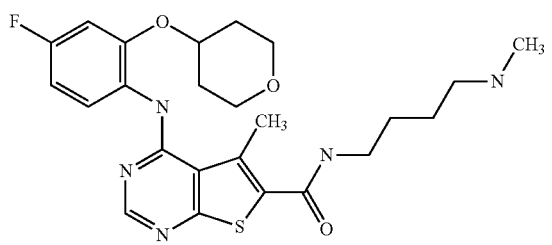
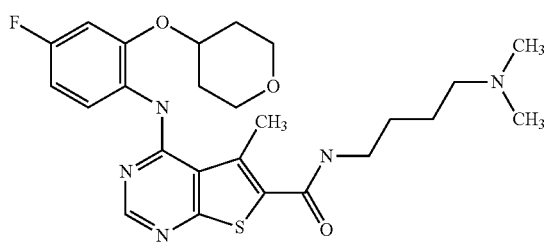
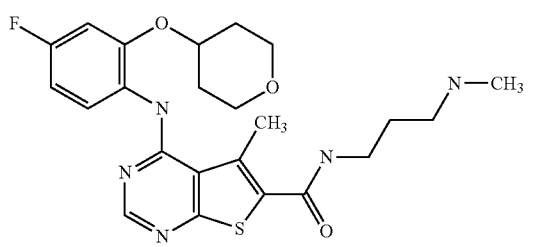
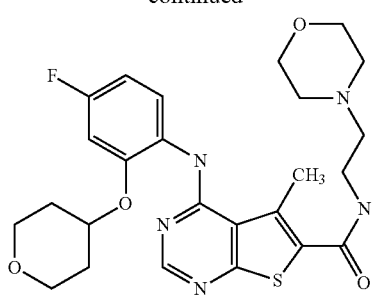
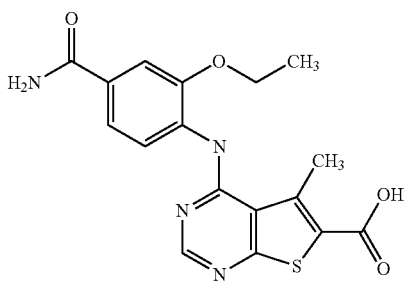
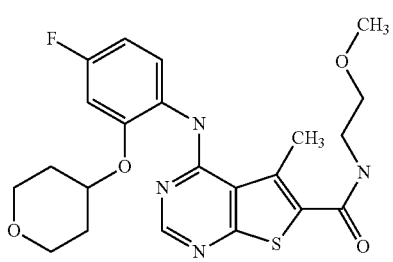
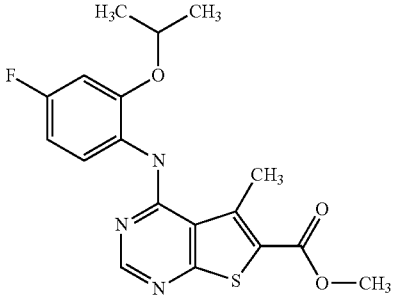
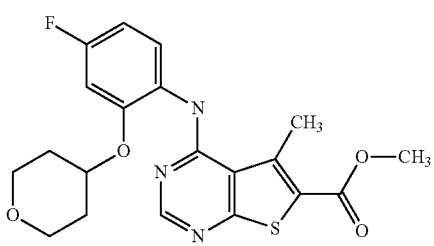
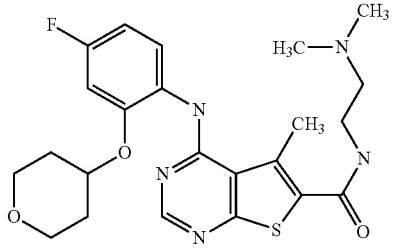

111
-continued
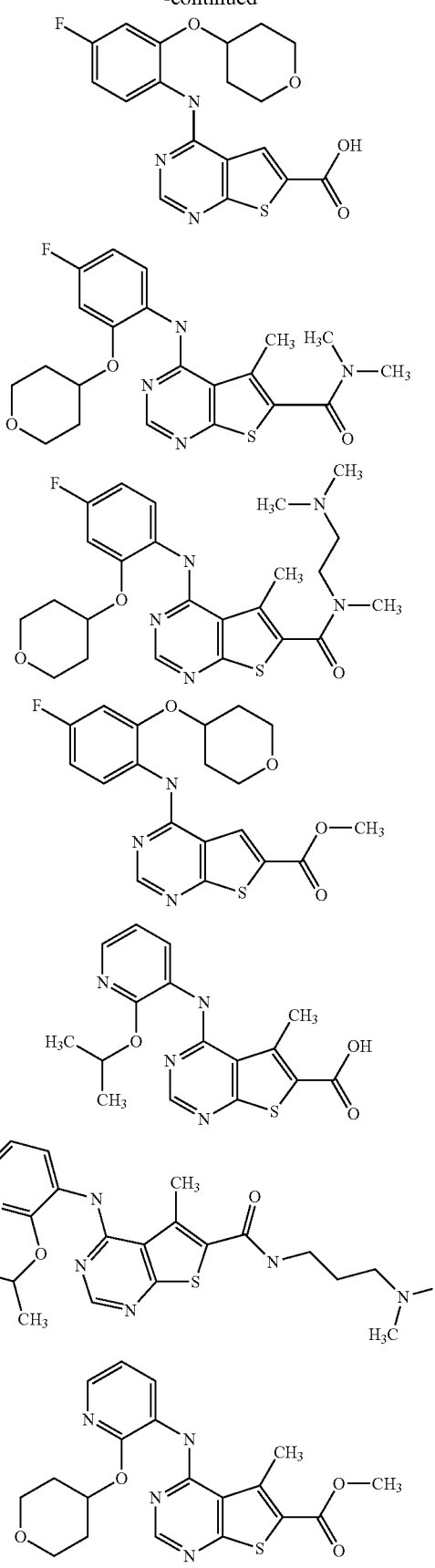
112
-continued
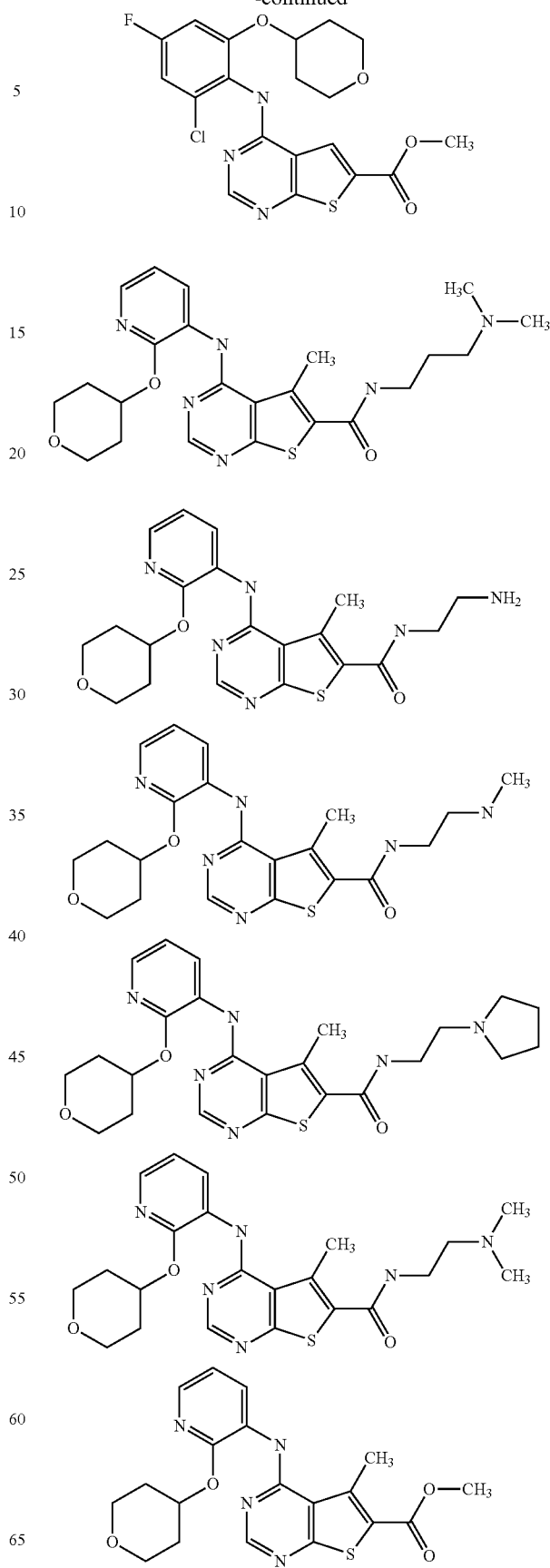

113
-continued
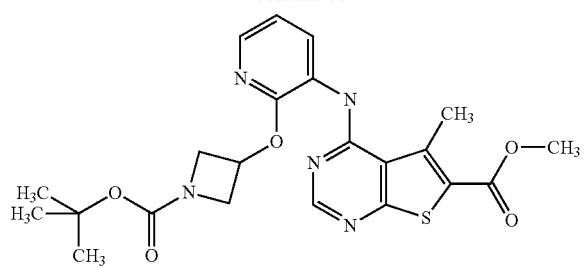
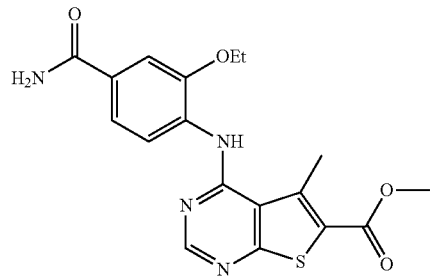
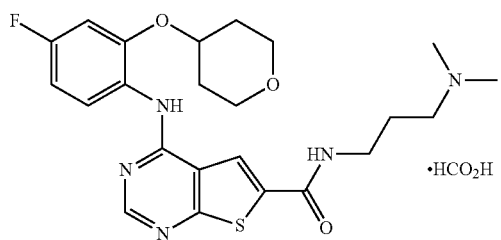
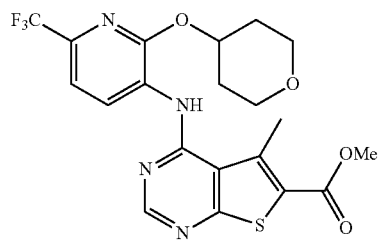
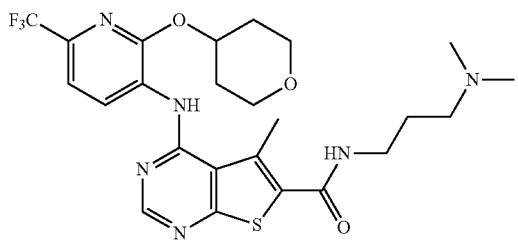
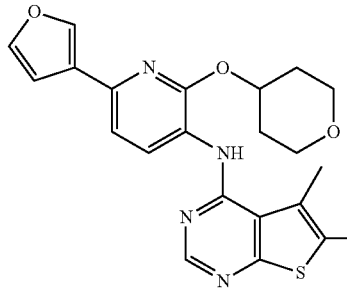
114
-continued
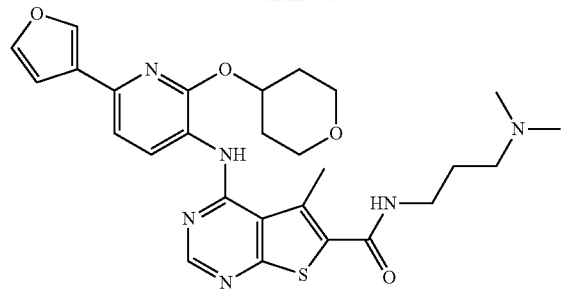
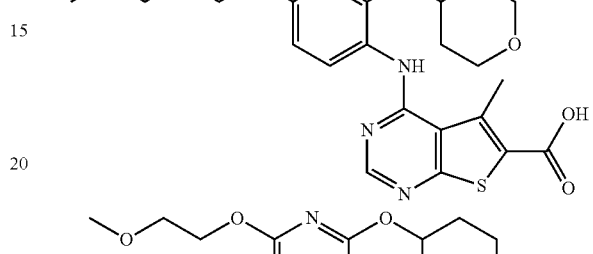
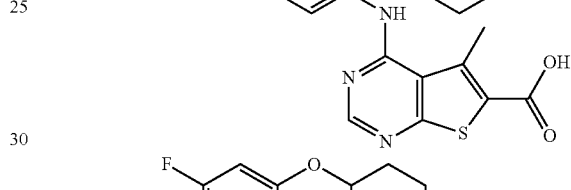
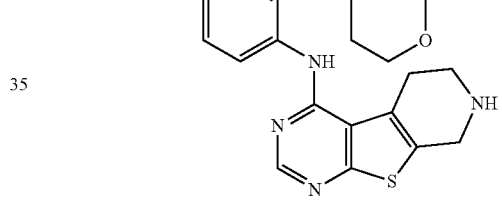
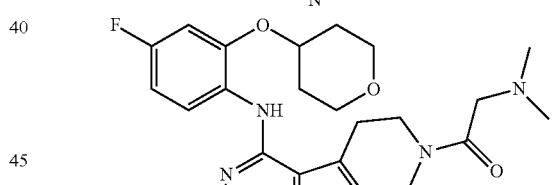
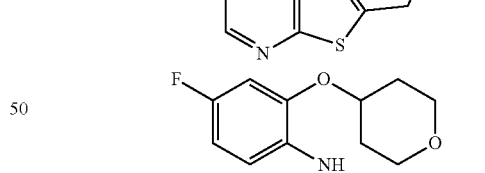
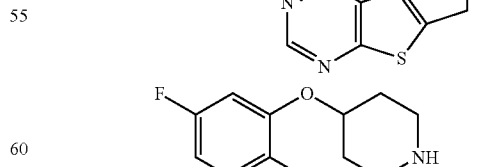
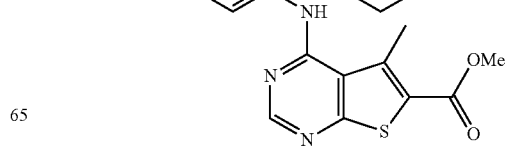

115
-continued
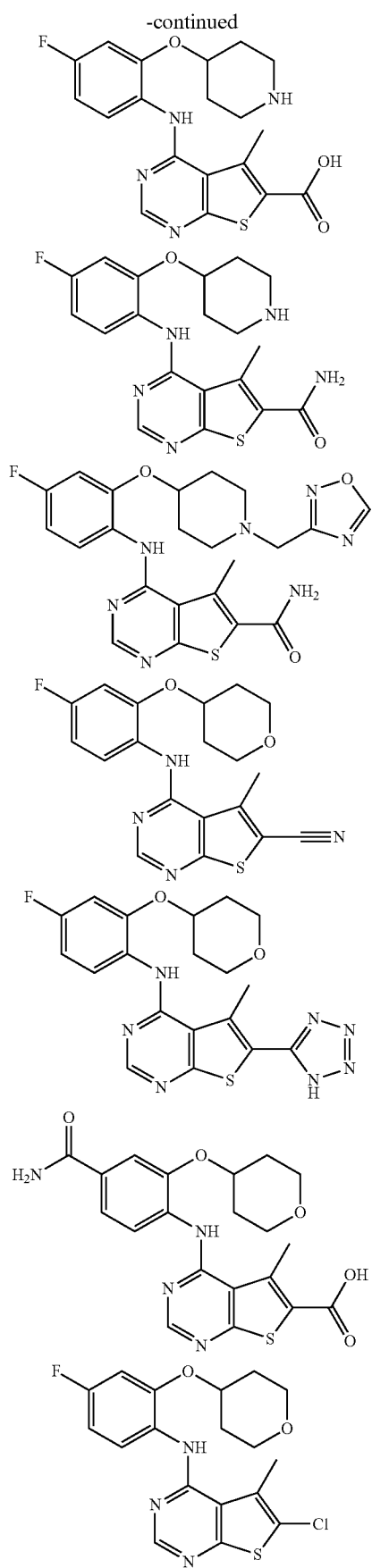
116
-continued
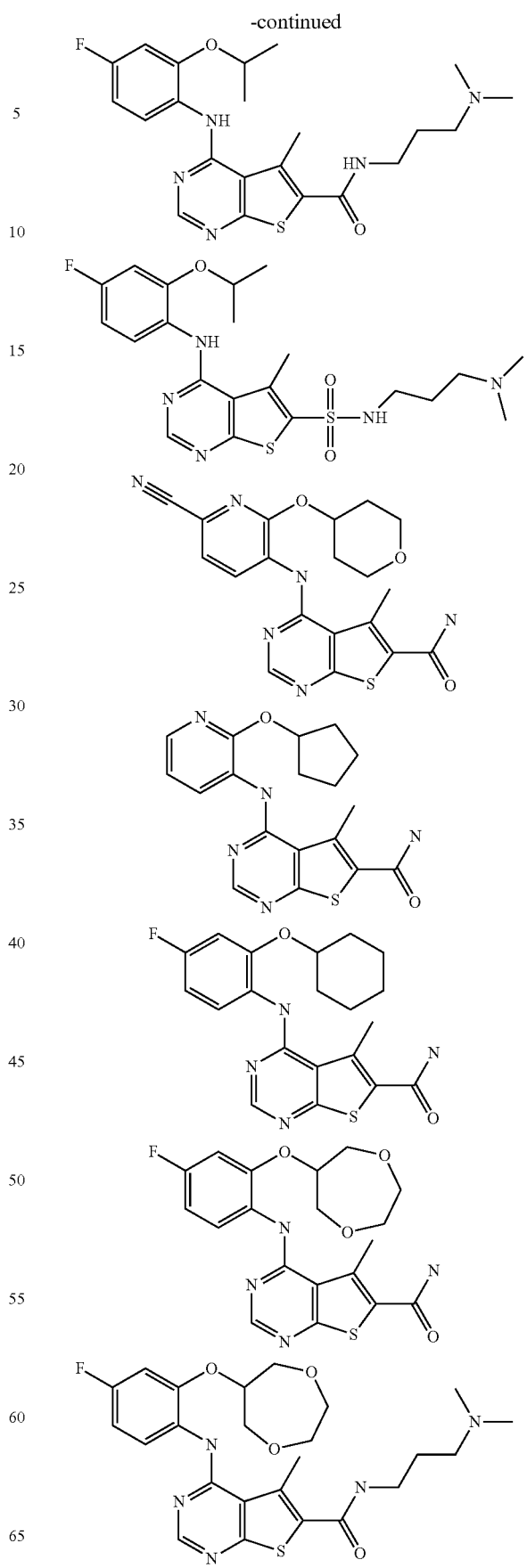

117
-continued
118
-continued
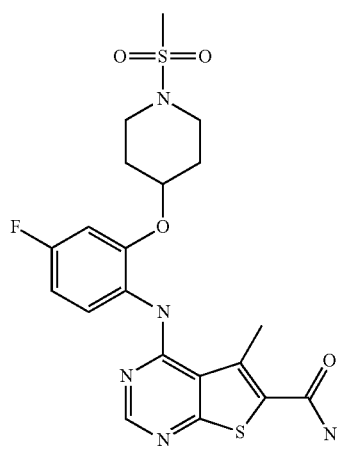
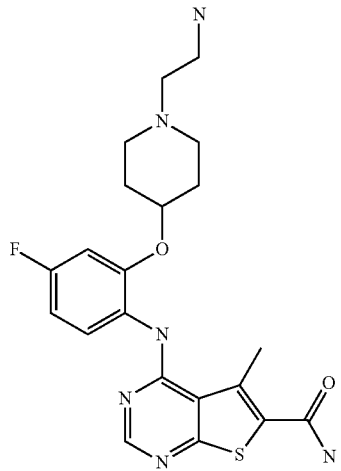
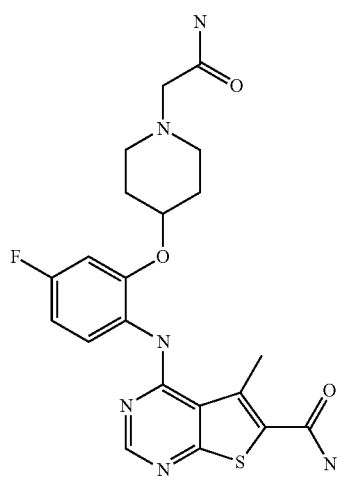

-continued
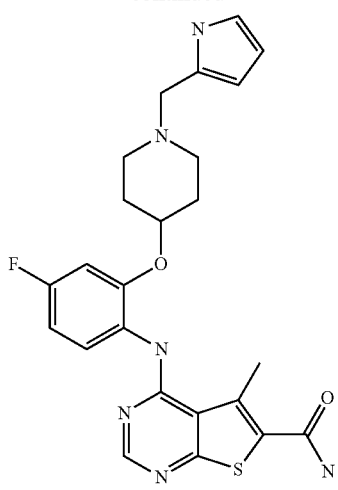
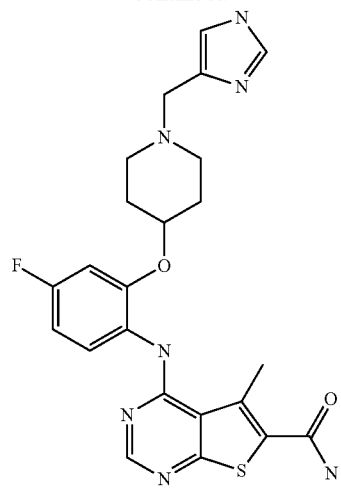
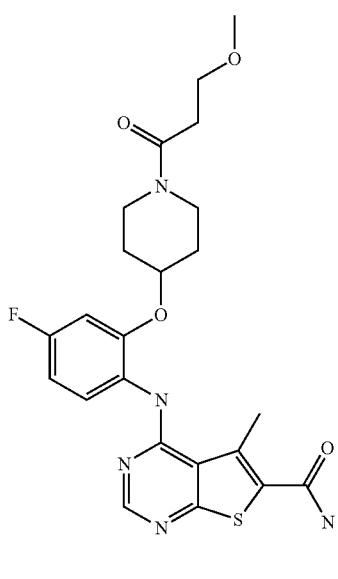
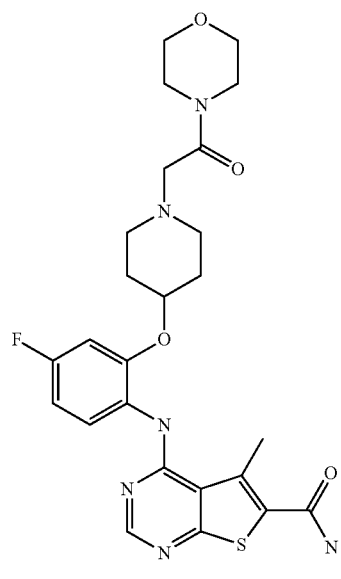
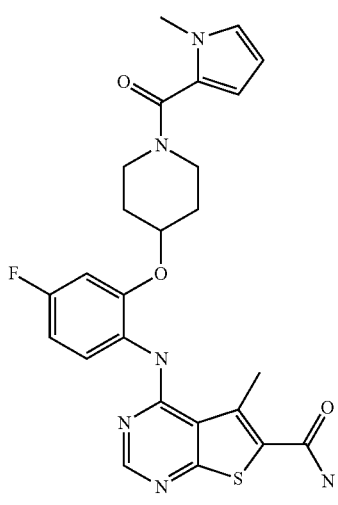
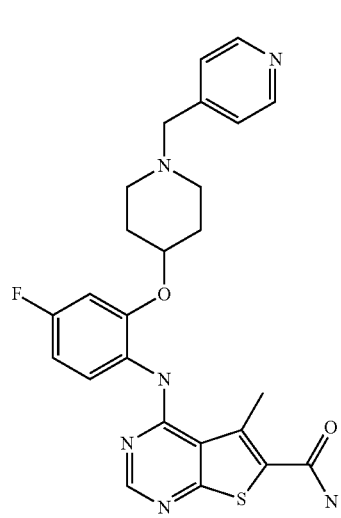

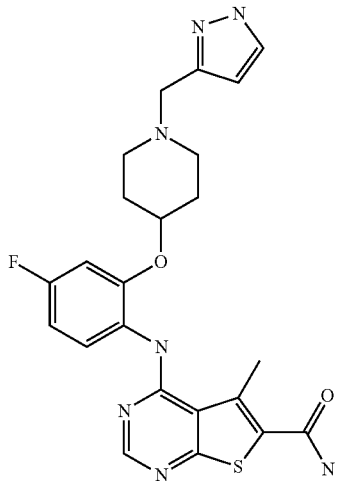

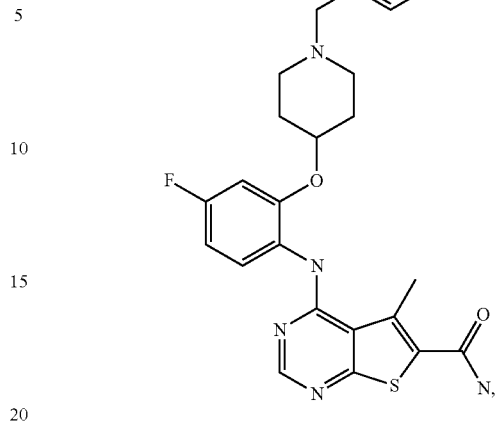

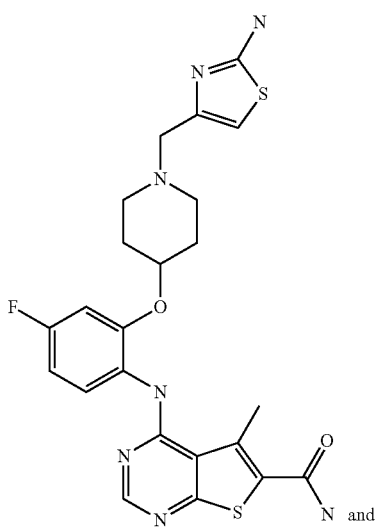 and or a pharmaceutically acceptable salt thereof.

13. A pharmaceutically acceptable salt of a compound according to claim 1.

14. A pharmaceutical composition comprising a compound according to claim 1 or a pharmaceutically acceptable salt thereof and a pharmaceutically acceptable carrier.

15. A pharmaceutical composition according to claim 14 further comprising an additional therapeutic agent selected from a group consisting of an antidiabetic agent, a lipid lowering agent, a cardiovascular agent, an antihypertensive agent, a diuretic agent, a thrombocyte aggregation inhibitor, an antineoplastic agent and an anti-obesity agent.

16. A method of treating diabetes mellitus type II comprising administering to a patient in need an effective amount of a compound according to claim 1 or a pharmaceutically acceptable salt thereof.

17. A method of treating obesity comprising administering to a patient in need an effective amount of a compound according to claim 1 or a pharmaceutically acceptable salt thereof.

* * * * *